US010898484B2

(12) United States Patent
Ahuja et al.

(10) Patent No.: US 10,898,484 B2
(45) Date of Patent: Jan. 26, 2021

(54) METHOD OF REDUCING PULMONARY EXACERBATIONS IN RESPIRATORY DISEASE PATIENTS

(71) Applicant: CELLTAXIS, LLC, Atlanta, GA (US)

(72) Inventors: Sanjeev Ahuja, Carmel, IN (US); Ralph Grosswald, Alpharetta, GA (US); Gregory S. Duncan, Atlanta, GA (US); Eric B. Springman, Atlanta, GA (US)

(73) Assignee: CELLTAXIS, LLC, Atlanta, GA (US)

( * ) Notice: Subject to any disclaimer, the term of this patent is extended or adjusted under 35 U.S.C. 154(b) by 0 days.

(21) Appl. No.: 16/427,571

(22) Filed: May 31, 2019

(65) Prior Publication Data

US 2019/0365750 A1 Dec. 5, 2019

Related U.S. Application Data

(60) Provisional application No. 62/678,964, filed on May 31, 2018, provisional application No. 62/702,038, filed on Jul. 23, 2018.

(51) Int. Cl.
*A61K 31/4985* (2006.01)
*A61P 11/00* (2006.01)
*A61K 31/47* (2006.01)
*A61K 31/519* (2006.01)
*A61K 45/06* (2006.01)

(52) U.S. Cl.
CPC .......... *A61K 31/4985* (2013.01); *A61K 31/47* (2013.01); *A61K 31/519* (2013.01); *A61P 11/00* (2018.01); *A61K 45/06* (2013.01); *A61K 2121/00* (2013.01)

(58) Field of Classification Search
CPC .................... A61K 31/422; A61K 31/4985
See application file for complete search history.

(56) References Cited

U.S. PATENT DOCUMENTS

| | | | |
|---|---|---|---|
| 3,929,765 A | 12/1975 | Suzuki | |
| 4,576,943 A | 3/1986 | Tomcufcik et al. | |
| 4,582,833 A | 4/1986 | Tomcufcik et al. | |
| 5,308,852 A | 5/1994 | Girard et al. | |
| 5,723,492 A | 3/1998 | Chandrakumar et al. | |
| 5,952,349 A | 9/1999 | Asberom et al. | |
| 6,309,561 B1 | 10/2001 | Hasegawa et al. | |
| 6,348,487 B1 | 2/2002 | Connor et al. | |
| 6,372,736 B1 | 4/2002 | Kemp et al. | |
| 6,380,203 B1 | 4/2002 | Bilodeau et al. | |
| 6,407,140 B1 | 6/2002 | Gregory et al. | |
| 6,451,798 B2 | 9/2002 | Varkhedkar et al. | |
| 6,534,521 B2 | 3/2003 | Connor et al. | |
| 6,552,023 B2 | 4/2003 | Zablocki et al. | |
| 6,635,644 B2 | 10/2003 | Salituro et al. | |
| 6,699,873 B1 | 3/2004 | Maguire et al. | |
| 6,734,184 B1 | 5/2004 | Barlaam et al. | |
| 6,846,812 B2 | 1/2005 | Dalko et al. | |
| 6,869,975 B2 | 3/2005 | Abe et al. | |
| 6,875,483 B2 | 4/2005 | Matsuoka et al. | |
| 6,924,313 B1 | 8/2005 | Sikorski et al. | |
| 7,169,779 B2 | 1/2007 | Salituro et al. | |
| 7,402,684 B2 | 7/2008 | Sandanayaka et al. | |
| 7,488,741 B2 | 2/2009 | Lamberty et al. | |
| 7,597,897 B2 | 10/2009 | Capecchi et al. | |
| 7,645,779 B2 | 1/2010 | Abe et al. | |
| 7,674,899 B2 | 3/2010 | Peters et al. | |
| 7,718,669 B2 | 5/2010 | Petry et al. | |
| 7,737,145 B2 | 6/2010 | Arnaiz et al. | |
| 7,816,365 B2 | 10/2010 | Schiemann et al. | |
| 7,820,675 B2 | 10/2010 | Johansson et al. | |
| 7,820,821 B2 | 10/2010 | Gopalaswamy et al. | |
| 7,893,257 B2 | 2/2011 | Grimm et al. | |
| 7,902,181 B2 | 3/2011 | Furber et al. | |
| 7,915,298 B2 | 3/2011 | Gosselin et al. | |
| 7,932,272 B2 | 4/2011 | Nakamoto et al. | |
| 7,935,707 B2 | 5/2011 | Aebi et al. | |
| 8,246,935 B2 | 8/2012 | Mueller-Walz et al. | |
| 8,357,684 B2 | 1/2013 | Bacani et al. | |
| 8,569,303 B2 | 10/2013 | Arnaiz et al. | |
| 8,609,669 B2 | 12/2013 | Xu et al. | |
| 8,846,655 B2 | 9/2014 | Decorte et al. | |
| 9,006,235 B2 | 4/2015 | Naidu et al. | |
| 9,133,146 B2 | 9/2015 | Abeywardane et al. | |
| 9,315,509 B2 | 4/2016 | Arnaiz et al. | |
| 9,820,974 B2 * | 11/2017 | Springman | .......... A61K 31/422 |
| 9,861,601 B2 | 1/2018 | Nicolls et al. | |
| 10,350,197 B2 * | 7/2019 | Springman | ............. A61P 19/02 |

(Continued)

FOREIGN PATENT DOCUMENTS

| | | |
|---|---|---|
| CN | 102030700 A | 4/2011 |
| CN | 103159742 A | 6/2013 |

(Continued)

OTHER PUBLICATIONS

Elborn et al. Clinical and Translational Science, 2017, 10(1): 28-34.*
Elborn et al. Clinical and Translational Science, 2017, 10(1): 20-27.*
De Boeck et al. The lancet Respiratory Medicine, 4(8): 662-674.*
Online "http://web.archive.org/web/20031225052253/http://www.specs.net", Dec. 25, 2003, accessed Apr. 1, 2015.
Online "http://web.archive.org/web/20120317091129/http://www.fchgroup.net/" dated Mar. 1, 2012, accessed Oct. 12, 2016.
Online "http://web.archive.org/web/20130122020518/http://www.chembridge.com/screening_libraries/" 2011, accessed Oct. 10, 2015.
Online: "http ://web.archive.org/web/20070630171813/http://www.enamine.net/index.php?option=com_content&task=view&id=22&menuid=51&PHPSESSID=64a4f248f69d671a413f487bb62c4d90"dated Jun. 30, 2007, accessed Apr. 1, 2015.

(Continued)

*Primary Examiner* — Rei Tsang Shiao
(74) *Attorney, Agent, or Firm* — Elmore Patent Law Group, P.C.; Mahreen Chaudhry Hoda; Carolyn S. Elmore

(57) ABSTRACT

Described are methods of reducing pulmonary exacerbations and methods of treating cystic fibrosis, including methods of reducing pulmonary inflammation, comprising administration of an LTA4h inhibitor.

27 Claims, 21 Drawing Sheets

(56) References Cited

U.S. PATENT DOCUMENTS

| | | |
|---|---|---|
| 2004/0006114 A1 | 1/2004 | Coleman et al. |
| 2004/0198777 A1 | 10/2004 | Ghosh et al. |
| 2005/0043378 A1 | 2/2005 | Axe et al. |
| 2005/0043379 A1 | 2/2005 | Axe et al. |
| 2005/0113408 A1 | 5/2005 | Helgadottir et al. |
| 2006/0063784 A1 | 3/2006 | Wang et al. |
| 2006/0211729 A1 | 9/2006 | Fyrnys et al. |
| 2006/0223792 A1 | 10/2006 | Butler et al. |
| 2007/0112006 A1 | 5/2007 | Schiemann et al. |
| 2007/0155727 A1 | 7/2007 | Chen et al. |
| 2008/0096906 A1 | 4/2008 | Galley et al. |
| 2008/0267885 A1 | 10/2008 | Capecchi et al. |
| 2009/0233922 A1 | 9/2009 | Zhuo et al. |
| 2010/0029619 A1 | 2/2010 | Uchikawa et al. |
| 2010/0029657 A1 | 2/2010 | Levin et al. |
| 2010/0069417 A1 | 3/2010 | Bouaboula et al. |
| 2010/0093668 A1 | 4/2010 | Babin et al. |
| 2010/0099694 A1 | 4/2010 | Babin et al. |
| 2010/0260859 A1 | 10/2010 | Ruddy et al. |
| 2011/0009429 A1 | 1/2011 | Oakley et al. |
| 2011/0009454 A1 | 1/2011 | Matsuzaki et al. |
| 2011/0105475 A1 | 5/2011 | Roche et al. |
| 2012/0028954 A1 | 2/2012 | Goff et al. |
| 2012/0263680 A1 | 10/2012 | Lander et al. |
| 2012/0302610 A1 | 11/2012 | Chakravarty et al. |
| 2013/0116323 A1 | 5/2013 | Tirouvanziam et al. |
| 2013/0123243 A1 | 5/2013 | Arnaiz et al. |
| 2013/0237499 A1 | 9/2013 | Zheng et al. |
| 2013/0251787 A1 | 9/2013 | Nicolls et al. |
| 2016/0068522 A1 | 3/2016 | Davey et al. |
| 2016/0068524 A1 | 3/2016 | Guilford |
| 2016/0068534 A1 | 3/2016 | Guilford |
| 2016/0272649 A1 | 9/2016 | Kochanny et al. |
| 2018/0117014 A1 | 5/2018 | Springman et al. |
| 2018/0230159 A1 | 8/2018 | Arnaiz et al. |
| 2020/0138791 A1 | 5/2020 | Springman et al. |

FOREIGN PATENT DOCUMENTS

| | | |
|---|---|---|
| EP | 1611902 A1 | 1/2006 |
| GB | 1221006 A | 2/1971 |
| JP | 2001354657 A | 12/2001 |
| JP | 2005008581 A | 1/2005 |
| WO | 02064211 A1 | 8/2002 |
| WO | 02069901 A2 | 9/2002 |
| WO | 02072621 A2 | 9/2002 |
| WO | 03010158 A1 | 2/2003 |
| WO | 02072621 A3 | 5/2003 |
| WO | 03037271 A2 | 5/2003 |
| WO | 02069901 A3 | 10/2003 |
| WO | 2004035746 A2 | 4/2004 |
| WO | 2004089410 A1 | 10/2004 |
| WO | 2004099164 A1 | 11/2004 |
| WO | 2005027886 A2 | 3/2005 |
| WO | 2005027886 A3 | 6/2005 |
| WO | 2005054246 A2 | 6/2005 |
| WO | 2007007069 A1 | 1/2007 |
| WO | 2010011912 A1 | 1/2010 |
| WO | 2010015818 A1 | 2/2010 |
| WO | 2011071758 A1 | 6/2011 |
| WO | 2012125832 A2 | 9/2012 |

OTHER PUBLICATIONS

Online: "http://web.archive.org/web/20120301075525/http://www.fchgroup.net/products.php" dated Mar. 1, 2012 accessed Oct. 12, 2016.

STN-Chemical database Registry RN 1322312-60-6 for N-[(3-Phenoxyphenyl)methyl]-6-(1-piperidinyl)-3-Pyridinemethanamine, Entered STN: Aug. 24, 2011.

Inflammation, Wikipedia, 2017, 1.

Pharmaceutical Acceptable Excipients FDA guidelines, 2005, 1-12.

Anonymous, "Celtaxsys Announces Successful Completion of Phase 1 Clinical Trial for Development of CTX-4430—FirstWord Pharma", Retrieved from the Internet: URL:http://www.firstwordpharma.com/node/1139589?tsid=17#axzz4M7ubNn38 [retrieved on Oct. 4, 2016], Sep. 16, 2013.

Arnaiz, D. et al., "Diamine derivatives as inhibitors of leukotriene A4 hydrolase and their preparation, pharmaceutical compositions and use in the treatment of inflammatory disorders", CA147:166353, 2007.

Banker, G. S. et al., Modern Pharmaceutics, 3rd., Marcel Dekker, Inc., NY, 1996, 596.

Beaumont, K. et al., "Design of Ester Prodrugs to Enhance Oral Absorption of Poorly Permeable Compounds: Challenges to the Discovery Scientist", Current Drug Metabolism, 4, 2003, 461-485.

Bhatt, et al., Seminars in Immunology, 33, 2017, 65-73.

Breitenstein, W. et al., "Preparation of substituted pyrrolidines as renin inhibitors", CA145: 103533, 2006.

Bridger, G. J. et al., "Preparation of piperidines as chemokine receptor, particularly CCR5, modulators for treatment of inflammatory and autoimmune diseases", CA143: 97274, 2005.

Brodin, P. et al., "Benzamides, pyridopyrimidines and related compounds as antiinfective compounds and their preparation and use in the treatment of tuberculosis", CA152: 168983, 2010.

Burstein, S. H., et al., "Ajulemic acid: potential treatment for chronic inflammation," Pharmacology Research & Perspectives, 2018, e00394.

Celli et al. Respiratory Medicine, 2011, vol. 105, pp. 1176-1188 (Year: 2011).

Celtaxsys Announces Full Enrollment of Its Landmark EMPIRE-CF Phase 2b Clinical Trial Assessing the Potential of Novel Anti-inflammatory Investigational Therapy, Oral Acebilustat, to Preserve Lung Function in CF Patients, May 17, 2020. https://celtaxsys.com/2017/05/17/celtaxsys-announces-full-enrollment-of-landmark-cf-ph2btrial/.

Chmiel, J. F., et al., "A Phase 2 Study of the Safety, Pharmacokinetics and Efficacy of Anabasum (JBT-101) in Cystic Fibrosis (CF)," Powerpoint Presentation 2017.

Chmiel, J. F., et al., "Use of ibuprofen to assess inflammatory biomarkers in induced sputum: Implications for clinical trials in cystic fibrosis," Journal of Cystic Fibrosis 14 (2015) 720-726.

Coats, S. J. et al., "4-Substituted 2-phenoxyphenylamines as delta opioid receptor modulators and their preparation and use in the treatment of diseases", CA154: 540153, 2011.

Connors, K. A. "The Stability of Cyclodextrin Complexes in Solution", Chem. Rev., 97, 1997, 1325-1357.

De Boeck, K., et al., "Progress in therapies for cystic fibrosis," Lancet Respir Med 2016; 4: 662-74.

De Boer, K., et al., "Exacerbation frequency and clinical outcomes in adult patients with cystic fibrosis," Thorax, 2011; 66: 680e685.

Doring, G., et al., "BIIL 284 reduces neutrophil numbers but increases P. aeruginosa bacteremia and inflammation in mouse lungs," Journal of Cystic Fibrosis, 13 (2014) 156-163.

Elborn, J. S., et al., "EMPIRE-CF: A phase II randomized placebo-controlled trial of once-daily, oral acebilustat in adult patients with cystic fibrosis—Study design and patient demographics," Contemporary Clinical Trials 72 (2018) 86-94.

Elborn, JS, et al., "Phase I Studies of Acebilustat: Pharmacokinetics, Pharmacodynamics, Food Effect, and CYP3A Induction," Clin Transl Sci (2017) 10, 20-27.

Fieser, L. et al., Reagents for Organic Synthesis, vol. 1, Wiley: NY, Pub Date Discrepancy, 1974, 723-730.

Greene, T. W. et al., Protective Groups in Organic Synthesis, John Wiley & Sons: NY, Pub Date Discrepancy, 1982, 218-220, 224, 251.

Grice, et al. J. Med. Chem., 2008, vol. 51, pp. 4150-4169 (Year: 2008).

Hauptmann, et al., Chem. Rev., 62, 1962, 347-404.

Hutchins, T. O. "Selective Reductive Displacement of Alkyl Halides and Sulfonate Esters with Cyanoborohydride Reagents in Hexamethylphosphoramide", J. Org. Chem., 42(1), 1977, 82-91.

Jantzen, et al., Modern Pharmaceutics, 1996, 596.

Khim, et al., "Discovery of novel and potent aryl diamines as leukotriene A4 hydrolase inhibitors", Bioorg. Med. Chem. Lett., 18(14): Jul. 15, 2008, 3895-3898.

(56) References Cited

OTHER PUBLICATIONS

King, F. D. et al., "Bioisosteres, Conformational Restriction, and Pro-drugs—Case History: An Example of a Conformational Restriction Approach", Ch. 14 in Med. Chem: Principle & Practice, Jan. 1, 1994, 206-2335.

Konstan, M. W., et al., "A randomized double blind, placebo controlled phase 2 trial of BIIL 284 BS (an LTB4 receptor antagonist) for the treatment of lung disease in children and adults with cystic fibrosis," *J Cyst Fibros*. Mar. 2014; 13(2): 148-155.

Konstan, M. W., et al. "Association of High-Dose Ibuprofen Use, Lung Function Decline, and Long-Term Survival in Children with Cystic Fibrosis," Ann Am Thorac Soc., vol. 15, No. 4, pp. 485-493, Apr. 2018.

Konstan, M. W., et al.. "Effect of High-Dose Ibuprofen in Patients With Cystic Fibrosis," The New England Journal of Medicine, Mar. 30, 1995.

Konstan, M. W., et al., "Effect of Dornase Alfa on Inflammation and Lung Function: Potential Role in the Early Treatment of Cystic Fibrosis," *J Cyst Fibros*. Mar. 2012; 11(2): 78-83.

Konstan, M.W., et al., Ibuprofen attenuates the inflammatory response to *Pseudomonas aeruginosa* in a rat model of chronic pulmonary infection. Implications for anti-inflammatory therapy in cystic fibrosis. Am Rev Respir Dis., 1990; 141:186-92.

Kurimura, M. et al., "Preparation of N,N-substituted 3-aminopyrrolidine compounds useful as monoamines reuptake inhibitors", CA149: 53863, 2008.

Labaudiniere, R. et al., "w-[(w-Arylalkyl)aryl]alkanoic Acids: A New Class of Specific LTA4 Hydrolase Inhibitors", J. Med. Chem., 35, 1992, 3156-3169.

Martin, Y. C. et al., "Do Structurally Similar Molecules Have Similar Biological Activity?", J. Med. Chem., 45, 2002, 4350-4358.

Mitchell, R. H. et al., "The Neutral Deoxygenation (Reduction) of Aryl Carbonyl Compounds With Raney-Nickel. An Alternative to the Clemmenson, Wolf-Kishner or Mozingo (Thioketal) Reductions", Tetrahedron Letters, 21, 1980.

Penning, T. D. et al., "Structure-Activity Relationship Studies on 1-[2-(4-Phenylphenoxy)ethyl]pyrrolidine (SC-22716), a Potent Inhibitor of Leukotriene A4 (LTA4) Hydrolase", J. Med. Chem., 43(4), 2000, 721-735.

Pitt, W. R. et al., "Heteroaromatic Rings of the Future", J. Med. Chem., 52, 2009, 2952-2963.

Pozharskii, et al., Heterocycles in Life and Society Wiley, 1997, 1-6.

Rautio, "Prodrugs: design and clinical Applications," J. et al., Nat. Rev. Drug Disc., vol. 7, 2008, 255-270.

Szczesniak, R. et al., "Use of FEV1 in cystic fibrosis epidemiologic studies and clinical trials: A statistical perspective for the clinical researcher", Journal of Cystic Fibrosis, vol. 16, 2017, 318-326.

Shen, H. C. et al., "A strategy of employing aminoheterocycles as amide mimics to identify novel, potent and bioavailable soluble epoxide hydrolase inhibitors", Bioorganic & Medicinal Chemistry Letters, 19, 2009, 5716-5721.

Shim, Y. M. et al., "Leukotriene A4 Hydrolase—An Evolving Therapeutic Target", Inflammatory Diseases—Immunopathology, Clinical and Pharmacological Bases, Dr Mahin Khatami (Ed.), InTech, 2012, 253-278.

Skerlj, R. et al., "Design and synthesis of pyridin-2-ylmethylaminopiperidin-1-ylbutyl amide CCR5 antagonists that are potent inhibitors of M-tropic (RS) HIV-1 replication", CA156: 10919, 2011.

Springman, E. B. et al., "A Phase 1 Study of Human Safety, Pharmacokinetics and Pharmacodynamics of CTX-4430", Pediatric Pulmonology, John Wiley, New York, NY, US, vol. 48, Oct. 1, 2013.

Vandevanter, D. R., et al., "IV-Treated Pulmonary Exacerbations in the Prior Year: An Important Independent Risk Factor for Future Pulmonary Exacerbation in Cystic Fibrosis," J. Cyst Fibros. May 2016; 15(3): 372-379.

Vippagunta, S. R. et al., "Crystalline Solids", Advanced Drug Delivery Reviews, 48, 2001, 3-26.

Waters, V., et al., "Effect of pulmonary exacerbations on long-term lung function decline in cystic fibrosis," Eur Respir J., 2012; 40: 61-66.

Wolff, M. E. Burger's Medicinal Chemistry and Drug Discovery, Fifth Edition, vol. 5(1): Principles and Practice published by John Wiley and Sons, 1994, 975-977.

Cystic Fibrosis Foundation Patient Registry, 2015 Annual Data Report, Bethesda, Maryland © 2016 Cystic Fibrosis Foundation.

\* cited by examiner

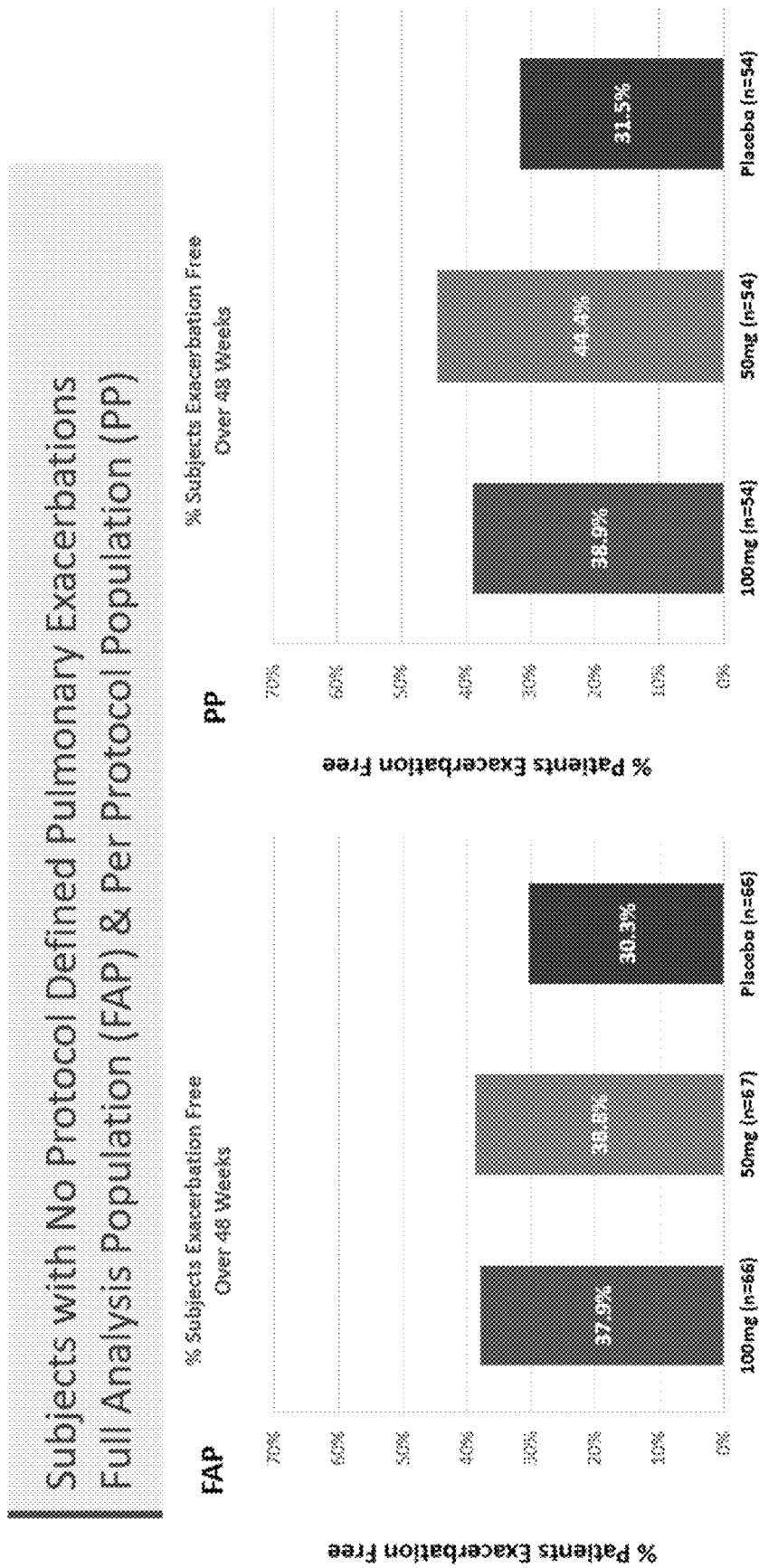

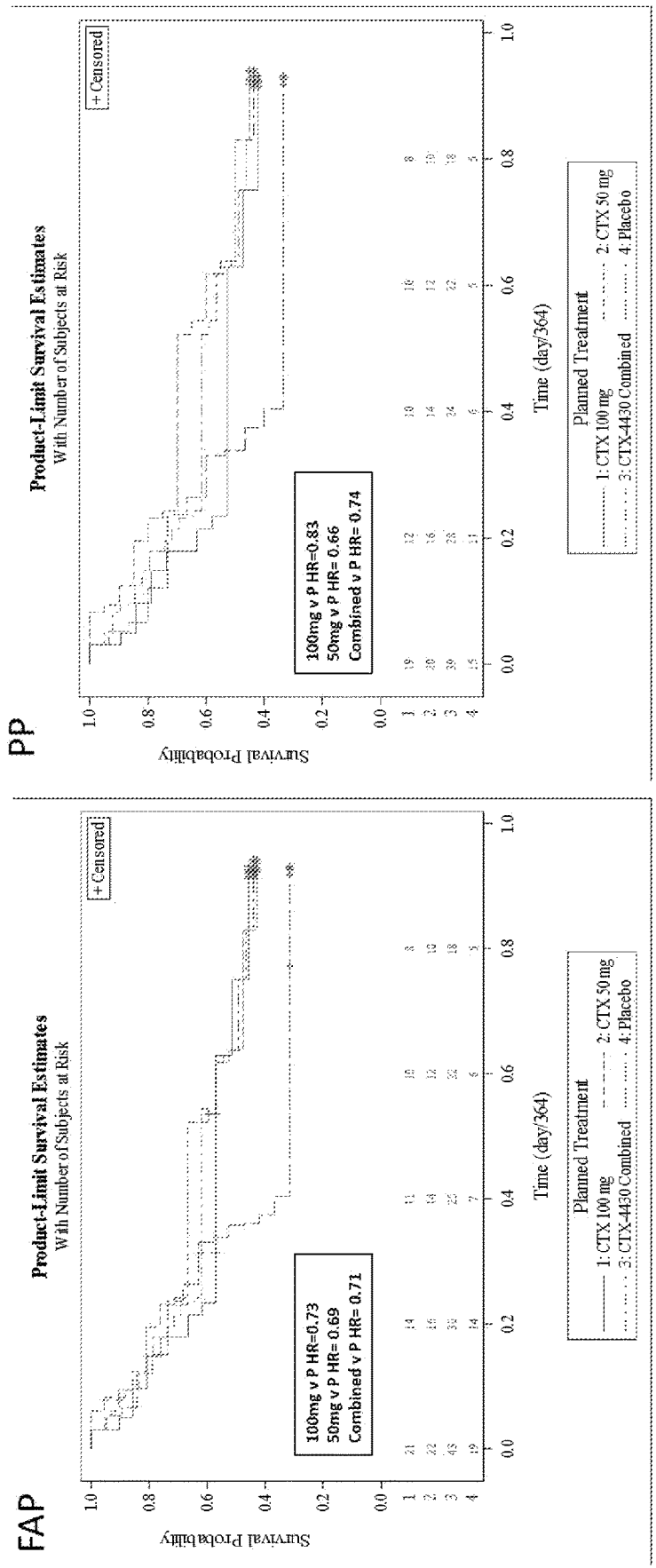

METHOD OF REDUCING PULMONARY EXACERBATIONS IN RESPIRATORY DISEASE PATIENTS

RELATED APPLICATIONS

This application claims the benefit of U.S. Provisional Application No. 62/678,964 filed May 31, 2018 and U.S. Provisional Application No. 62/702,038 filed Jul. 23, 2018. The entire contents of the above-referenced applications are incorporated by reference herein.

BACKGROUND OF THE INVENTION

Pulmonary pathology in the cystic fibrosis (CF) lung is characterized by high levels of inflammation that leads to pulmonary exacerbations, lung function decline and associated morbidity and mortality. Inflammatory lung damage is evident early in life, with increased neutrophil elastase in bronchoalveolar lavage fluid clearly linked to the risk of developing structural lung damage (including bronchiectasis) at as early as three months of age in children with cystic fibrosis [Sly et al., 2013]. Inflammation-induced damage can occur even in the absence of detectable infection [Tirouvanziam et al., 2002; Verhaeghe et al., 2007]. Inflammation also persists despite high standards of care and novel therapies such as cystic fibrosis transmembrane conductance regulator (CFTR) modulators [Rowe et al., 2014]. Chronic inflammation in the CF lung is driven by the persistent recruitment of immune cells, principally neutrophils, into the airways [Downey et al., 2009]. Modulation of the inflammatory mediators that drive neutrophil influx may provide a viable therapeutic pathway to reduce inflammation in the lung [Cantin et al., 2015].

Despite the recognition that treatment of chronic lung inflammation is an unmet need in CF treatment, studies of anti-inflammatory agents have yielded mixed results. In high doses, the nonsteroidal anti-inflammatory drug ibuprofen slows lung function decline in patients and improves survival in children with CF [Konstan et al., 1995; Konstan et al., 2018, Lands et al. 2007, Lands et al., 2016]. Yet, despite evidence of efficacy, high dose ibuprofen is infrequently used to treat inflammation in CF due to concerns of gastrointestinal and renal toxicity and the need for pharmacokinetic-based dosing [Chmiel et al., 2015; Balfour-Lynn et al., 2007]. A clinical trial of the anti-inflammatory, BIIL 284 (amelubant), an antagonist of the BLT1 receptor, in patients with stable CF lung disease was terminated early due to an increase in respiratory serious adverse events characterized by an increased presentation of symptoms associated with pulmonary exacerbation [Konstan et al. 2014]. This trial has been described as a "cautionary tale" for the administration of anti-inflammatory compounds in CF due to their potential to suppress the inflammatory response and thus increase the risk of infection [Konstan et al. 2014]. Doring et al. (2014) suggested a mechanism for this increased risk by demonstrating that administration of BIIL 284 to mice (at doses of 0.3 to 100 mg/kg) significantly down-regulated Mac-1 (CR3) and reduced the number of neutrophils in the lungs and the airways of *P. aeruginosa*-infected mice.

The target of BIIL 284, the BLT1 receptor, is the primary receptor for leukotriene B4 ($LTB_4$). $LTB_4$ is an immune cell chemoattractant and activator implicated in the initiation of cytokine and chemokine cascades that amplify and perpetuate inflammation via neutrophil swarming behavior [Lämmerman et al., 2013; Afonso, et al. 2012; Sadik and Luster, 2012]. $LTB_4$ is generated from leukotriene A4 ($LTA_4$) by the enzyme leukotriene A4 hydrolase ($LTA_4$-h). $LTA_4$-h is a monomeric, soluble 69 kD zinc metalloenzyme that catalyses two reactions: the stereospecific epoxide hydrolase reaction to convert $LTA_4$ to leukotriene B4 ($LTB_4$) and an aminopeptidase cleavage of small peptide substrates. Inhibition of $LTA_4$-h has the potential to reduce $LTB_4$ production, thus reducing neutrophil influx and the release of neutrophil-derived enzymes such as neutrophil elastase (FIG. 1). [Woolhouse et al., 2002; Tirouvanziam 2006].

$LTA_4$-h inhibitors have been described, for example, in U.S. Pat. Nos. 7,737,145, 9,820,974, and U.S. Patent Application Publication No. 20100210630A1, the contents of each of which are incorporated by reference herein. A specific $LTA_4$-h inhibitor described in these patent publications is 4-{[(1S,4S)-5-({4-[4-oxazol-2-yl-phenoxy]phenyl}methyl)-2,5-diazabicyclo[2.2.1]heptan-2-yl]methyl}benzoic acid (also referred to herein as CTX-4430 and by its International Nonproprietary Name, acebilustat). Acebilustat is an oral therapy that modulates $LTB_4$ production and targets inflammatory process in CF [Elborn et al., 2017a]. In two Phase I trials, acebilustat reduced $LTB_4$ production and other inflammatory markers in healthy volunteers and patients with CF [Elborn et al., 2017a, Elborn et al., 2017b].

There remains a need in the art for safe and effective anti-inflammatory treatment of cystic fibrosis. It would therefore be advantageous to develop additional methods of reducing pulmonary inflammation in cystic fibrosis patients and/or prevent or reduce loss of lung function and/or reduce pulmonary exacerbations in CF patients. In addition, considering the lack of clear precedent for successfully developing an anti-inflammatory treatment in cystic fibrosis, identifying an appropriate treatment population and/or clinical outcome is also important.

SUMMARY OF THE INVENTION

The present invention is directed to a method of treating cystic fibrosis and other respiratory diseases, including methods of decreasing pulmonary exacerbations, including reducing the risk of pulmonary exacerbations and/or reducing the rate (such as the annual or annualized rate), number or frequency of pulmonary exacerbations, increasing the time to first pulmonary exacerbation, and/or reducing pulmonary exacerbations such that the patient does not experience any pulmonary exacerbations for at least one year (after initiating treatment with acebilustat). In certain embodiments, the methods comprise orally administering to cystic fibrosis or other respiratory disease patients acebilustat at a total daily dose of about 100 mg or less, about 50 mg or less, from about 50 mg to about 100 mg, about 100 mg, or about 50 mg. The methods also include reducing pulmonary inflammation and methods of treating chronic pulmonary inflammation in a cystic fibrosis patient.

It has been discovered that a major effect of acebilustat treatment is reduction in pulmonary exacerbations, including reducing the rate (for example, number or frequency) of pulmonary exacerbations and/or increasing the time to first pulmonary exacerbation. In addition, acebilustat treatment resulted in an increased proportion of patients that were exacerbation free (experienced no pulmonary exacerbations) after initiating acebilustat treatment over the course of the 48 weeks of study. It has been discovered that acebilustat treatment has its greatest effect in cystic fibrosis patients having a phenotype characterized as mild lung disease (e.g., patients having a $FEV_1pp$ greater than about 65% at the start of treatment or at baseline) as compared to patients with more severe lung disease. Specifically, anti-inflammatory treatment comprising acebilustat reduced the rate of pulmonary exacerbations and increased the time to first pulmonary exacerbation in cystic fibrosis patients of the mild lung disease phenotype as compared to that in patients treated with placebo or in patients with moderate or severe lung disease. This effect was observed whether patients were taking or not taking concomitant treatment with CFTR modulator therapy. Notably, the greatest benefit of acebilustat treatment was observed in patients having the mild lung disease phenotype and taking CFTR modulator therapy, although a benefit was also observed in patients with mild disease not taking CFTR modulator therapy. Furthermore, the benefit of acebilustat treatment observed in patients taking concomitant CFTR modulator therapy was observed regardless of lung disease phenotype, and the effect on pulmonary exacerbation was greater than that in patients not taking CFTR modulator therapy in this population with a broader range of disease severity.

Therefore, in certain aspects, invention is directed to a method of decreasing pulmonary exacerbations, including reducing the rate (for example, number or frequency) of pulmonary exacerbations or increasing the time to first pulmonary exacerbation, in a patient in need thereof comprising orally administering to the patient acebilustat at a total daily dose of about 100 mg or less. The patient in need of treatment can be a patient suffering from a respiratory condition characterized by the occurrence of pulmonary exacerbations. Such respiratory conditions include, for example, cystic fibrosis, bronchiectasis, chronic obstructive pulmonary disease, and interstitial lung disease. In certain aspects, the invention includes a method of decreasing pulmonary exacerbations, including reducing the number or frequency of pulmonary exacerbations or increasing the time to first pulmonary exacerbation, in a cystic fibrosis patient comprising orally administering to the patient acebilustat at a total daily dose of about 100 mg or less. In certain aspects, the patient, such as a cystic fibrosis patient, does not experience any pulmonary exacerbations for at least one year after initiating oral administration with acebilustat. Acebilustat can also, for example, be administered to the patient, such as a cystic fibrosis patient, at a total daily dose of about 50 mg or less, or about 100 mg, or about 50 mg, about 50 mg to about 100 mg. In yet additional aspects, the total daily dose of acebilustat is 100 mg. In certain aspects, the patient, such as a cystic fibrosis patient, has a mild lung disease phenotype, for example, the patient has a $FEV_1pp$ greater than about 65% at baseline, greater than about 68% at baseline, greater than about 70% at baseline (the CF community standard definition of "mild" CF disease), or greater than about 75% at baseline. In yet additional aspects, the patient, such as a cystic fibrosis patient, has a $FEV_1pp$ greater than or equal to about 65% at baseline, greater than or equal to about 68% at baseline, or greater than or equal to about 70% at baseline, or greater than or equal to about 75% at baseline. In certain aspects, the method comprises measuring $FEV_1pp$ in a patient (at baseline or prior to initiating treatment), for example, by spirometry, and administering acebilustat (at a total daily dose of about 100 mg or less, as described herein) to the patient if the patient has an $FEV_1pp$ greater than or equal to about 65%, greater than or equal to about 68%, or greater than or equal to about 70%, or greater than or equal to about 75%. In additional embodiments, the patient does not experience a pulmonary exacerbation for at least forty-eight weeks after initiating treatment with acebilustat. In some embodiments, the patient is a cystic fibrosis patient undergoing concomitant treatment with a CFTR modulator, such as a CFTR corrector and/or CFTR potentiator. In further aspects, the patient is not undergoing concomitant treatment with a CFTR modulator, for example, the patient is not undergoing concomitant treatment with a CFTR corrector and/or a CFTR potentiator.

The invention also includes a method of treating cystic fibrosis in a patient in need thereof and/or a method of reducing pulmonary exacerbations and/or reducing pulmonary inflammation in a cystic fibrosis patient, wherein the patient of the mild lung disease phenotype, for example, having a $FEV_1pp$ greater than about 65% at baseline, the method comprising orally administering to the patient acebilustat at a total daily dose of about 100 mg or less. The patient of the mild lung disease phenotype can, for example, have a $FEV_1pp$ greater than about 68%, greater than about 70%, or greater than about 75% at baseline. In yet additional aspects, the patient can, for example, have a $FEV_1pp$ greater than or equal to about 65%, greater than or equal to 68%, greater than or equal to about 70%, or greater than or equal to about 75% at baseline. In additional aspects, the acebilustat is administered to the patient at a total daily dose of about 50 mg or less, about 50 mg to about 100 mg, about 100 mg, or about 50 mg. In specific aspects, the total daily dose of acebilustat is 100 mg. In some embodiments, the cystic fibrosis patient of the mild lung disease phenotype is undergoing concomitant treatment with a CFTR modulator, such as a CFTR corrector, and/or a CFTR potentiator. In further aspects, the patient is not undergoing concomitant treatment with a CFTR modulator, for example, the patient is not undergoing concomitant treatment with a CFTR modulator, such as a CFTR corrector and/or a CFTR potentiator. In yet additional aspects, the patient experiences a decrease in the number or frequency of pulmonary exacerbations in the twelve month period after initiating treatment with acebilustat. In further aspects, the patient does not experience a pulmonary exacerbation for at least forty-eight weeks, for example, at least one year, after initiating treatment with acebilustat. In certain aspects, the method comprises measuring $FEV_1pp$ in a patient (at baseline or prior to initiating treatment), for example by spirometry, and administering acebilustat (at a total daily dose of about 100 mg or less, as described herein) to the patient if the patient has an $FEV_1pp$ greater than or equal to about 65%, greater than or equal to about 68%, or greater than or equal to about 70%, or greater than or equal to about 75%.

The invention additionally includes a method of treating cystic fibrosis in a patient in need thereof comprising orally administering to the patient acebilustat at a total daily dose of about 100 mg or less, about 50 mg or less, of about 100 mg, of about 50 mg, or about 50 mg to about 100 mg, wherein pulmonary inflammation in the patient is reduced but the risk of pulmonary infection is not increased. In certain aspects, the total daily dose of acebilustat administered to the cystic fibrosis patient is 100 mg. In some embodiments, the patient has a mild lung disease phenotype, for example, a FEV1pp greater than about 65% at baseline, a $FEV_1pp$ greater than about 68% at baseline, a $FEV_1pp$ greater than about 70%, or greater than about 75% at baseline. In yet additional aspects, the patient can, for example, have a $FEV_1pp$ greater than or equal to about 68% at baseline, greater than or equal to about 70% at baseline, or greater than or equal to about 75% at baseline. In certain aspects, the method comprises measuring $FEV_1pp$ in a patient (at baseline or prior to initiating treatment), for example by spirometry, and administering acebilustat (at a total daily dose of about 100 mg or less, as described herein) to the patient if the patient has an $FEV_1pp$ greater than or equal to about 65%, greater than or equal to about 68%, or greater than or equal to about 70%, or greater than or equal to about 75%. In certain aspects, the cystic fibrosis patient is undergoing concomitant treatment with a CFTR modulator, such as a CFTR corrector and/or CFTR potentiator. In further aspects, the patient is not undergoing concomitant treatment with a CFTR modulator, for example, the patient is not undergoing concomitant treatment with a CFTR corrector and/or a CFTR potentiator. In yet additional aspects, the patient experiences a decrease in the rate of pulmonary exacerbations in the twelve month period after initiating treatment with acebilustat. In further aspects, the patient does not experience a pulmonary exacerbation for at least forty-eight weeks, for example, at least one year, after initiating treatment with acebilustat.

The invention further includes methods of decreasing pulmonary exacerbations, including reducing the rate (for example, number or frequency) of pulmonary exacerbations or increasing the time to first pulmonary exacerbation, in a cystic fibrosis patient comprising orally administering to the patient acebilustat at a total daily dose of about 100 mg or less, wherein the patient is the cystic fibrosis patient undergoing concomitant treatment with a CFTR modulator, such as a CFTR corrector and/or CFTR potentiator. In certain aspects, the patient does not experience any pulmonary exacerbations for at least one year after initiating oral administration with acebilustat. Acebilustat can, for example, be administered at a total daily dose of about 50 mg or less, or about 100 mg, or about 50 mg, about 50 mg to about 100 mg.

BRIEF DESCRIPTION OF THE FIGURES

FIGS. 6A and 6B are bar graphs showing the percentage of patients treated with 100 mg acebilustat, 50 mg acebilustat, or placebo that were exacerbation free over 48 weeks for the full analysis population (FAP) (FIG. 6A) and per-protocol (PP) (FIG. 6B) across all lung disease phenotypes.

FIGS. 13A and 13B are Kaplan-Meier plots showing fraction of patients remaining exacerbation free as a function of time (as a fraction of 364) for patients on CFTR modulator therapy at baseline administered acebilustat at 100 mg, 50 mg, combined treatment groups, or placebo, for the full analysis population (FAP) (FIG. 12A) and per-protocol (PP) (FIG. 12B).

FIG. 15A) compared to patients having baseline FEV1pp>75% (the prespecified definition of "mild" CF used in the clinical study; FIG. 15B).

FIG. 16A) and not taking ("Off"; FIG. 16B) concomitant CFTR modulator therapy.

DETAILED DESCRIPTION OF THE INVENTION

Figure 1:
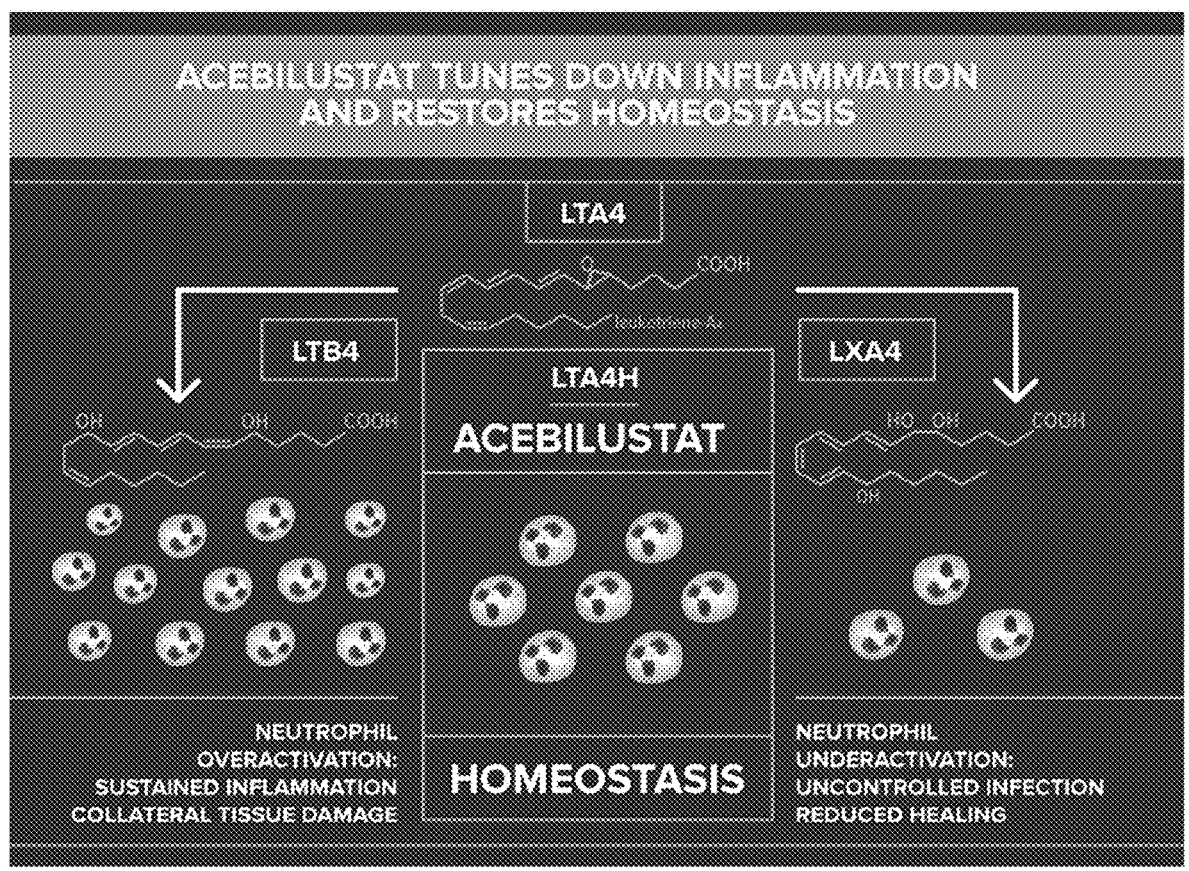
FIG. 1 is a drawing showing the mode of action of Acebilustat (CTX-4430). In many inflammatory diseases, the neutrophil signaling pathway governed by the potent inflammation mediator leukotriene B4 (LTB4) and the recovery mediator lipoxin A4 (LXA4) becomes imbalanced, leading to over-activation of neutrophils with sustained inflammation and tissue damage. Acebilustat tunes down the over-active neutrophil response by modulating this pathway.

A description of preferred embodiments of the invention follows.

As used herein, the words "a" and "an" are meant to include one or more unless otherwise specified. For example, the term "an additional therapeutic agent" encompasses both a single additional therapeutic agent and a combination of two or more additional therapeutic agents.

It is to be understood that when the range of the dose or amount of a drug or active ingredient (e.g., acebilustat and/or CFTR modulator, such as CFTR potentiator and/or CFTR corrector, and/or additional therapeutic agent) is described as "between" a low end of the range and "between" a high end of the range, the range is meant to include both, the low end and the high end as well as doses in between the low and high ends. For example, for "a dose between about 50 mg and about 100 mg," it is to be understood that the range includes the low end of the range, about 50 mg, and the high end of the range, about 100 mg, as well as the doses in between, for example, about 75 mg. In addition, "a dose of about 50 mg or less" is intended to include the about 50 mg dose as well as doses less than about 50 mg.

The term "about" as used herein, in reference to a numerical value or range, allows for a degree of variability in the value or range, for example, within 10%, within 5%, or within 4%, or within 2% of the value or range.

The methods of the invention comprise administration of an effective oral dose of 4-{[(1S,4S)-5-({4-[4-oxazol-2-yl-phenoxy]phenyl}methyl)-2,5-diazabicyclo[2.2.1]heptan-2-yl]methyl}benzoic acid (CTX-4430; Acebilustat) to human patients. This compound and methods for the preparation thereof have been described in detail in U.S. Pat. Nos. 7,737,145, 9,820,974, and U.S. Patent Application Publication No. 20100210630A1, the contents of each of which are incorporated by reference herein. Acebilustat has the chemical structure shown below:

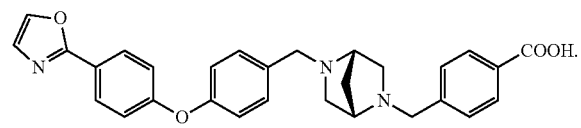 [SMILES: O=C(O)c1ccc(CN2C[C@@H]3C[C@H]2CN3Cc2ccc(Oc3ccc(-c4ncco4)cc3)cc2)cc1]

The invention encompasses methods of reducing pulmonary exacerbations in a patient in need thereof as well as methods of treating pulmonary inflammation and/or reducing chronic lung inflammation and/or reducing pulmonary inflammation and/or decreasing pulmonary exacerbations in a cystic fibrosis patient in need thereof, the methods comprising oral administration of about 100 mg acebilustat to said patient; for example, chronic oral administration (e.g., for a long period of time and/or throughout the patient's treatment). The invention also encompasses a method of reducing pulmonary exacerbations in a patient in need thereof as well as a method of treating pulmonary inflammation and/or reducing chronic lung inflammation and/or reducing pulmonary inflammation and/or decreasing pulmonary exacerbations in a cystic fibrosis patient in need thereof comprising chronic oral administration of about 50 mg acebilustat to said patient; for example, chronic oral administration (e.g., for a long period of time and/or throughout the patient's treatment). Acebilustat can, for example, be administered at a dose of about 50 mg every 12 or 24 hours (or once or twice a day), or at a dose of about 100 mg every 24 hours (or once a day). The invention additionally encompasses a method of reducing pulmonary exacerbations in a patient in need thereof as well as a method of treating pulmonary inflammation and/or reducing chronic lung inflammation and/or reducing pulmonary inflammation and/or decreasing pulmonary exacerbations in a cystic fibrosis patient comprising chronic oral administration of about 100 mg or less, or of about 50 mg or less, of acebilustat to said patient; for example, chronic oral administration (e.g., for a long period of time and/or throughout the patient's treatment). The total daily dose of acebilustat can be a dose that is 50 mg or less, for example, about 25 mg, about 15 mg, about 10 mg, or about 5 mg. The total daily dose of acebilustat can also be from about 50 mg to about 100 mg, for example, about 75 mg. In certain aspects, the dose of acebilustat is about 25 mg administered twice a day or a dose between about 25 and 50 mg administered twice a day. Acebilustat can be administered with or without food.

A major effect of acebilustat treatment is a reduction in pulmonary exacerbations or a reduction in the rate of pulmonary exacerbations, including a higher proportion of patients that were exacerbation free (or had no pulmonary exacerbations) after initiating acebilustat treatment (as compared to placebo). In certain aspects, the rate or frequency of pulmonary exacerbations is decreased as compared to that before initiating acebilustat treatment. Pulmonary exacerbations, which are a clinical marker of lung inflammation, are significant events leading to acute decompensation and chronic decline of lung function and are strongly related to reduced survival. The rate of pulmonary exacerbations is reduced when the number of pulmonary exacerbations in a certain period of time (for example, over forty-eight weeks or a year) is less than that for the same period of time prior to initiating the treatment and/or as compared to that without acebilustat (for example, treated with placebo or untreated group, and/or as would have been predicted from prior medical history). The rate of pulmonary exacerbation can, for example, be an annual rate of pulmonary exacerbations or an annualized rate of pulmonary exacerbations. A reduction in the rate, number, or frequency of pulmonary exacerbations includes, for example, a reduction of at least about 5%, at least about 10%, at least about 15%, at least about 20%, at least about 25%, at least about 30%, at least about 35%, at least about 40%, at least about 45%, at least about 50%, at least about 55%, at least about 60%, at least about 65%, at least about 70%, at least about 75%, at least about 80%, at least about 85%, at least about 90%, and at least about 95%. In certain aspects, the rate, number, or frequency of pulmonary exacerbations is reduced by at least about 15%, or at least about 20%, or at least about 25%, or at least about 30%, or at least about 35%, or at least about 40%. When acebilustat is administered concomitantly with a CFTR modulator, the rate, number, or frequency of pulmonary exacerbations can be reduced by at least about 15%, or at least about 20%, or at least about 25% as compared to that with the CFTR modulator without acebilustat. When acebilustat is administered concomitantly with a CFTR modulator to a patient of the mild lung disease phenotype, as described herein, the rate, number, or frequency of pulmonary exacerbations can, for example, be reduced by at least about 15%, at least about 20%, at least about 25%, at least about 35%, at least about 40%, or at least about 50% as compared to that with the CFTR modulator without acebilustat.

The invention encompasses methods of reducing pulmonary exacerbations, including reducing the number or frequency of pulmonary exacerbations, in a patient in need thereof. A patient in need of such treatment can, for example, be a patient suffering from a respiratory disease characterized by the occurrence of pulmonary exacerbations. Respiratory diseases include diseases associated with a pathological condition of the upper respiratory tract, bronchi, bronchioles, alveoli, pleura, and/or pleural cavity. Non-limiting examples of respiratory diseases characterized by pulmonary exacerbations include cystic fibrosis, chronic obstructive pulmonary disease (COPD), bronchiectasis, and interstitial lung disease. In certain specific embodiments, the patient is suffering from cystic fibrosis. In certain other embodiments, the patient is suffering from bronchiectasis, including forms of non-cystic fibrosis bronchiectasis such as, but not limited to, primary ciliary dyskinesia or idiopathic bronchiectasis. In yet additional aspects, the patient is suffering from COPD. In further aspects, the patient is suffering from interstitial lung disease.

In the Phase IIb study described herein, acebilustat treatment was shown to reduce pulmonary exacerbations in cystic fibrosis patients of the mild lung disease phenotype (e.g., having an $FEV_1pp$ greater than about 65% at baseline) as compared to a matched population taking placebo and as compared to that in acebilustat-treated patients with more severe lung disease. Patients having "mild lung disease phenotype" can also be described as being of the mild lung disease subpopulation of CF patients. The terms "mild lung disease phenotype," "mild CF disease," "mild CF," and "mild disease" in reference to CF patients, are used interchangeably herein. The terms "$FEV_1pp$" and "ppFEV1", used interchangeably, refer to forced expiratory volume in one (1) second percent predicted and can be measured using spirometry. The severity of lung disease in cystic fibrosis patients is routinely classified according to $FEV_1pp$ values. For example, in the literature, mild lung disease is classified as FEV1pp≥70%, moderate lung disease is classified as having a FEV1pp between 40 and 69%, and severe lung disease as having a FEV1pp of less than 40% (Cystic Fibrosis Patient Registry. 2016. Cystic Fibrosis Foundation. Available on request from https://www.cfforg/Research/Researcher-Resources/Tools-and-Resources/Patient-Registry-Data-Requests/; Davies et al, (2009), Respiratory Care 54(5): 606-617). The severity of lung disease has also been classified as follows in the literature: mild disease is classified as FEV1≥70% predicted; moderate disease is classified as having FEV1 60-69% predicted; moderately severe lung disease is classified have a FEV1 50-59% predicted; and severe lung disease is classified as having FEV1 35-49% predicted; and very severe lung disease is classified as having an FEV1<35% predicted. (Morrow et al. (2008), Jornal de Pediatria 84(5): 403-409). In the clinical study described herein, the median FEV1pp for the study population was 68% at baseline and it was observed that acebilustat-treated patients with a FEV1pp greater than the median experienced a reduced rate of pulmonary exacerbations and an increase in the time to first pulmonary exacerbation. It was also observed that acebilustat-treated patients with a baseline FEV1pp greater than 65% experienced a reduced rate of pulmonary exacerbations and an increase in the time to first pulmonary exacerbation (see Table 1 below).

As used herein, a CF patient of the mild lung disease phenotype has a baseline $FEV_1pp$ greater than or equal to about 65%. A patient of the mild lung disease phenotype can, for example, have a baseline $FEV_1pp$ greater than or equal to about 68%, a baseline $FEV_1pp$ greater than or equal to about 70%, or a baseline FEV1pp greater than or equal to about 75%. Therefore, in certain aspects, the method comprises treating a patient having a $FEV_1pp$ greater than or equal to about 65% at baseline with acebilustat at a dose of about 100 mg or less, or about 50 mg or less; for example, a daily dose of about 100 mg or a daily dose of about 50 mg. In certain aspects, the patient has a baseline $FEV_1pp$ greater than or equal to about 68%, greater than or equal to about 70%, or greater than or equal to about 75% at baseline. In certain additional aspects, the patient can have a $FEV_1pp$ greater than about 70%, or greater than about 75% at baseline. The inventive methods can also include measuring baseline $FEV_1pp$ in a patient (at baseline or prior to initiating treatment), for example by spirometry, and administering acebilustat to the patient if the patient has an $FEV_1pp$ greater than or equal to about 65%, greater than or equal to about 68%, or greater than or equal to about 70%, or greater than or equal to about 75%. A $FEV_1pp$ at baseline is the $FEV_1pp$ measured pre-treatment, for example, at a point in time prior to or shortly prior to the first administration of acebilustat, or in other words, prior to the initiation of acebilustat treatment, or is the $FEV_1pp$ at the start or initiation of treatment.

Acebilustat can be administered to a patient, such as a cystic fibrosis patient (regardless of disease phenotype), on top of their current treatment regime, or on top of the standard of care. The standard of care for the treatment of cystic fibrosis patients includes, but is not limited to, mucolytics, antibiotics, and CFTR modulators, or a combination thereof. The standard of care for the treatment of chronic obstructive pulmonary disease (COPD) includes, but is not limited to, bronchodilators, beta-agonists, anticholinergics, glucocorticoids, or a combination thereof. The standard of care for the treatment of interstitial lung disease includes, but is not limited to, glucocorticoids, cyclophosphamide, azathioprine, methotrexate, and mycophenolate mofetil, or a combination thereof. The standard of care for the treatment of bronchiectasis includes, but is not limited to, bronchodilators, steroids, and antibiotics such as penicillin antibiotics and inhaled antibiotics including tobramycin and aztreonam, as well as combinations of any of thereof. The additional therapeutic agent(s) that can comprise a patient's treatment regimen are discussed in more detail below. Acebilustat can be administered concomitantly to cystic fibrosis patients with an additional therapeutic agent including, for example, a CFTR modulator and/or a CFTR amplifier. As used herein, the term "CFTR modulator" includes an agent or compound that modulates (for example, increases) the activity of CFTR; in certain specific aspects, the CFTR modulator increases the activity of a CFTR protein. The increase in activity resulting from a CFTR modulator includes, but is not limited to, compounds that correct, potentiate, stabilize and/or amplify CFTR. As such, the term "CFTR modulator" as used herein includes CFTR correctors, CFTR potentiators, CFTR stabilizers, and CFTR amplifiers. A CFTR corrector is an agent or compound that increases the amount of functional CFTR protein to the cell surface, resulting in enhanced ion transport. A CFTR potentiator is an agent or compound that increases the channel activity of CFTR protein located at the cell surface, resulting in enhanced ion transport. A CFTR stabilizer results in an elongated presence of CFTR in the epithelial cell membrane. A CFTR amplifier is an agent that enhances the effect of a CFTR potentiator, corrector, and/or stabilizer. That acebilustat provides a benefit when used in combination with a CFTR modulator is important given the number of cystic fibrosis patients currently treated with CFTR modulators and the likelihood of an increase in number of cystic fibrosis patients who are eligible to be treated with new CFTR modulators over the coming years.

Concomitant treatment or administration of acebilustat and a CFTR modulator, including, but not limited to, CFTR potentiator and/or CFTR corrector, or any other additional therapeutic agent, is intended to mean administration of acebilustat and the additional therapeutic agent at such time that both will have a therapeutic effect and/or co-administration of the agents, for example, as part of the same treatment regimen. Such concomitant administration can involve concurrent (i.e., at the same time), prior, or subsequent administration of acebilustat with respect to the administration of the additional therapeutic agent. For example, the initiation of acebilustat treatment can be subsequent to the initiation of treatment with a CFTR modulator such as a CFTR corrector and/or CFTR potentiator; for example, the patient can have undergone treatment with the CFTR modulator for several weeks, months, or years, prior to initiating treatment with acebilustat. It is to be understood that when acebilustat is co-administered with the at least one additional therapeutic agent (e.g., a CFTR potentiator and/or a CFTR corrector and/or other therapeutic agent), the compound can be administered simultaneously with, prior to, or after administration of one or more other therapeutic agents. Such combination therapy includes administration of a single pharmaceutical dosage formulation which contains the acebilustat and the one or more additional active agents, as well as administration of the acebilustat and each active agent in its own separate pharmaceutical dosage formulation. For example, the acebilustat and the other therapeutic agent can be administered to the patient together in a single oral dosage composition such as a tablet or capsule, or each agent can be administered in separate oral dosage formulations. Where separate dosage formulations are used, acebilustat and one or more additional active agents can be administered at essentially the same time, i.e., concurrently, or at separately staggered times, i.e., sequentially; and/or in the same treatment session and/or as part of the same treatment regimen; and/or daily administration of acebilustat and daily administration of the one or more additional active agents. Combination therapy and concomitant administration is understood to include all these regimens.

As described in more detail below, the Phase IIb study was designed in order to provide the first proof-of-concept for an anti-inflammatory therapy (acebilustat) designed to prevent or reduce progressive loss of lung function by reducing pulmonary exacerbations in cystic fibrosis (CF) patients. The primary analysis was based upon an analysis of variance (ANOVA) in which the average of the Week 48 change from baseline in $FEV_1pp$ for the two acebilustat doses was compared to that in the placebo group. The ANOVA model contained a separate term for each dose group with the average over the two acebilustat doses created by averaging the parameter estimates from the ANOVA model. In addition to terms for treatment group, the ANOVA included stratification for the factors used for randomization. For example, stratified factors include baseline lung function, frequency of pulmonary exacerbations in the prior year, and concomitant CFTR modulator use. The analysis for difference in pulmonary exacerbations may include contrast analyses using confidence intervals, t-test of simple means, Poisson regression and, most preferably, negative binomial regression.

In addition, it was believed that certain subsets of the general cystic fibrosis (CF) population are at greater risk for rapid lung function decline, and that this subset can provide a study population that is affected by active inflammation, and that also experiences a decline of adequate magnitude to detect clinical benefit over a 48-week interval. Such a subset was identified through research of the Cystic Fibrosis Patient Registry (CFPR) and based on knowledge of the projected rate of decline of $FEV_1pp$ and the frequency of pulmonary exacerbations in this subpopulation. For example, prior pulmonary exacerbations are one of the strongest predictors of a future pulmonary exacerbation [Block et al., 2006; VanDevanter et al., 2016]. Furthermore, it has been estimated that up to half of lung function decline is related to pulmonary exacerbations [Waters et al., 2012] and that exacerbations are a clear indicator of active neutrophil driven inflammation (see for example, Ngan et al. (2012), BMC Pulmonary Medicine 12:3; Wojewodka et al. (2014), PLOS One 9(2), e88567). Susceptibility to annual decline in lung function is greatest from adolescence to early adulthood and attenuates after patients reach approximately 30 years of age [Liou et al., 2010]. Additionally, patients with a higher baseline lung function may also be more susceptible to greater declines in $FEV_1pp$ [Konstan et al., 2012]. Additionally, CF patients 15 to 30 years of age are more likely to experience pulmonary exacerbations [CFF Registry Report, 2017].

Based on these published observations, data from the CFPR [Cystic Fibrosis Foundation, 2014] was analyzed for different age ranges (12-17 years, 18-30 years, 31-35 years, or 36-39 years); baseline $FEV_1pp$ (50-59%, 60-79%, 80-99%, or ≥100%) and number of pulmonary exacerbations requiring use of an IV antibiotic in the prior year (0 or ≥1). The registry data provided support for the concept that patients 12-30 years old who had had at least one pulmonary exacerbation in the prior year were at highest risk for rapid lung function decline. Within this subgroup, the registry data provided further evidence that patients with a higher $FEV_1pp$ at baseline were likely to have the most rapid decline in $FEV_1pp$. Within the subgroup of 18-30 years' old, CF patients who had had at least one pulmonary exacerbation in the prior year, the present year rate of decline is estimated to be 3.47 percentage points per year. Detection of differences in rate of $FEV_1pp$ decline on the order of 3 percentage points per year requires observation over at least 48 weeks. Thus, the patient population for the current study was enriched based on optimal patient age, $FEV_1pp$ and exacerbation history, in order to detect a change in rate of $FEV_1$ decline and change in exacerbation rate over 48 weeks in a Phase II study as compared to placebo. This population and study duration is in line with published guidance from the Cystic Fibrosis Foundation (CFF). [Torphy et al., 2015]. Thus, patients for the Phase IIb study were selected based on stringent inclusion criteria (age 18-30 years, $FEV_1pp \geq 50$, and at least one exacerbation in the past year). This enriched the study population with patients who are most susceptible to pulmonary exacerbations and annual lung function decline. It is also believed that this population of patients will achieve greater benefit from acebilustat treatment with respect to decreased lung function decline than other populations.

As discussed above, it was believed that patients most likely to benefit from acebilustat treatment, including combination treatment with a CFTR potentiator and/or CFTR corrector, include patients that are ≤30 years old (for example, between about 12 to about 30 years old), and/or patients that had at least one pulmonary exacerbation in the year prior to the first administration of acebilustat and/or patients that have a $FEV_1pp \geq$ about 50%, as described in more detail below.

The results of the study are shown in FIGS. 3 to 21 and described in the Example. It was found that the major effect of acebilustat was a reduction in the rate of pulmonary exacerbations (PEx) as compared to place and reduced risk of progression to pulmonary exacerbations. These benefits were most notable for patients of the mild disease phenotype (for example, FEV1pp greater than 75 at baseline) as well as in patients taking CFTR modulator therapy. Patients with less severe impairment of lung function or having a mild lung disease phenotype (specifically, FEV1pp greater than 75) achieved the largest benefit from acebilustat therapy in the analysis of data from the combined 50 mg and 100 mg dose groups compared to placebo, achieving about 35% reduction in PEx rate (48% reduction for the 100 mg dose) versus placebo, about 43% reduction in risk of experiencing their first exacerbation (48% reduction in risk for the 100 mg dose) versus placebo and an about 96% higher proportion patients who were exacerbation free after 48 weeks of treatment (100% higher for the 100 mg dose). Furthermore, patients concomitantly treated with CFTR modulator therapy and acebilustat regardless of disease severity phenotype exhibited a clinically meaningful about 20% reduction in rate of PEx (14% reduction for the 100 mg dose), about 29% increased time to first exacerbation (27% increase for the 100 mg dose) and about 47% higher proportion of patients with no exacerbations compared to patients treated with CFTR modulators and placebo (51% higher for the 100 mg dose). In addition, for patients off CFTR modulator therapy, about 15% higher percentage of patients that were exacerbation free was observed. Furthermore, patients with an FEV1pp greater than 75 and treated concomitantly with CFTR modulator therapy exhibited a 54% decrease in the rate of pulmonary exacerbations (65% reduction for the 100 mg dose) and a 165% higher proportion of patients who were exacerbation free at 48 weeks as compared to patients that were treated with placebo instead of acebilustat.

A pulmonary exacerbation for the purposes of the clinical trial is defined as the requirement for oral, inhaled or intravenous antibiotics for four or more signs or symptoms according to the modified Fuchs' criteria (change in sputum; new or increased hemoptysis; increased cough; increased dyspnea; malaise, fatigue or lethargy; temperature>38° C.; anorexia or weight loss; sinus pain or tenderness; change in sinus discharge; change in physical examination of the chest; ≥10% absolute decrease in $FEV_1pp$ from the previously recorded value; radiographic changes indicative of pulmonary infection) [Fuchs et al., 1994], referred collectively (antibiotics plus the four or more signs and symptoms) as expanded Fuchs criteria. A pulmonary exacerbation can be defined according to the Fuchs criteria, the expanded Fuchs criteria, or by other criteria known in the art (including, for example, need for additional treatment as indicated by a recent change in clinical parameters) and/or according to the judgement or determination of a physician [Bilton et al. (2011), Journal of Cystic Fibrosis 10 (Suppl 2): S79-S81; Dakin et al. (2001), Pediatr Pulmonol. 31: 436-442, the contents of each of which are expressly incorporated by reference herein]. Pulmonary exacerbations are typically accompanied by the subsequent treatment of the CF or other respiratory disease patient with a course of antibiotics. For the purposes of a clinical trial and the methods described herein, the date the pulmonary exacerbation began can be defined as the first day of antibiotic use or as the date of the onset of symptoms.

In certain aspects, the method comprises identifying a cystic fibrosis patient that has had at least one pulmonary exacerbation in the prior year (in other words, in the about twelve month period or about 52 week period prior to the initiation of treatment) and treating such a patient with acebilustat at total oral daily dose of about 50 mg to about 100 mg, or about 100 mg or less, or about 50 mg or less, or about 100 mg, or about 50 mg. The method can also include identifying a cystic fibrosis patient that has had at least one pulmonary exacerbation in the prior year, and treating such a patient with acebilustat at a total oral daily dose of about 50 mg to about 100 mg, or about 100 mg or less, or about 50 mg or less, or about 100 mg, or about 50 mg. In addition, the method can include identifying a patient that has had two or more, or more than two pulmonary exacerbations in the prior year, and treating such a patient with acebilustat at a total oral daily dose of about 50 mg to about 100 mg, or about 100 mg or less, or about 50 mg or less, or about 100 mg, or about 50 mg. In certain additional aspects, the method comprises identifying a cystic fibrosis patient that has had at least one pulmonary exacerbations within the past two years, within the past three years, within the past four years, or within the past five years, and treating such a patient with acebilustat at a total oral daily dose of about 50 mg to about 100 mg, or about 100 mg or less, or about 50 mg or less, or about 100 mg, or about 50 mg. The methods include identifying a cystic fibrosis patient that has had at least one pulmonary exacerbation, two or more pulmonary exacerbations, or more than two pulmonary exacerbations, within the prior year, the past two years, within the past three years, within the past four years, or within the past five years, and treating such a patient with acebilustat at a total oral daily dose of about 50 mg to about 100 mg, or about 100 mg or less, or about 50 mg or less, or about 100 mg, or about 50 mg.

The Phase 2b study includes stratification based on concomitant CFTR modulator use. This is important since about half of cystic fibrosis patients in the U.S. are currently treated with CFTR modulators. Stratification based on concomitant CFTR modulator use was also considered important as neutrophil elastase is shown to downregulate CFTR [Le Gars et al., 2013]; and it was believed that acebilustat, which has been shown to reduce neutrophil elastase [Elborn et al., 2017], may have synergistic effects with CFTR modulators, including CFTR potentiators and/or CFTR correctors.

The methods include orally administering to a cystic fibrosis patient acebilustat at a total daily dose of about 100 mg or less, of about 50 mg or less, or from about 50 mg to about 100 mg, or a total daily dose of about 100 mg, or a total daily dose of about 50 mg. As described herein, the patient treated with acebilustat can be undergoing concomitant CFTR modulator therapy (regardless of lung disease phenotype) wherein a therapeutically effective amount of a CFTR potentiator and/or a CFTR corrector is concomitantly administered to said patient. A preferred CFTR potentiator is ivacaftor (KALYDECO®). Preferred CFTR correctors are lumacaftor and tezacaftor. In certain aspects, one CFTR potentiator and at least one CFTR corrector are administered. For example, a combination including ivacaftor can be administered; for example, a combination of ivacaftor and lumacaftor, preferably ORKAMBI® (lumacaftor/ivacaftor) is administered. The method includes administering at least two CFTR correctors, or at least one CFTR corrector and at least one CFTR potentiator. For example, a combination of ivacaftor and lumacaftor, preferably ORKAMBI® (lumacaftor/ivacaftor) can be administered. In other examples, two CFTR correctors can be administered, optionally with a CFTR potentiator; the combination can, for example, include ivacaftor. As described above, acebilustat can, for example, be administered at a dose of about 50 mg every 12 or 24 hours (or once or twice a day), or at a dose of about 100 mg every 24 hours (or once a day). Acebilustat can also be administered at a total daily dose of 50 mg or less, wherein acebilustat is administered once or multiple times a day. When the treatment includes administration of ivacaftor, an exemplary oral dose is 150 mg every 12 hours (or twice a day) and/or at a total daily dose of about 300 mg. For patients aged 2 to 6 years old, an exemplary oral dose of ivacaftor is 50 mg or 75 mg twice a day. When the treatment includes administration of lumacaftor/ivacaftor (as a combination, for example, ORKAMBI®), the total daily dose of lumacaftor administered is about 800 mg and the total daily dose of ivacaftor administered is about 500 mg for patients aged 12 years and over. For patients between the ages of 6 and 11 treated with ORKAMBI®, the total daily dose of lumacaftor administered is 400 mg and the total daily dose of ivacaftor administered is about 500 mg. Certain triple combination regimens comprising ivacaftor, such as ivacaftor, tezacaftor, and another corrector have also been described for the treatment of cystic fibrosis. Thus, the invention encompasses administration of acebilustat, as described herein, in combination with a triple combination regimen; optionally, wherein the triple combination regimen comprises ivacaftor. In certain embodiments, the invention is directed to a method comprising administering acebilustat and a triple combination regimen, for example, such a triple combination can include tezacaftor plus ivacaftor and one of the following: VX-445, VX-659, VX-440 or VX-152. In other embodiments the triple combination can be comprised of other CFTR modulators. In yet other embodiments the combination may be comprised of four or more such CFTR modulators.

Cystic fibrosis is caused by loss-of-function mutation(s) in the cystic fibrosis membrane conductance regulator (CFTR) gene. CFTR is a membrane protein and chloride channel. There are more than 1,800 mutations that have been discovered in the CFTR gene, which are characterized into five classes. The most often occurring mutation is F508del (deletion of phenylalanine at position 508), a Class II mutation, in which the CFTR protein does not reach the cell surface due to misfolding. As will be understood, a person can have a F508del mutation on one allele and other mutation on the other allele (heterozygous), or on both alleles (homozygous). Other mutations include Class III mutations, such as G551D and S549N, where CFTR reaches the cell surface but the channel has compromised function. The patient to be treated according to the described methods can, for example, have a F508del mutation (either heterozygous or homozygous), and/or have a CFTR functional mutation (Classes III-VI or III to VI, depending on the classification system used), or have a non-F508del mutation. Exemplary mutations in addition to F508del are E56K, P67L, R74W, D110E, D110H, R117C, R117H, E193K, L206W, R347H, R352Q, A455E, D579G, S945L, S977F, F1052V, K1060T, A1067T, G1069R, R1070Q, R1070W, F1074L, D1152H, D1270N, G551D, G178R, S549R, S549N, G551S, G1244E, S1251N, S1255P, and G1349D. CFTR correctors increase the amount of functional CFTR protein at the cell surface, resulting in enhanced ion transport. CFTR potentiators are compounds that increase the channel activity of the CFTR on the cell surface (for example, in patients with a gating mutation). CFTR correctors, for example, can target patients with the F508del mutation. The method of treatment can include treating patients with a F508del mutation and treating patients with a non-F508del patient.

In yet additional embodiments, the invention is directed to a method of treating cystic fibrosis or a method of reducing pulmonary inflammation or a method of treating chronic lung inflammation and/or decreasing pulmonary exacerbations in a cystic fibrosis patient in need thereof comprising administering to said patient acebilustat at a total daily dose of about 100 mg or less, or about 50 mg or less, or from about 50 mg to about 100 mg, or about 100 mg, or about 50 mg, wherein said patient is not undergoing concomitant treatment with a CFTR modulator such as a CFTR corrector/ and or CFTR potentiator and/or CFTR amplifier. Such patients include, but are not limited to, patients of the mild lung disease phenotype as described herein. In certain aspects, the patient is not undergoing concomitant treatment with a CFTR corrector. In additional aspects, the patient is not undergoing concomitant treatment a CFTR potentiator. In yet additional aspects, the patient is not undergoing concomitant treatment with either a CFTR corrector or a CFTR potentiator, or a combination thereof. In further aspects, the total daily dose of acebilustat administered to the cystic fibrosis patient not undergoing treatment with a CFTR corrector and/or CFTR potentiator is about 50 mg. In additional aspects, the total daily dose of acebilustat administered to the cystic fibrosis patient not undergoing treatment with a CFTR corrector and/or CFTR potentiator is about 100 mg. In yet additional aspects, the total daily dose of acebilustat administered to the cystic fibrosis patient not undergoing treatment with a CFTR corrector and/or CFTR potentiator is about 50 mg or less. In further aspects, the total daily dose of acebilustat administered to the cystic fibrosis patient not undergoing treatment with a CFTR corrector and/or CFTR potentiator is about 100 mg or less.

In additional aspects, the methods comprise administering acebilustat to a cystic fibrosis patient, wherein the patient is 30 years old or younger. In further aspects, the patient is two years or older, six years or older, 12 years and older, 18 years and older, about six to 12 years old, about 12 to about 30 years old, or about 18 to about 30 years old. In yet additional aspects, the patient is greater than 30 years old. In further aspects, the patient is 18 years or older.

The invention encompasses methods of reducing pulmonary inflammation and/or decreasing pulmonary exacerbations in a cystic fibrosis patient in need thereof comprising administering to the patient a therapeutically effective amount of acebilustat as described herein, wherein the patient is greater than 6 years older, two years or older, six years or older, 12 years or older, 18 years or older, 30 years or older, between about 6 years and 12 years old, between about 6 years old and about 30 years old, between about 12 and about 30 years old, or between about 18 and about 30 years and has had at least one pulmonary exacerbation in the year prior to the first administration of acebilustat. The invention additionally encompasses methods of treating cystic fibrosis, reducing pulmonary inflammation, and/or treating chronic lung inflammation and/or decreasing pulmonary exacerbations in a cystic fibrosis patient in need thereof comprising administering to the patient a therapeutically effective amount of acebilustat as described herein, wherein the patient is six years or older, two years or older, six years or older, 12 years or older, 18 years or older, 30 years or older, between about 6 years and 12 years old, between about 12 to about 30 years old, or between about 18 and about 30 years and has had two or fewer pulmonary exacerbations in the year prior to the first administration of acebilustat. In further aspects, the patient is about six years old or older, two years or older, six years or older, 12 years or older, 18 years or older, 30 years or older, between about 6 years and 12 years old, between about 12 and about 30 years old, or between about 18 and about 30 years old and has a $FEV_1pp$ greater than or equal to about 65%, greater than or equal to about 68%, greater than or equal to about 70%, or greater than or equal to about 75%.

The invention also encompasses methods of reducing pulmonary inflammation and/or decreasing pulmonary exacerbations in a cystic fibrosis patient in need thereof comprising administering to the patient a therapeutically effective amount of acebilustat, wherein the patient is 30 years old or older and has had at least one pulmonary exacerbation in the year prior to the first administration of acebilustat. In certain aspects, the patient is 30 years old or older and has had two or fewer pulmonary exacerbations in the year prior to the first administration of acebilustat. In further aspects, the patient is 30 years old or older and has a $FEV_1pp$ greater than about 65%, greater than to about 68%, greater than about 70%, greater than about 75%, greater than or equal to 65%, greater than or equal to 68%, greater than or equal to about 70%, or greater than or equal to about 75%.

The methods described herein are useful for treating chronic lung inflammation and/or reducing pulmonary inflammation in a cystic fibrosis patient. In certain aspects, chronic lung inflammation is treated and/or pulmonary inflammation is reduced when there is a decrease in the number of pulmonary exacerbations and/or attenuation in the rate of lung function decline. With respect to a decrease in pulmonary exacerbations in CF or other respiratory disease patient, the decrease in pulmonary exacerbations can also be a decrease in the annualized rate of pulmonary exacerbations. In addition, the number of pulmonary exacerbations experienced by the CF or other respiratory disease patient in the six (6), twelve (12), twenty-four (24), thirty-six (36), or forty-eight (48) month period after initiating the treatment (comprising acebilustat) can be decreased as compared to that in the six, twelve, twenty-four, thirty-six, or forty-eight month period, respectively, prior to initiating the treatment. For example, where the patient had experienced two pulmonary exacerbations in the twelve month period prior to initiating the treatment, a reduction in chronic lung inflammation or pulmonary inflammation can be evidenced by a reduction in the number of pulmonary exacerbations (e.g., only one or no pulmonary exacerbations) in the twelve month period after initiating the treatment. In certain aspects, the CF or other respiratory disease patient is exacerbation free for the six (6), twelve (12), twenty-four (24), thirty-six (36), or forty-eight (48) month period after initiating the treatment (comprising acebilustat). In certain specific aspects, the CF patient is exacerbation free for the six (6), twelve (12), twenty-four (24), thirty-six (36), or forty-eight (48) month period after initiating the treatment (comprising acebilustat).

In addition, chronic lung inflammation is treated and/or pulmonary inflammation is reduced when the rate of lung function decline is attenuated after initiating the treatment (comprising acebilustat) as compared to that prior to initiating the treatment.

The acebilustat treatment is "initiated" at the time the first dose of acebilustat is administered; thus, for example, the six month period after initiating the treatment is the six month period from the day or date the first dose of acebilustat is administered and the six month period prior to initiating the treatment is the six month period prior to the day or date the first dose of acebilustat is administered.

As used therein, a "therapeutically effective amount" or an "effective amount" refers to that amount of a compound or drug that, when administered to a mammal, preferably a human, is sufficient to effect treatment, as defined below, of a disease or condition of interest in the mammal, preferably a human. The amount of a compound of the invention which constitutes a "therapeutically effective amount" or an "effective amount" will vary depending on, for example, the activity of the specific compound employed; the metabolic stability and length of action of the compound; the age, body weight, general health, sex, and diet of the patient; the mode and time of administration; the rate of excretion; the drug combination; the severity of the particular disorder or condition; and the subject undergoing therapy, but it can be determined routinely by one of ordinary skill in the art having regard to his own knowledge and to this disclosure.

"Treating" or "treatment" as used herein covers the treatment of the disease or condition of interest in a mammal, preferably a human, having the disease or condition of interest, and includes, for example: (i) inhibiting or decreasing the severity of the disease or condition, or one or more symptoms thereof, i.e., arresting or slowing development or progression of the disease or condition, and/or ameliorating one or more symptoms; (ii) relieving the disease or condition, i.e., causing regression of the disease or condition, or one more symptoms thereof; and/or (iii) stabilizing the disease or condition. In addition, "treating" or "treatment" in the context of cystic fibrosis can include treating chronic lung inflammation and/or decreasing pulmonary inflammation such as by reducing pulmonary exacerbations (for example, reducing the rate, number, or frequency of pulmonary exacerbation or increasing the time to first pulmonary exacerbation), attenuating the decline in lung function, increasing lung function, reducing inflammation (including reducing neutrophil-induced inflammation), reducing neutrophil influx, increasing $FEV_1pp$, and/or slowing the decrease in $FEV_1pp$, or a combination thereof, as described herein. In the context of treating a respiratory disease characterized by pulmonary exacerbations, "treating" or "treatment" can include reducing pulmonary exacerbations (for example, reducing the rate, number, or frequency of pulmonary exacerbation or increasing the time to first pulmonary exacerbation).

As used herein, the terms "disease" and "condition" may be used interchangeably or may be different in that the particular malady or condition may not have a known causative agent (so that etiology has not yet been worked out) and it is therefore not yet recognized as a disease but only as an undesirable condition or syndrome, wherein a more or less specific set of symptoms have been identified by clinicians.

A "pharmaceutical composition" refers to a formulation of a compound described herein, for example, acebilustat and/or a CFTR modulator, and a medium generally accepted in the art for the delivery of the biologically active compound to mammals, for example, humans. Such a medium includes all pharmaceutically acceptable carriers, diluents or excipients.

"Optional" or "optionally" means that the subsequently described event of circumstances may or may not occur, and that the description includes instances where said event or circumstance occurs and instances in which it does not.

"Pharmaceutically acceptable excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which, for example, has been approved by the United States Food and Drug Administration as being acceptable for use in humans or domestic animals.

Administration of the compounds or drugs described herein encompasses administration of a pharmaceutically acceptable salt of said compound or drug, for example, administration of a pharmaceutically acceptable salt of acebilustat or a pharmaceutically acceptable salt of a CFTR modulator. Administration of the compounds or drugs as described herein (such as acebilustat, a CFTR modulator or other additional therapeutic agent), or their pharmaceutically acceptable salts, in pure form or in an appropriate pharmaceutical composition, can be carried out via any of the accepted modes of administration of agents for serving similar utilities. As described herein, the preferred mode of administration for acebilustat is oral administration. The pharmaceutical compositions described herein can be prepared by combining a compound or drug with an appropriate pharmaceutically acceptable carrier, diluent or excipient, and may be formulated into preparations in solid, semi-solid, liquid or gaseous forms, such as tablets, capsules, powders, granules, ointments, solutions, suppositories, injections, inhalants, gels, microspheres, and aerosols. Typical routes of administering such pharmaceutical compositions include, without limitation, oral, topical, transdermal, inhalation, parenteral, sublingual, rectal, vaginal, and intranasal. The term parenteral as used herein includes subcutaneous injections, intravenous, intramuscular, intrasternal injection or infusion techniques. Pharmaceutical compositions of the invention are formulated so as to allow the active ingredients contained therein to be bioavailable upon administration of the composition to a patient. Compositions that will be administered to a subject or patient take the form of one or more dosage units, where for example, a tablet may be a single dosage unit, and a container of a compound of the invention in aerosol form may hold a plurality of dosage units. Actual methods of preparing such dosage forms are known, or will be apparent, to those skilled in this art; for example, see The Science and Practice of Pharmacy, $20^{th}$ Edition (Philadelphia College of Pharmacy and Science, 2000). The composition to be administered will, in any event, contain a therapeutically effective amount of the compound or drug, or a pharmaceutically acceptable salt thereof, for treatment of a disease or condition of interest in accordance with the teachings of this invention.

A pharmaceutical composition can be in the form of a solid or liquid. In one aspect, the carrier(s) are particulate, so that the compositions are, for example, in tablet or powder form. In one aspect, the composition can be an encapsulated powder or granular form. In another aspect, an encapsulated powder or granular formulation can be opened and sprinkled in food or administered by gastric intubation. The carrier(s) can be liquid, with the compositions being, for example, an oral syrup, injectable liquid or an aerosol, which is useful in, for example, inhalatory administration. When intended for oral administration, the pharmaceutical composition can be in either solid or liquid form, where semi-solid, semi-liquid, suspension and gel forms are included within the forms considered herein as either solid or liquid.

As a solid composition for oral administration, the pharmaceutical composition may be formulated into a powder, granule, compressed tablet, pill, capsule, chewing gum, wafer or the like form. Such a solid composition will typically contain one or more inert diluents or edible carriers. In addition, one or more of the following may be present: binders such as carboxymethylcellulose, ethyl cellulose, microcrystalline cellulose, gum tragacanth or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin; a flavoring agent such as peppermint, methyl salicylate or orange flavoring; and a coloring agent.

When the pharmaceutical composition is in the form of a capsule, for example, a gelatin capsule, it may contain, in addition to materials of the above type, a liquid carrier such as polyethylene glycol or oil.

The pharmaceutical composition can be in the form of a liquid, for example, an elixir, syrup, solution, emulsion or suspension. The liquid can be for oral administration or for delivery by injection, as two examples. When intended for oral administration, a composition can contain, in addition to the present compounds, one or more of a sweetening agent, preservatives, dye/colorant and flavor enhancer. In a composition intended to be administered by injection, one or more of a surfactant, preservative, wetting agent, dispersing agent, suspending agent, buffer, stabilizer and isotonic agent may be included.

The liquid pharmaceutical compositions of the invention, whether solutions, suspensions or other like form, can include one or more of the following adjuvants: sterile diluents such as water for injection, saline solution, preferably physiological saline, Ringer's solution, isotonic sodium chloride or physiological saline, fixed oils such as synthetic mono or diglycerides which may serve as the solvent or suspending medium, polyethylene glycols, glycerin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parenteral preparation can be enclosed in ampoules, disposable syringes or multiple dose vials made of glass or plastic. Physiological saline is a preferred adjuvant. An injectable pharmaceutical composition is preferably sterile.

The invention includes methods wherein acebilustat is administered with an additional therapeutic agent, for example, that is part of the standard of care for the respiratory disease suffered by the patient, including, for example, cystic fibrosis, chronic obstructive pulmonary disease, bronchiectasis, and interstitial lung disease. The invention specifically encompasses methods wherein acebilustat is administered with an additional therapeutic agent (for example, that is part of the standard of care for cystic fibrosis), or the combination of acebilustat and a CFTR potentiator and/or CFTR corrector is co-administered with an additional therapeutic agent. The additional therapeutic agent can, for example, be a drug used in the treatment of cystic fibrosis can include, but is not limited to, a bronchodilator, an antibiotic, a mucolytic, a surfactant, a pancreatic enzyme replacement drug, a CFTR modulator, or a combination thereof. In further aspects, the invention encompasses methods wherein acebilustat or the combination of acebilustat and a CFTR modulator such as CFTR potentiator and/or CFTR corrector is combined with an airway clearance technique. Such airway clearance techniques include coughing or huffing and can include percussion (clapping) or vibration. In additional aspects, acebilustat or the combination acebilustat and a CFTR modulator, such as CFTR potentiator and/or CFTR corrector, is combined with gene therapy (including the administration of agents used for gene therapy, such as, retroviral vectors or genome editing reagents) and gene editing techniques such as those which use the CRISPR/Cas9 system.

In some embodiments, the additional therapeutic agent used in the treatment of CF or other respiratory disease is a beta-agonist. Exemplary beta-agonists are albuterol, salbutamol, levalbuterol, formoterol, fenoterol, salmeterol, bambuterol, brocaterol, clenbuterol, terbutalin, tulobuterol, epinephrin, isoprenalin, and hexoprenalin. In another embodiment, the yet additional therapeutic agent is an anticholinergic agent. Exemplary anticholinergics are tiotropium, oxitropium, ipratropium, and glycopyrrolate. In a further embodiment, the additional therapeutic agent is a mucolytic and/or a surfactant. Exemplary mucolytics and surfactants are saline, acetylcystein, ambroxol, carbocystein, tyloxapol, dipalmytoylphosphatidylcholin, recombinant surfactant proteins, and DNase. In one embodiment, the yet additional therapeutic agent is an antibiotic agent. Exemplary antibiotics are beta-lactam antibiotics, including amoxycillin, piperacillin, cephalosporines, including cefaclor, cefazedon, cefuroxim, cefoxitin, cefodizim, cefsulodin, cefpodixim, and cefixim, carbapenemes such as imipenem and cilastatin, monbactames, such as, aztrenonam, aminoglycosides, including streptomycin, neomycin, paromomycin, kanamycin, gentamycin, amicacin, tobramycin, and spectinomycine, tetracyclines, such as doxycyclin and minocycline, macrolides including erythromycine, clarithromycine, roxithromycine, azithromycin, josamycine, and spiramycine, gyrase inhibitors or quinolones such as ciprofloxacin, ofloxacin, levofloxacine, pefloxacine, lomefloxacine, fleroxacine, clinafloxacine, sitafloxacine, gemifloxacine, balofloxacine, trovafloxacine, and moxifloxacine, sulfonamides and nitroimidazoles including metronidazol, tinidazol), chloramphenicol, lincomycine, clindamycine, and fosfomycine, and glycopeptides such as Vancomycine and Teicoplanine. In yet additional embodiments, the additional therapeutic agent is an anti-inflammatory drug. Exemplary anti-inflammatory drugs include ibuprofen, dornase alfa, BIIL 284, ajulemic acid, a PDE4 inhibitor (e.g., roflumilast), romoglycate and nedocromil. In yet additional aspects, the additional therapeutic agent is azithromycin. In an additional aspect, acebilustat is co-administered with a corticosteroid. Exemplary corticosteroids are beclomethasone, betamethasone, budesonide, ciclesonide, flunisolide, fluticasone, icomethasone, mometasone, rofleponide, and triamcinolone. In yet further aspects, the additional therapeutic agent is bradykinin, prostaglandin, leukotriene and platelet activating factor antagonists. The invention encompasses administration of one or more additional therapeutic agents, or a combination thereof concomitantly with acebilustat. In certain additional aspects, the invention encompasses administration of one or more additional therapeutic agents, or a combination thereof concomitantly with acebilustat to a cystic fibrosis patient.

The invention is illustrated by the following non-limiting examples.

Example 1: EMPIRE-CF: A Phase II Randomized Placebo-Controlled Trial of Once-Daily, Oral Acebilustat in Adult Patients with Cystic Fibrosis—Study Design, Patient Demographics and Results Acebilustat is a novel, synthetic, small-molecule leukotriene A4 hydrolase inhibitor in development as a once-daily oral therapy that modulates LTB4 production and targets the inflammatory process in CF [Elborn et al., 2017a]. In two Phase I trials, acebilustat reduced LTB4 production and other inflammatory markers in healthy volunteers and patients with CF [Elborn et al., 2017a, Elborn et al., 2017b]. Based on these promising data, a Phase IIb study, EMPIRE CF (Evaluation of the modulation of the pulmonary inflammatory response in CF) was designed and completed to determine the dose, duration and endpoints for future clinical trial(s). The study was the first proof-of-concept for a novel anti-inflammatory therapy designed to show prevention of progressive loss of lung function and/or reduction of pulmonary exacerbations in CF patients. Described below is the study design, rationale, and results. The demographics of the study population are also presented, and their importance to the study outcomes is discussed.

Methods

Design Considerations

Previous short-term trials (12 weeks' treatment or less) have shown that anti-inflammatory medications may not lead to acute changes in forced expiratory volume in one second percent predicted ($FEV_1pp$) or even changes in biomarkers of inflammation, despite the potential for effective therapy [Elborn et al., 2012; Moss et al., 2013; Chmiel et al., 2015]. A longer-term study is more likely to show attenuation in the annual rate of lung function decline, as well as reductions in exacerbations. For example, the four-year high-dose ibuprofen study demonstrated a decreased rate of $FEV_1$ decline in a general CF population, without demonstrating more rapid evidence of benefit. [Konstan et al., 1995]. Such a duration is not feasible for current Phase II trials. On this basis, a treatment period of 48 weeks was considered for the current study, with a larger sample size to detect changes over a shorter period of observation (see section below).

Measuring significant changes in lung function decline and exacerbation frequency is only possible if the correct patient population is enrolled. We hypothesized that certain subsets of the general CF population may be at greater risk for rapid lung function decline, and that this subset may provide a study population that is affected by active inflammation, and that also experiences a decline of adequate magnitude to detect clinical benefit over a 48-week interval. Such a subset was identified through research of the Cystic Fibrosis Patient Registry (CFPR) and based on knowledge of the projected rate of decline of $FEV_1pp$ and the frequency of pulmonary exacerbations in this subpopulation. For example, prior pulmonary exacerbations are one of the strongest predictors of a future pulmonary exacerbation [Block et al., 2006; VanDevanter et al., 2016]. Furthermore, it has been estimated that up to half of lung function decline is related to pulmonary exacerbations [Waters et al., 2012] and that exacerbations are a clear indicator of active neutrophil driven inflammation. Susceptibility to annual decline in lung function is greatest from adolescence to early adulthood and attenuates after patients reach approximately 30 years of age [Liou et al., 2010]. Additionally, patients with a higher baseline lung function may also be more susceptible to greater declines in $FEV_1pp$ [Konstan et al., 2012].

Based on these published observations, data from the CFPR (Cystic Fibrosis Foundation, 2014) were analyzed for different age ranges (12-17 years, 18-30 years, 31-35 years, or 36-39 years); baseline $FEV_1pp$ (50-59%, 60-79%, 80-99%, or ≥100%) and number of pulmonary exacerbations requiring use of an IV antibiotic in the prior year (0 or ≥1). The registry data provided strong support for the concept that patients 12-30 years old who had had at least one pulmonary exacerbation in the prior year were at highest risk for rapid lung function decline. Within this subgroup, the registry data provided further evidence that patients with a higher $FEV_1pp$ at baseline were likely to have the most rapid decline in $FEV_1pp$. Within the subgroup of 18-30 years' old CF patients who had had at least one pulmonary exacerbation in the prior year, the present year rate of decline is estimated to be 3.47 percentage points per year. Detection of differences in rate of $FEV_1pp$ decline versus placebo on the order of 3 percentage points per year requires observation over at least 48 weeks. Thus, the patient population for the current study was enriched based on optimal patient age, $FEV_1pp$ and exacerbation history, in order to detect versus placebo a difference in rate of $FEV_1$ decline and difference in exacerbation rate over 48 weeks in a Phase II study (see section 2.4). This population and study duration is in line with published guidance from the Cystic Fibrosis Foundation (CFF) [Torphy et al., 2015].

This Phase II study was used as an important test of the study design while also establishing proof of concept that leukotriene A4 hydrolase (LTA4H) is a therapeutic target in CF. A priori baseline stratification based on lung function (as $FEV_1pp$), number of exacerbations in the prior year, and concomitant CFTR modulator use ensured that patient characteristics were balanced between treatment arms to allow identification of the optimal patient population for future trials. The inclusion of CFTR modulator use as a stratification criterion is also important given the evolving standard of care, which may soon include use of a CFTR modulator regimen across a broad spectrum of the CF population.

Overall Study Design

Figure 2:
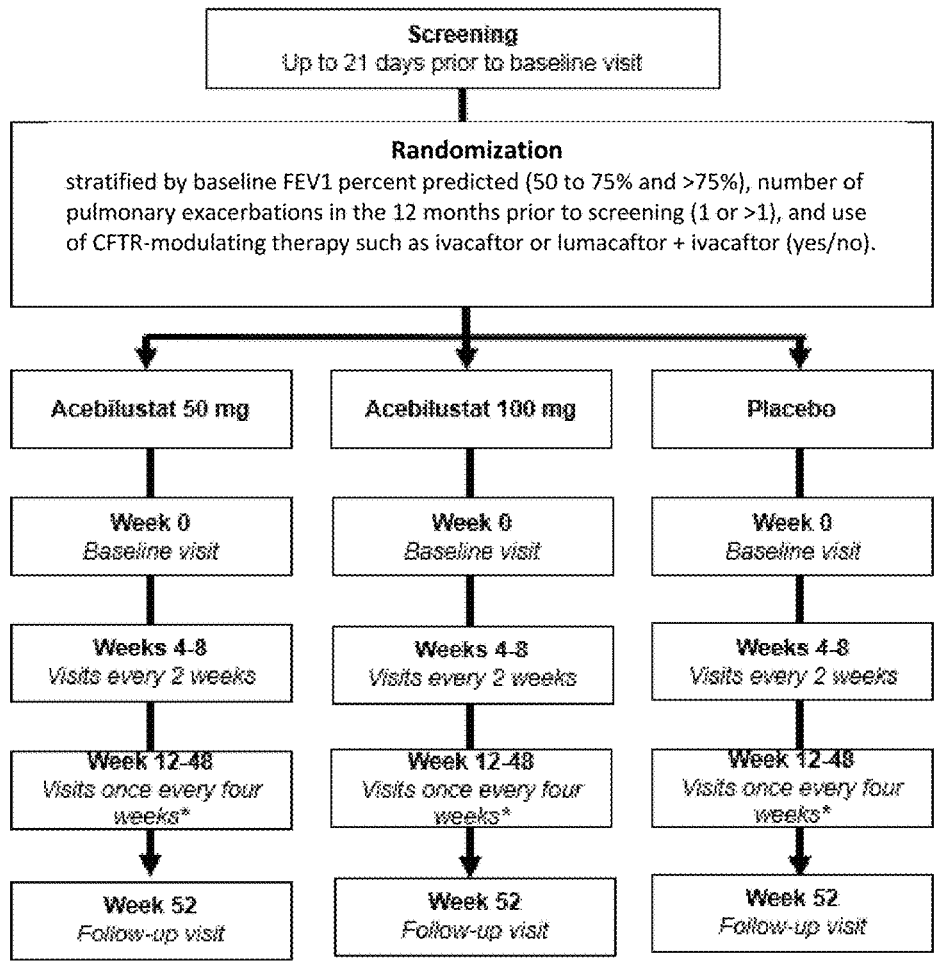
FIG. 2 is a flow chart showing the Phase IIb study design. Randomization was stratified by baseline FEV1 percent predicted (50 to 75% and >75%), number of pulmonary exacerbations in the 12 months prior to screening (1 or >1) and use of CFTR-modulating therapy such as ivacaftor or lumacaftor and ivacaftor (yes/no).

EMPIRE-CF was a Phase II multicenter, randomized, double-blind, placebo-controlled, parallel-group study to evaluate the efficacy and safety of acebilustat in adult patients with CF (NCT02443688). The study consisted of a 48-week treatment period and follow-up visit 4 weeks after treatment completion. Screening visits occurred up to 21 days prior to the first study drug dose (FIG. 2).

Patients

Patients were enrolled from 69 centers in the USA, Canada, and Europe. All centers were experienced in CF care and the conduct of clinical trials. Inclusion and exclusion criteria are shown in Table 2. In brief, adult women and men 18-30 years old with a documented diagnosis of CF, an $FEV_1pp≥50\%$ at screening and at least one pulmonary exacerbation in the previous year were enrolled. Baseline demographics are presented in the section below.

Altogether, 284 patients were screened, 200 patients enrolled, and 199 patients (the FAP) received at least one dose of study drug (acebilustat 100 mg, n=66; acebilustat 50 mg, n=67; placebo, n=66); one patient in the placebo group was randomized but discontinued before receiving the study drug. Overall, 32 patients (16%) discontinued the study before the Week 48 visit, including 21 (15.8%) from the acebilustat treatment groups and 11 (16.7%) from the placebo group. The most common reasons for discontinuation were withdrawal of informed consent (5%) and noncompliance with study drug (3%). The per-protocol (PP) analysis included 162 patients (acebilustat 100 mg, n=54; acebilustat 50 mg, n=54; placebo, n=54). Mean compliance with study drug was 93% in the acebilustat 100 mg group, 96% in the acebilustat 50 mg group, and 96% in the placebo group.

Interventions Patients were randomized 1:1:1 to receive either once-daily oral acebilustat 50 mg or 100 mg (Celtaxsys, Atlanta, Ga., USA), or placebo supplied as capsules. The two acebilustat doses were selected based on the levels of reduction of serum LTB4 production seen in Phase I studies. The 100 mg dose resulted in near-maximum LTB4 reduction (86% reduction) whilst the 50 mg dose showed a peak reduction in LTB4 production of ~75% [Elborn et al., 2017b].

Outcomes

The primary endpoints were absolute change from baseline in $FEV_1pp$ and safety outcomes. Secondary endpoints included rate of pulmonary exacerbations and time to first pulmonary exacerbation, and the effects on biomarkers of lung and systemic inflammation. Analyses are described in section entitled "Analysis."

Pulmonary exacerbations were defined as the requirement for oral, inhaled or intravenous antibiotics for four or more signs or symptoms according to the modified Fuch's criteria (change in sputum; new or increased hemoptysis; increased cough; increased dyspnea; malaise, fatigue or lethargy; temperature>38° C.; anorexia or weight loss; sinus pain or tenderness; change in sinus discharge; change in physical examination of the chest; ≥10% absolute decrease in $FEV_1pp$ from the previously recorded value; radiographic changes indicative of pulmonary infection) [Fuchs et al., 1994], referred collectively (antibiotics plus the four or more signs and symptoms) as expanded Fuchs criteria. The date the pulmonary exacerbation began was defined as the first day of antibiotic use.

Assessments

Patient Medical Status

At the screening visit, investigators recorded a full medical history and performed a complete physical examination and laboratory tests to determine eligibility for the study. At the screening visit, demographics and disease characteristics, concomitant CF medications (including use of CFTR modulators such as ivacaftor or lumacaftor, use of dornase alfa and chronic azithromycin), history of *Pseudomonas*

*aeruginosa* colonization and CFTR genotype were recorded. The number of pulmonary exacerbations in the last 12 months and the date of last pulmonary exacerbation were also recorded at screening.

Spirometry

Spirometry data were recorded at screening and baseline; all other spirometric measurements at subsequent visits are ideally recorded within ±1 h of the baseline visit measurement. All tests met American Thoracic Society/European Respiratory Society criteria for quality (acceptability, reproducibility, and end of test criteria) [Miller et al., 2005]. To ensure consistency of measurement, spirometry measurements were ideally performed by the same researcher and the patient coached to use maximum effort at every attempt. Patients were able to take all of their concomitant medications according to their regular schedule; however, they were to refrain from using short-acting bronchodilators within 4 h of the scheduled spirometry time, and long-acting bronchodilators within 12-24 h of the scheduled spirometry time.

Safety

Treatment-emergent adverse events (TEAEs), including serious adverse events, were collected at each visit, and summarized by MEDRA system organ class and preferred term, severity, and relatedness to the study drug. An independent data monitoring committee monitored the safety and study conduct at approximately 8-week intervals.

Treatment Adherence

Assessments of adherence to treatment with the study drug were based on a capsule count by investigators at visits 3, 5-9, 11, 13, and 15. Patients were asked whether any capsules had been lost or destroyed to ensure accuracy of the adherence assessment.

Sample Size Determination

It was assumed that a sample size of 156 patients in the full analysis population (FAP, n=52 acebilustat 50 mg: n=52 acebilustat 100 mg: n=52 placebo) would be required for the primary endpoint. However, to ensure an adequate sample size for a per-protocol (PP) analysis (based on 80% of patients being included in the PP population), the number of randomized patients in the FAP was 195, i.e. n=65 in each treatment arm.

Sample size calculations were based on the primary efficacy endpoint of an absolute change from baseline in $FEV_1pp$. Assumptions in the calculation are that: there is a 1:1:1 ratio of patients receiving 50 mg acebilustat vs 100 mg acebilustat vs placebo; the difference in average treatment effect for active treatment (both doses of acebilustat) vs placebo is at least 3.5 units at 48 weeks. With a standard deviation of 7 units the study had a power of at least 90% with one-sided alpha of 0.05 to detect the difference in average treatment effect (change from baseline in $FEV_1pp$) for active treatment (both doses of acebilustat) vs placebo of 3.5 units at 48 weeks.

Randomization and Blinding

Eligible patients were randomized to active treatment by an interactive web-based randomization system (IWRS). Randomization was stratified by baseline $FEV_1pp$ (50 to 75% and >75%), number of pulmonary exacerbations in the 12 months before screening (1 or >1) and use of CFTR-modulating therapy ivacaftor or ivacaftor+lumacaftor (yes/no). All patients, investigators and others in direct contact with patients were blinded to treatment assignment as were the sponsor and contract research organization staff.

Analysis

Primary Endpoint

The primary analysis was based upon an analysis of variance (ANOVA) in which the average of the Week 48 change from baseline in $FEV_1pp$ for the two acebilustat doses was compared to that in the placebo group. The ANOVA model contained a separate term for each dose group with the average over the two acebilustat doses created by averaging the parameter estimates from the ANOVA model. In addition to terms for treatment group, the ANOVA included stratification for the factors used for randomization. If the primary analysis (aggregate acebilustat effect) reached the 0.05 level of significance (one-sided), the individual acebilustat doses would be compared to the placebo arm using Dunnett's procedure at the 0.05 (two-sided) alpha level.

Secondary Endpoints

Pulmonary exacerbations were analyzed both as the time to first pulmonary exacerbation and the rate of pulmonary exacerbations. The time to first protocol defined-pulmonary exacerbation were analyzed using a Cox proportional hazards model. The number of protocol-defined pulmonary exacerbations reported through the Week 48/Early Termination visit were annualized (where a year was defined as 52 weeks) analyzed using a negative binomial regression. The two active doses were compared to placebo individually as well as pooled together using a contrast statement similar to that used for the primary analysis. Point estimates, standard errors, and 95% CIs for the mean of number of pulmonary exacerbations were presented. The difference in means between each CTX-4430 group from placebo were presented along with standard errors and 95% CIs. Spirometry-based endpoints were analyzed using the same methods as the primary endpoint. Analyses of sputum DNA and elastase and serum high-sensitivity C-reactive protein were based upon descriptive statistics by treatment group.

Exploratory Endpoints

Analyses of sputum bacterial density (total and that for *P. aeruginosa*, *Burkholderia cepacia* complex, *Achromobacter xylosoxidans*, *Stenotrophomonas maltophilia*, and *Staphylococcus aureus* [including methicillin-resistant *S. aureus* and small colony variants of *S. aureus*)] and health-related quality of life (using the Cystic Fibrosis Questionnaire-Revised (CFQ-R) quality-of-life measure [Quittner et al., 2000]) were based upon descriptive statistics by treatment group.

Baseline Characteristics

A total of 200 patients were enrolled in the study. Patients had a mean age of 23.7 years, and mean $FEV_1pp$ of 70.6% overall at baseline. Nearly one-third of patients were using concomitant CFTR modulators. The mean number of exacerbations in the prior year was 2. Nearly half of all patients had experienced one exacerbation in the prior year; while 28.5% experienced two, and 25% three or more exacerbations.

Results

In this Phase IIb study, cystic fibrosis (CF) patients were enrolled into one of three treatment arms: placebo, 50 mg acebilustat, or 100 mg acebilustat (FIG. 2). The patients were pre-stratified across the treatment arms by three criteria: baseline lung function (as measured by FEV1 percent predicted, FEV1pp), the number of pulmonary exacerbations in the year prior to enrollment, and the use of concomitant treatment with CFTR modulator therapies. Enrolled patients were followed through 48 weeks of treatment and an additional 4 weeks post-treatment. During the course of the study, patients were monitored for changes in lung function and occurrence of pulmonary exacerbations in order to assess treatment effects.

Pulmonary exacerbations were an important secondary endpoint, since anti-inflammatory therapies are expected to demonstrate benefit in pulmonary exacerbations as compared to changes in spirometry, although this Phase 2 study was not powered to detect statistically significant changes in pulmonary exacerbations. The annual rate of pulmonary exacerbations was calculated by standard methods for each treatment group. Two main overall populations were examined: a Full Analysis Population (FAP), which consisted of any patient taking at least one dose of treatment, and a Per Protocol Population (PP), which consisted of patients meeting all inclusion/exclusion criteria and compliant with at least 80% of their treatment regimen and who also had an assessment at week 48.

Figure 3A:
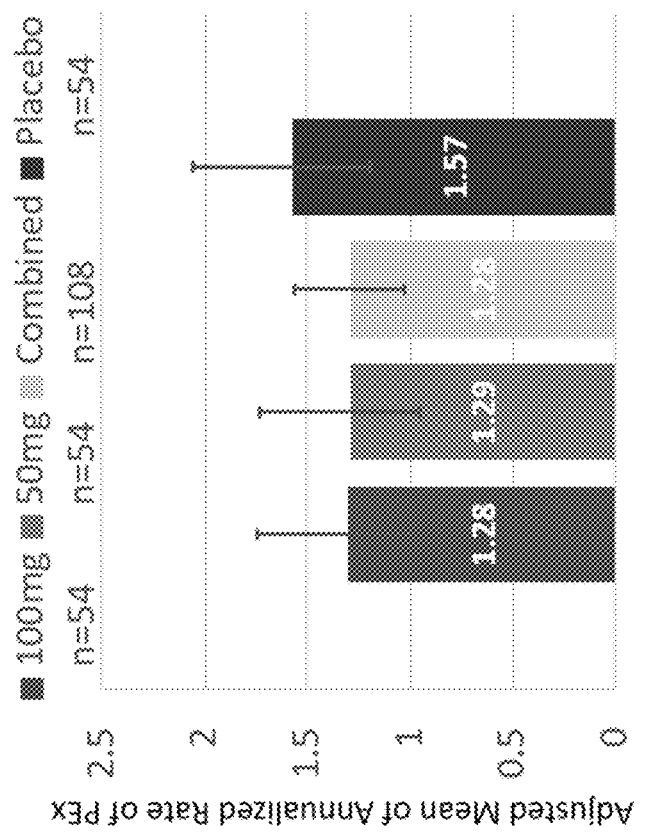
FIGS. 3A and 3B are bar graphs showing the adjusted mean of annualized rate of pulmonary exacerbations (PEx) (95% confidence interval) for patients administered acebilustat at 100 mg, 50 mg, combined treatment groups, or placebo (left to right), for the full analysis population (FAP) (FIG. 3A) and per-protocol population (PP) (FIG. 3B) across all lung disease phenotypes.
Figure 3B:
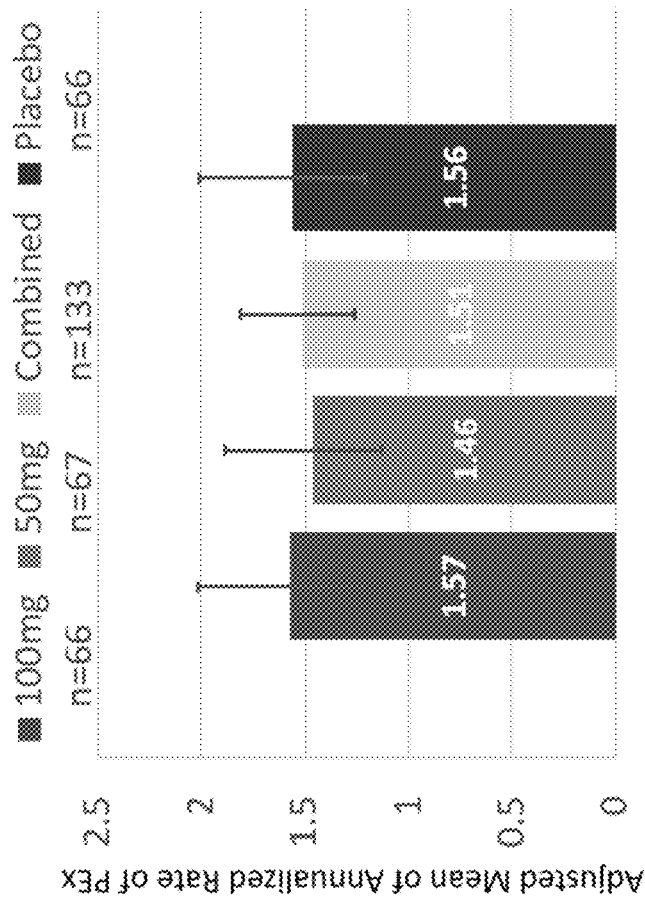
Figures 4A, 4B:
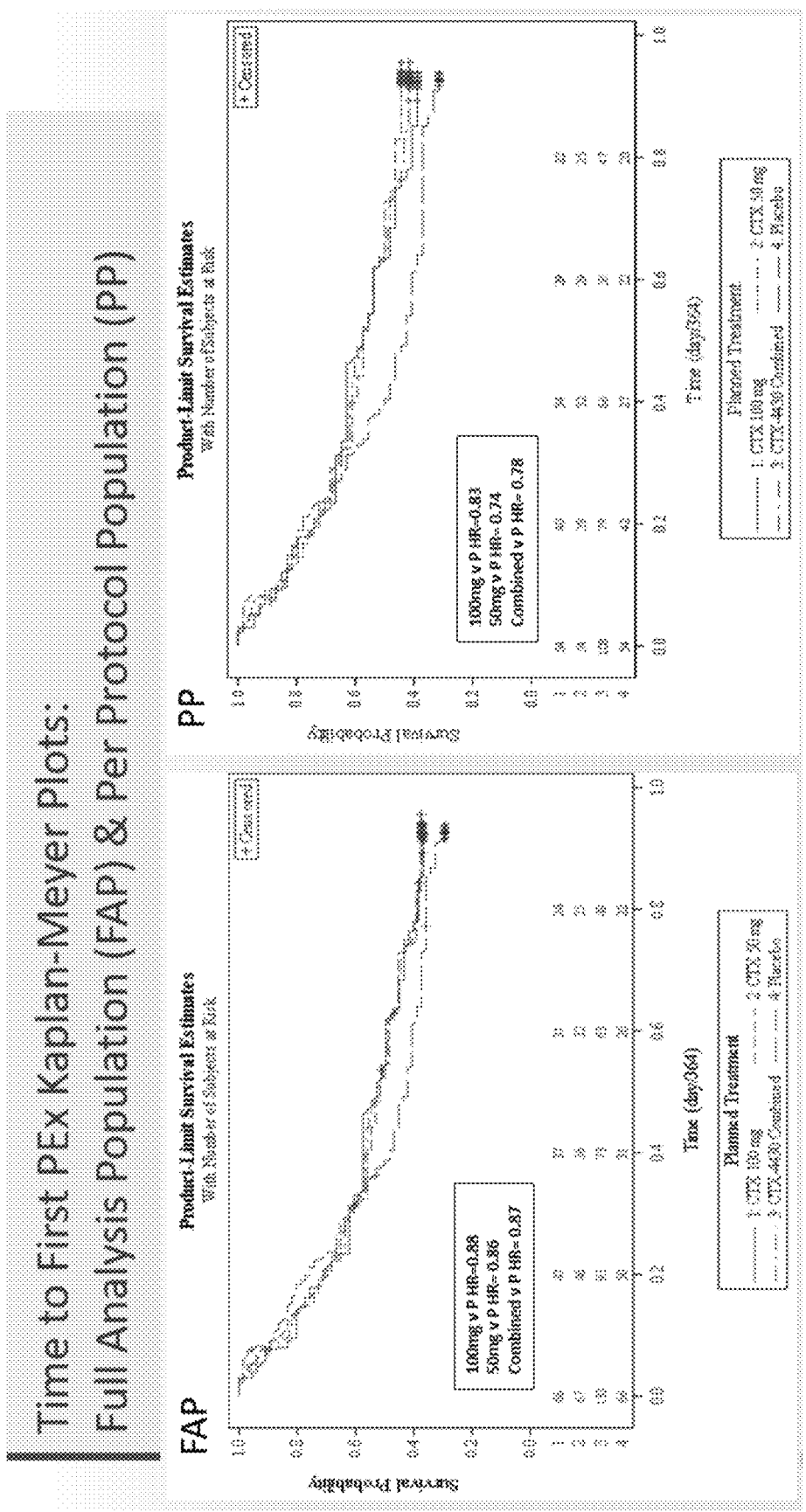
FIGS. 4A and 4B are Kaplan-Meier plots showing fraction of patients remaining exacerbation free as a function of time (as a fraction of 364) for patients administered acebilustat at 100 mg, 50 mg, combined treatment groups, or placebo, for the full analysis population (FAP) (FIG. 4A) and per-protocol (PP) (FIG. 4B) across all lung disease phenotypes studied.
Figures 5A, 5B:
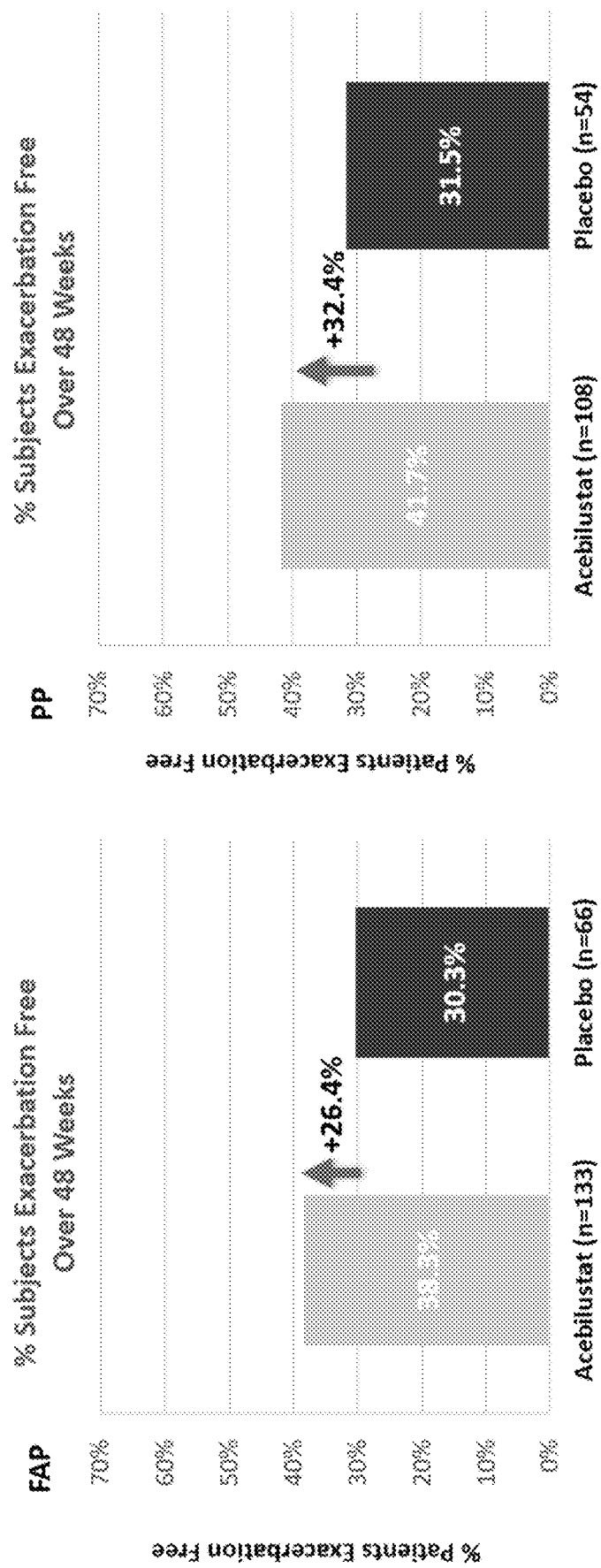
FIGS. 5A and 5B are bar graphs showing the percentage of patients treated with acebilustat or placebo that were exacerbation free over 48 weeks for the full analysis population (FAP) (FIG. 5A) and per-protocol (PP) (FIG. 5B) across all lung disease phenotypes.

In the FAP, the adjusted mean (95% CI) annualized pulmonary exacerbation rates based on the negative binomial regression model were 1.51 (1.26, 1.81) in the combined acebilustat groups, 1.57 (1.22, 2.02) in the 100 mg dose group and 1.46 (1.13, 1.89) in the 50 mg dose group), and 1.56 (1.21, 2.01) in the placebo group (FIG. 3A). The time to first pulmonary exacerbation was numerically greater in patients receiving acebilustat (combined and individual dose groups) versus placebo. The hazard ratios versus placebo (95% CI) were 0.87 (0.605, 1.246) in the acebilustat combined group, 0.88 (0.576, 1.339) in the acebilustat 100 mg group, and 0.86 (0.563, 1.308) in the acebilustat 50 mg group (FIG. 4A). The proportion of patients who did not experience a pulmonary exacerbation during the study period was also numerically greater in the acebilustat groups (51 of 133 patients [38%] in the combined acebilustat dose group, 25 of 66 patients [38%] in the 100 mg dose group, and 26 of 67 patients [39%] in the 50 mg group) than in the placebo group (20 of 66 patients [30%]) (FIGS. 5A and 6A). In the PP analysis, the difference in the rate of pulmonary exacerbations in the acebilustat group versus placebo was greater than the FAP (FIG. 3B). The time to first pulmonary exacerbation and the proportion of patients who did not experience a pulmonary exacerbation during the study was also numerically higher (FIGS. 4A, 4B, 5A, 5B, 6A and 6B). In the FAP and PP analysis, the divergence in pulmonary exacerbation from placebo occurred at approximately 4 months.

Kaplan-Meier analysis was conducted based on the fraction of patients remaining exacerbation free as a function of time (FIGS. 4A and 4B). The curves for the treated groups diverged from the placebo curve indicating an increased time to first exacerbation for both dose groups in both the FAP and PP (FIGS. 4A and 4B, respectively). At 48 weeks, the hazard ratios for risk of exacerbation indicate a treatment effect for both acebilustat dose groups in reduced risk of exacerbation compared to placebo. In addition, the number of patients who did not experience a pulmonary exacerbation over the course of the 48 weeks of treatment was determined for each treatment group. This analysis indicates a larger proportion of patients treated with acebilustat remained exacerbation-free in both the FAP (FIGS. 5A and 6A) and PP (FIGS. 5B and 6B).

Figures 7A, 7B:
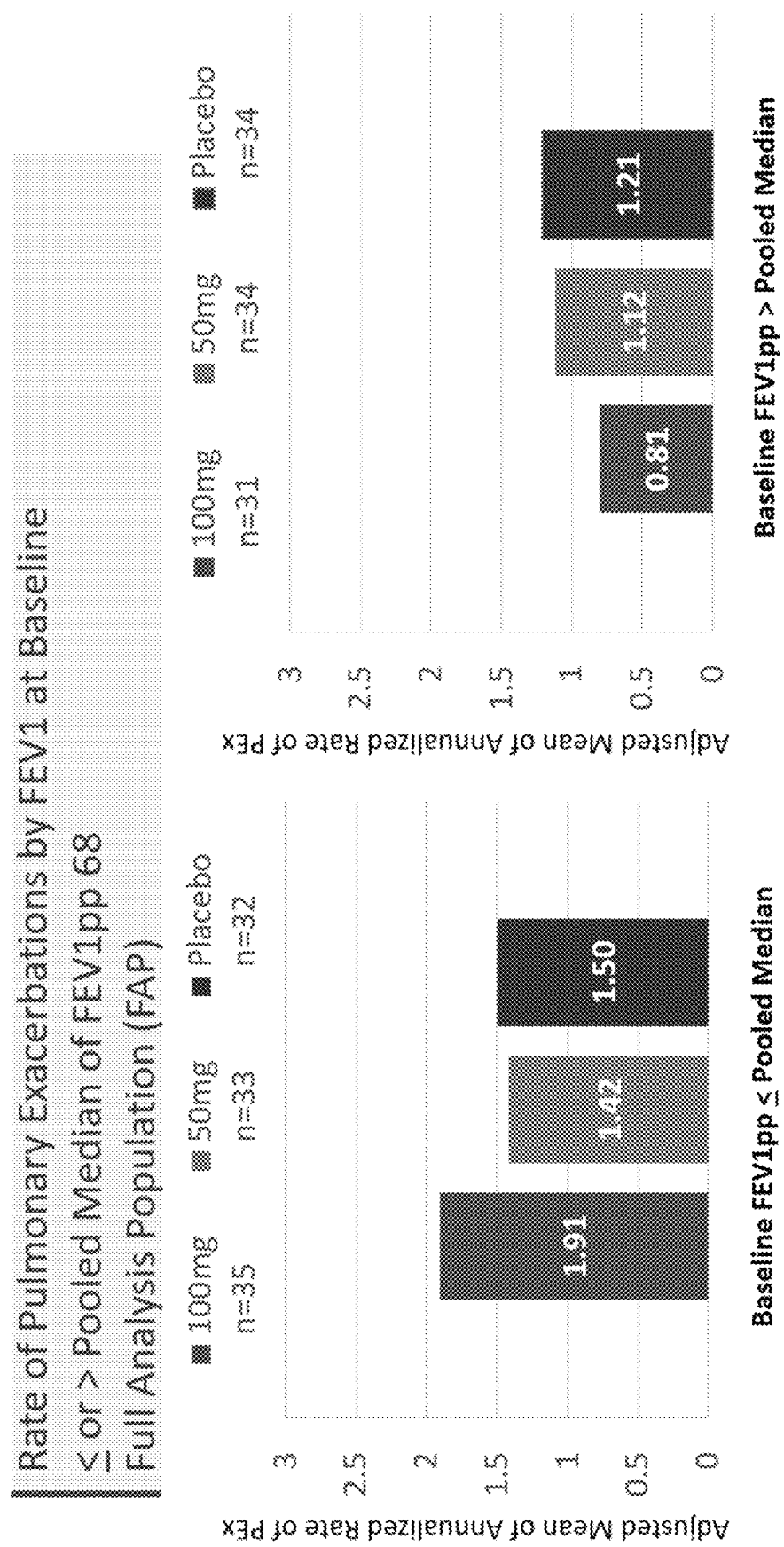
FIGS. 7A and 7B are bar graphs showing the adjusted mean of annualized rate of pulmonary exacerbations (PEx) (95% confidence interval) for patients treated with acebilustat at 100 mg, 50 mg, or placebo (left to right) for patients having a mild lung disease phenotype characterized by FEV1pp greater than pooled median of 68% at baseline (FIG. 7B) and patients having more severe lung disease phenotype, FEV1pp less than or equal to pooled median 68% (FIG. 7A).

In a prespecified analysis, CF patients in the study were grouped according to their baseline lung function being above or below the median FEV1pp for the entire study population, which was found to be 68%. Patients with milder lung disease, those with baseline FEV1pp higher than the median (>68%), were found to respond to acebilustat treatment as evidenced by a lower annual rate of pulmonary exacerbations versus placebo (FIG. 7B). In contrast, patients with baseline FEV1pp at or below the median (≤68%) did not exhibit the same level of response to acebilustat treatment (FIG. 7A).

Figures 8A, 8B:
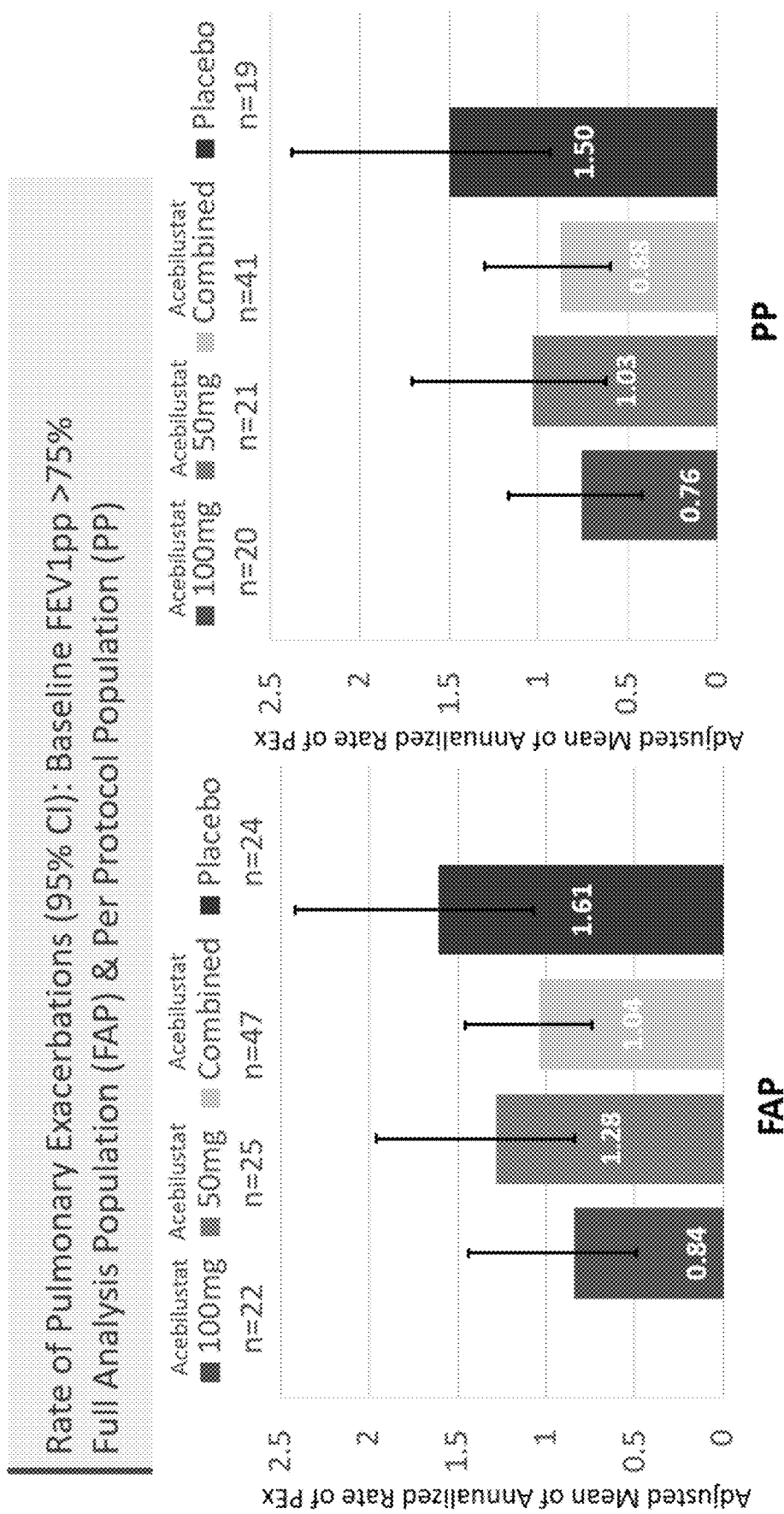
FIGS. 8A and 8B are bar graphs showing the adjusted mean of annualized rate of pulmonary exacerbations (PEx) (95% confidence interval) for patients treated with acebilustat at 100 mg, 50 mg, combined, or placebo (left to right) for patients having an FEV1pp greater than 75% at baseline for the full analysis population (FIG. 8A) and per protocol population (FIG. 8B).
Figures 9A, 9B:
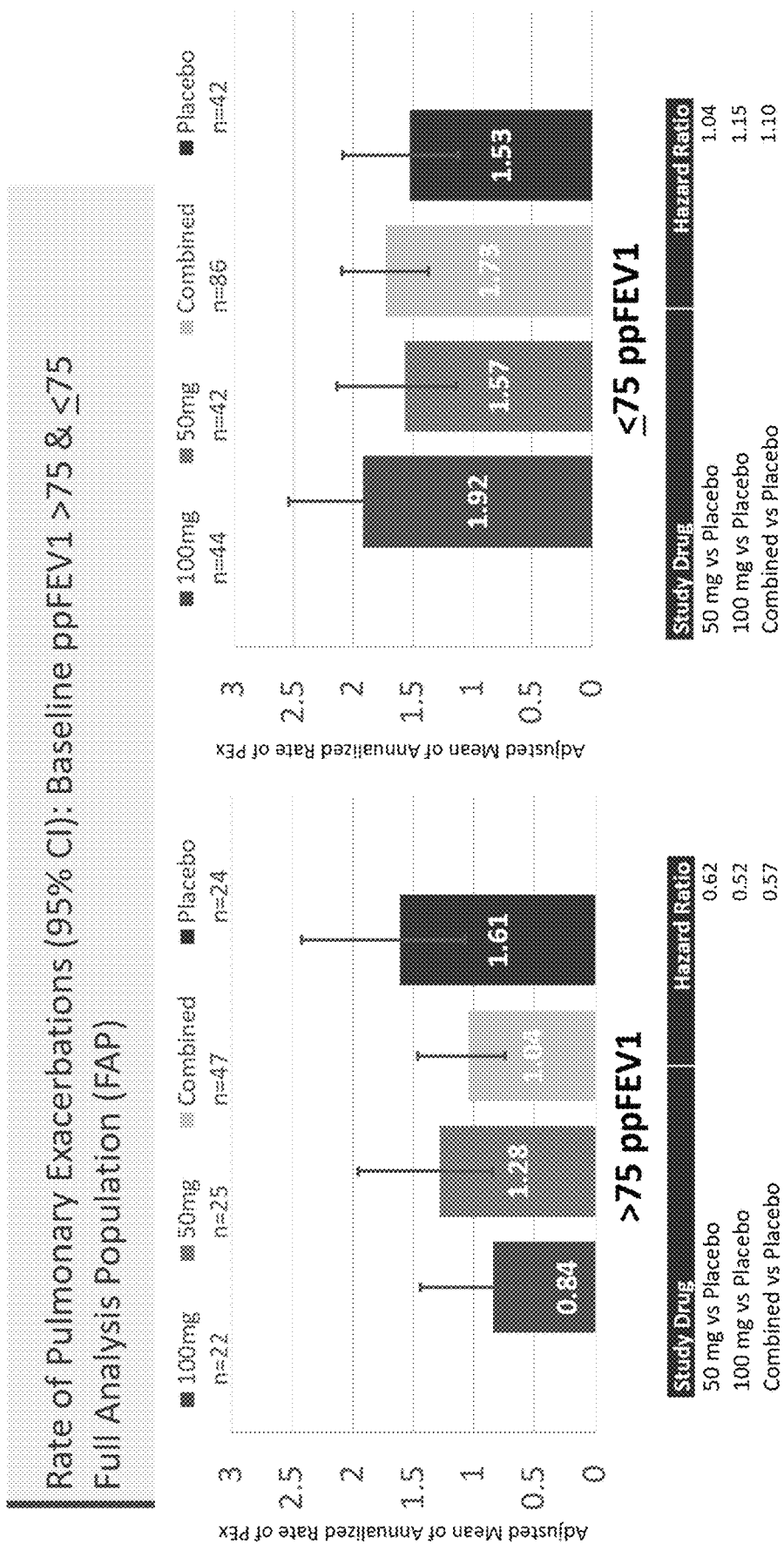
FIGS. 9A and 9B are bar graphs showing the adjusted mean of annualized rate of pulmonary exacerbations (PEx) (95% confidence interval) for patients treated with acebilustat at 100 mg, 50 mg, or placebo (left to right) for patients having an FEV1pp greater than 75% at baseline (FIG. 9A) and patients having an FEV1pp less than or equal to 75% (FIG. 9B) for the full analysis population (FAP).
Figures 10A, 10B:
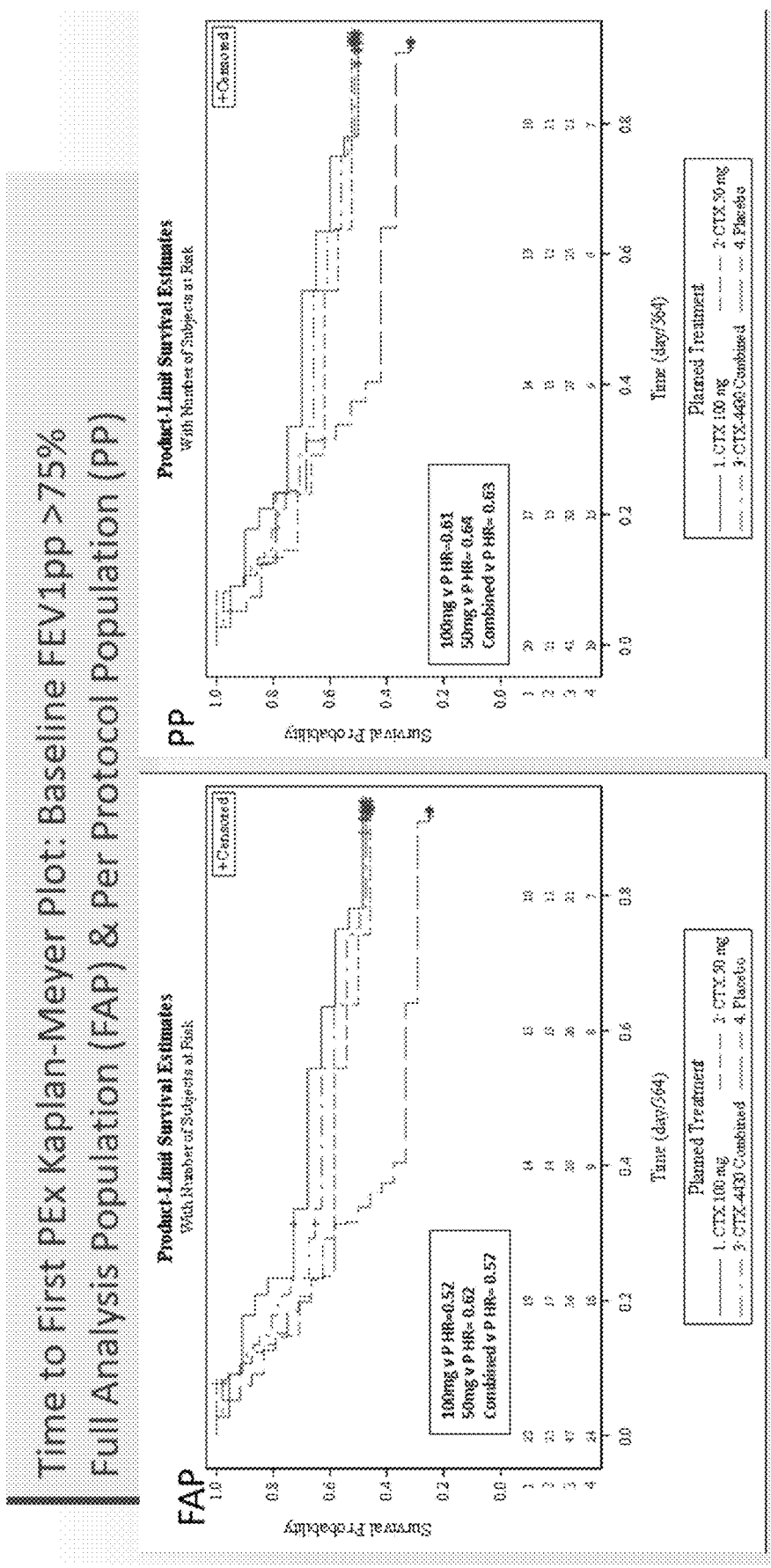
FIGS. 10A and 10B are Kaplan-Meier plots showing fraction of patients remaining exacerbation free as a function of time (as a fraction of 364) for patients that had a FEV1pp>75% at baseline and were administered acebilustat at 100 mg, 50 mg, combined treatment groups, or placebo, for the full analysis population (FAP) (FIG. 10A) and per-protocol (PP) (FIG. 10B).
Figure 11:
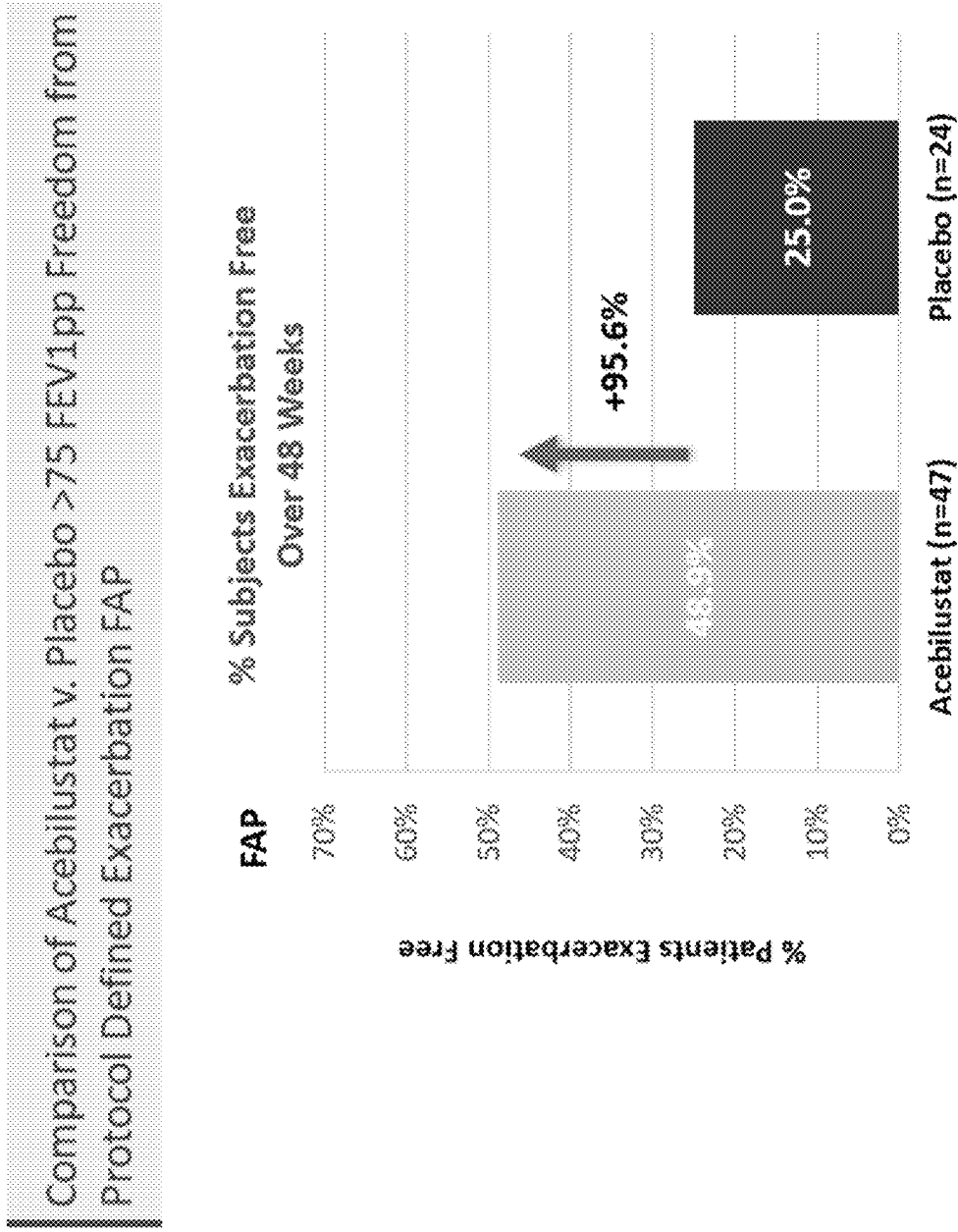
FIG. 11 is a bar graph showing the percentage of patients that had a FEV1pp>75% at baseline treated with acebilustat or placebo that were exacerbation free over 48 weeks for the full analysis population (FAP).

In a prespecified analysis, CF patients in the study were grouped according to their baseline lung function (FEV1pp 50-75, or >75%). Patients with milder lung disease (baseline FEV1pp>75%), were found to respond to acebilustat treatment as evidenced by a lower annual rate of pulmonary exacerbations in both the FAP and PP (FIGS. 8A and 8B, respectively). Specifically, the mean annualized rate of pulmonary exacerbation in patients with baseline FEV1pp>75% was lower by about 35% in the combined acebilustat dose groups versus placebo; this difference was greater than in the overall study population. The adjusted mean (95% CI) annualized rate of pulmonary exacerbations in this pre-specified FAP population was 1.04 (0.74, 1.46) in the combined acebilustat groups, 0.84 (0.49, 1.44) in the 100 mg dose group, and 1.28 (0.84, 1.96) in the 50 mg dose group versus 1.61 (1.07, 2.42) in the placebo group (FIG. 9A). The effect of acebilustat versus placebo on time to first pulmonary exacerbation was also more pronounced in this population than in the overall trial population. Hazard ratios (95% CI) versus placebo were 0.57 (0.307, 1.051) in the acebilustat combined group, 0.52 (0.245, 1.101) in the acebilustat 100 mg group, and 0.62 (0.304, 1.274) in the acebilustat 50 mg group for the FAP (FIG. 9A). Almost half of the patients with mild disease receiving acebilustat did not have a pulmonary exacerbation during the study (23 of 47 patients [49%] in the combined acebilustat group; 11 of 22 patients [50%] in the 100 mg acebilustat group; 12 of 25 patients [48%] in the 50-mg acebilustat group), while only 6 of 24 patients (25%) in the placebo group did not have a pulmonary exacerbation (FIG. 11, 17A, 18A). The exacerbation rate data for subjects with baseline FEV1pp≤75% is shown in Table 1 below. These patients did show a numerical benefit in the rate of exacerbations versus placebo but the difference was less pronounced. In contrast to patients with baseline FEV1pp above 75% (FIG. 9A), those patients with FEV1 at or below 75% (≤75%) did not exhibit the same level of response to acebilustat treatment (FIG. 9B). This is evidenced by both a reduced annual rate of exacerbations and a reduced hazard ratio for time to first exacerbation in the population with baseline FEV1pp>75% (FIG. 9A) as compared to an unchanged or increased rate and hazard ratio in the population with FEV1pp at or below 75% (≤75%) (FIG. 9B). Kaplan-Meier analysis of the population of CF patients with baseline FEV1pp>75% indicated a prolonged time to first exacerbation and a reduced hazard ratio for risk of exacerbation compared to placebo for both acebilustat dose groups in both FAP and PP (FIGS. 10A and 10B, respectively). In addition, more patients treated with acebilustat in the group having baseline FEV1pp>75% remained free from pulmonary exacerbation during the 48 weeks of treatment compared to those in the placebo group (FIG. 11).

Figures 15A, 15B:
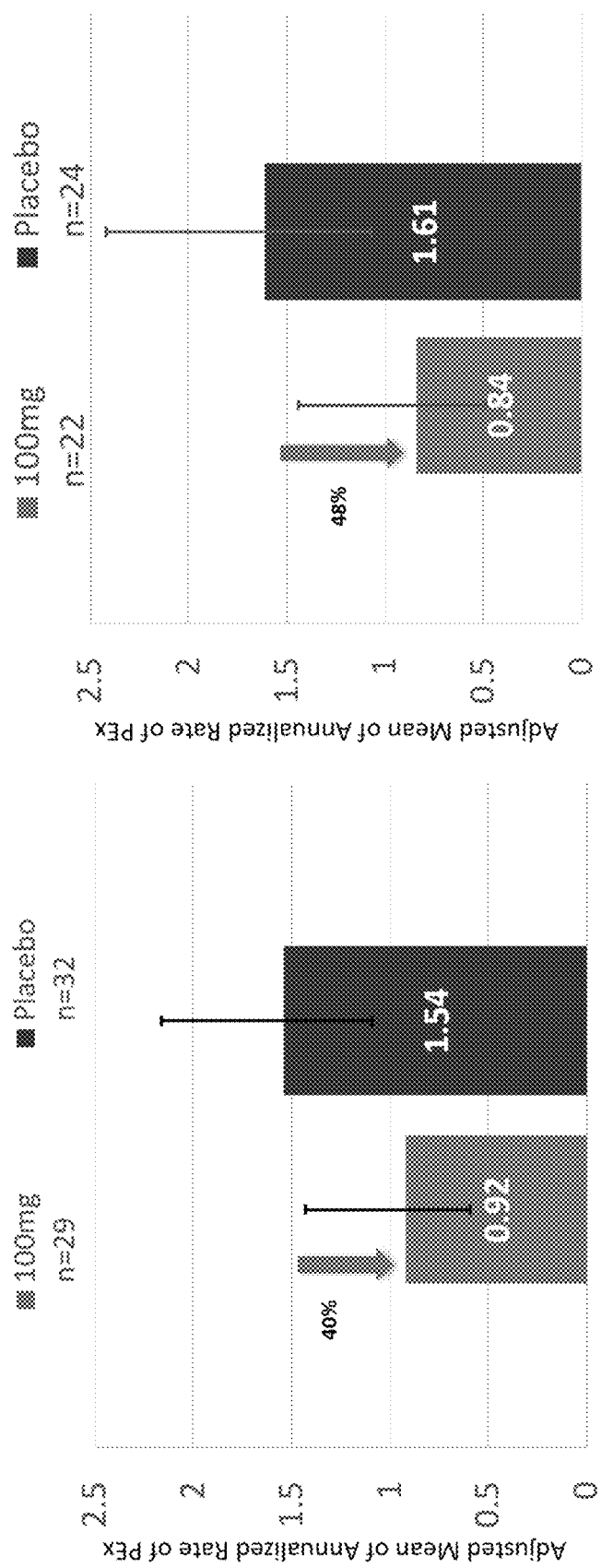
FIGS. 15A and 15B are bar graphs showing the effect of acebilustat on adjusted mean of annualized rate of pulmonary exacerbation in patients having baseline FEV1pp>70% (the CF community standard definition of "mild" CF disease.

FIGS. 15A and 15B show the effect of acebilustat on pulmonary exacerbation rate in patients having baseline FEV1pp>70, which is the CF community standard definition of "mild" CF disease, compared to patients having baseline FEV1pp>75 (the prespecified definition of "mild" CF used in the clinical study). As shown in the figure, acebilustat demonstrates a substantial reduction in pulmonary exacerbations in both groups with varying definitions of "mild" CF disease.

In summary, the therapeutic effect of acebilustat in reducing pulmonary exacerbations is greatest in CF patients with the higher FEV1pp at baseline ("mild CF disease"). Table 1 shows that both the 50 mg and 100 mg doses showed therapeutic benefit in patients with a baseline FEV1pp of 65% or greater, with the greatest benefit seen at baseline ppFEV1 above 70%. The 100 mg dose of acebilustat also showed therapeutic benefit at baseline FEV1pp of greater than 60%. The terms "FEV1pp" and "ppFEV1" are used interchangeably.

TABLE 1

Annualized Rate of Pulmonary Exacerbation (Adjusted Mean)

| Subgroup | Acebilustat 100 mg | Acebilustat 100 mg % difference from Placebo | Acebilustat 50 mg | Acebilustat 50 mg % difference from Placebo | Placebo |
|---|---|---|---|---|---|
| Baseline ppFEV$_1$ > 60 | 1.27 | −14% | 1.44 | −2% | 1.47 |
| Baseline ppFEV$_1$ > 65 | 1.05 | −28% | 1.25 | −14% | 1.45 |
| Baseline ppFEV$_1$ > 68 | 0.81 | −33% | 1.12 | −7% | 1.21 |
| Baseline ppFEV$_1$ > 70 | 0.92 | −40% | 1.2 | −22% | 1.54 |
| Baseline ppFEV$_1$ > 75 | 0.84 | −48% | 1.28 | −20% | 1.61 |

Figures 12A, 12B:
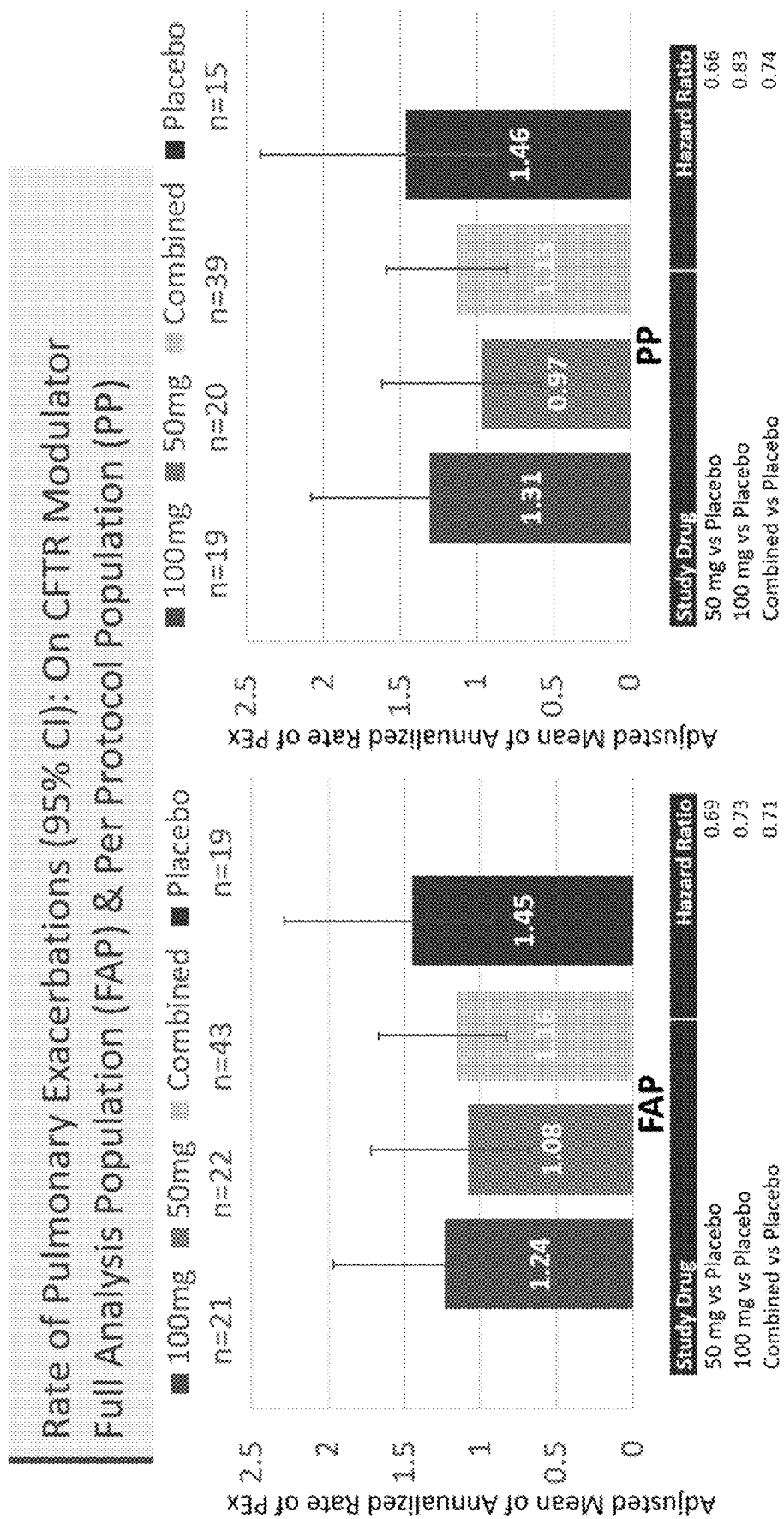
FIGS. 12A and 12B are bar graphs showing the adjusted mean of annualized rate of pulmonary exacerbations (PEx) (95% confidence interval) for patients on CFTR modulator therapy administered acebilustat at 100 mg, 50 mg, combined treatment groups, or placebo (left to right), for the full analysis population (FAP) (FIG. 12A) and per-protocol (PP) (FIG. 12B).
Figure 14:
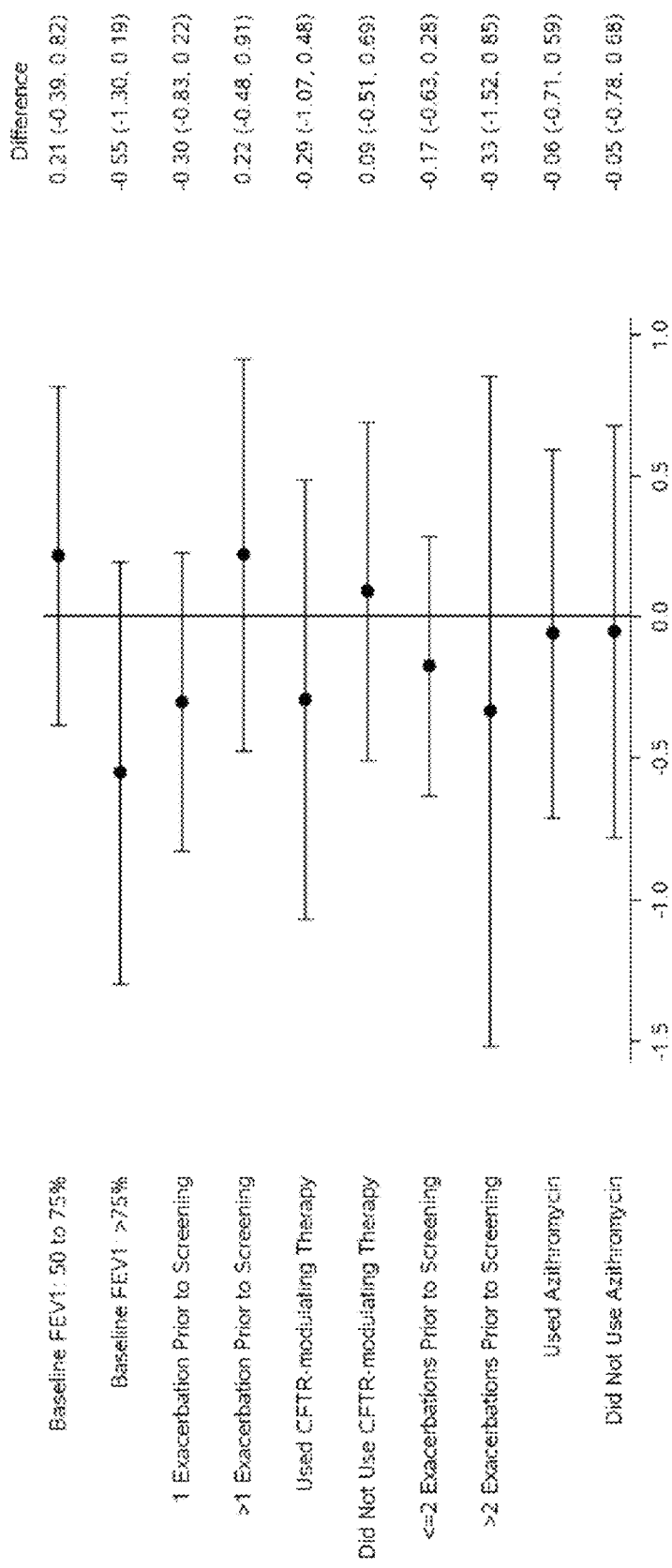
FIG. 14 is a forest plot showing the difference in the rate of pulmonary exacerbations for acebilustat treatment groups (50 mg and 100 mg combined) versus placebo for the per-protocol analysis set for patients having a FEV1pp of 50 to 75% at baseline, patients having a FEV1pp of greater than or equal to 75% at baseline, patients having one exacerbation in the year prior to screening, patients having greater than one exacerbation in the year prior to screening, patients that used CFTR-modulating therapy, patients off CFTR modulator therapy, patients that had two or fewer pulmonary exacerbations in the year prior to screening, patients that had more than one pulmonary exacerbations in the year prior to screening, patients using azithromycin, and patients not treated with azithromycin.

In addition, patients taking acebilustat alongside concomitant treatment with CFTR-modulator therapies exhibited a reduced annual rate of pulmonary exacerbations and a reduced hazard ratio for risk of exacerbation compared to patients taking placebo alongside concomitant CFTR-targeted therapy (FIGS. 12A and 12B). These effects were evident for both acebilustat doses in both the FAP and PP populations (FIGS. 12A and 12B, respectively). Additionally, the proportion of exacerbation free CF patients taking acebilustat with concomitant treatment with CFTR-modulator therapy was lower compared to patients taking placebo with concomitant CFTR-targeted therapy (FIGS. 13A and 13B). This effect persisted until the end of the 48 weeks of treatment and was evident for both acebilustat doses in both the FAP and PP populations (FIGS. 13A and 13B, respectively).

Figures 16A, 16B:
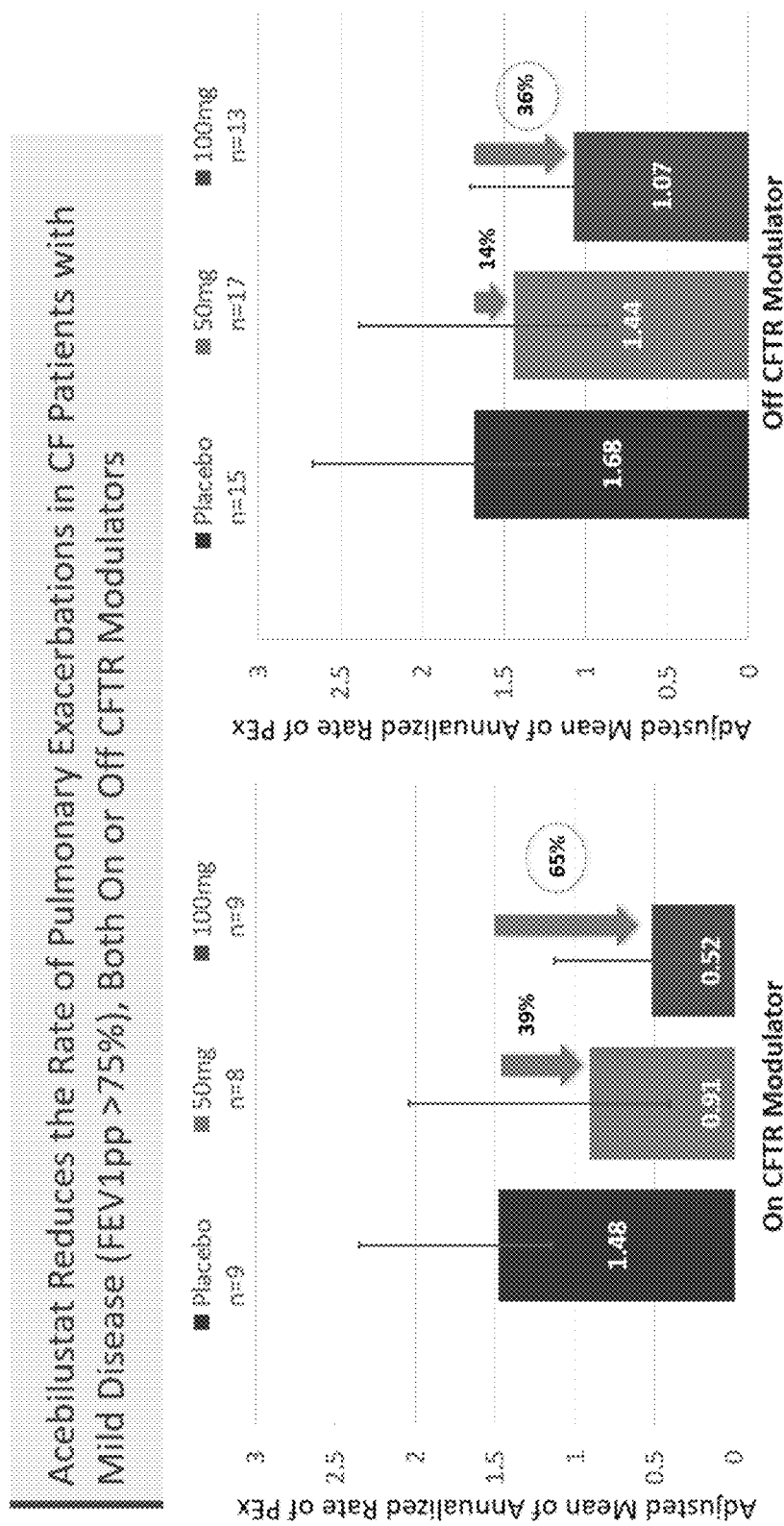
FIGS. 16A and 16B are bar graphs showing the effect of acebilustat on the adjusted mean of annualized rate of pulmonary exacerbations in populations taking concomitant CFTR modulator therapy ("On"

As shown in FIGS. 16A and 16B, acebilustat treated patients had a lower pulmonary exacerbation rate in CF patients with mild disease (FEV1pp>75) whether taking ("on") or not taking ("off") concomitant CFTR modulator therapy. The greatest effect of acebilustat on pulmonary exacerbations in the entire study (65% lower versus placebo for the 100 mg dose) was observed in patients with mild disease concomitantly treated with CFTR modulator therapies (FIG. 16A), suggesting the potential for mechanistic synergy. For the data shown in FIGS. 16A and 16B, the corresponding placebo groups were matched with the acebilustat treatment groups in regard to CFTR modulator use, i.e., for the patients "on" CFTR modulator, patients taking acebilustat plus CFTR modulator were compared to those taking CFTR modulator alone.

Figures 17A, 17B, 17C:
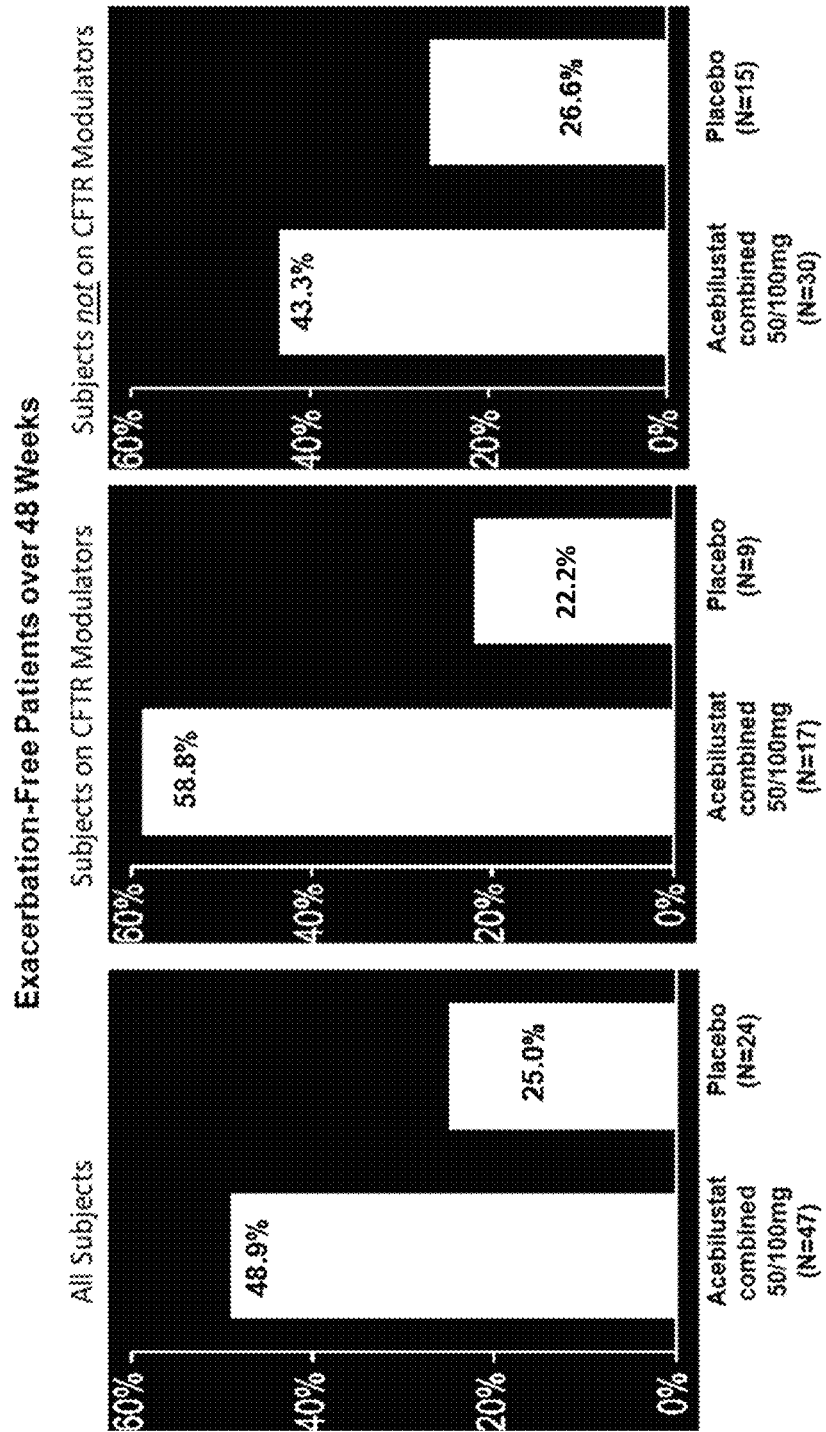
FIGS. 17A, 17B, and 17C are bar graphs showing percentage of exacerbation-free patients (treated with acebilustat or placebo) for the 48 weeks of the treatment for the mild CF patients (FIG. 17A) and "on" or "off" CFTR modulatory therapy (FIGS. 17B and 17C, respectively).

As shown in FIGS. 17A to 17C, acebilustat treated patients had a higher proportion (versus placebo) of patients free from pulmonary exacerbations during the course of the 48 weeks of treatment in the total study population (FIG. 17A) as well as in mild CF patients whether taking ("on") (FIG. 17B) or not taking ("off") (FIG. 17C) concomitant CFTR modulator therapy. Suprisingly, and consistent with the effect on pulmonary exacerbation rate, the effect of acebilustat in increasing the percentage of exacerbation-free patients was greatest in patients taking concomitant CFTR modulator therapy (see FIG. 17B).

Figures 18A, 18B:
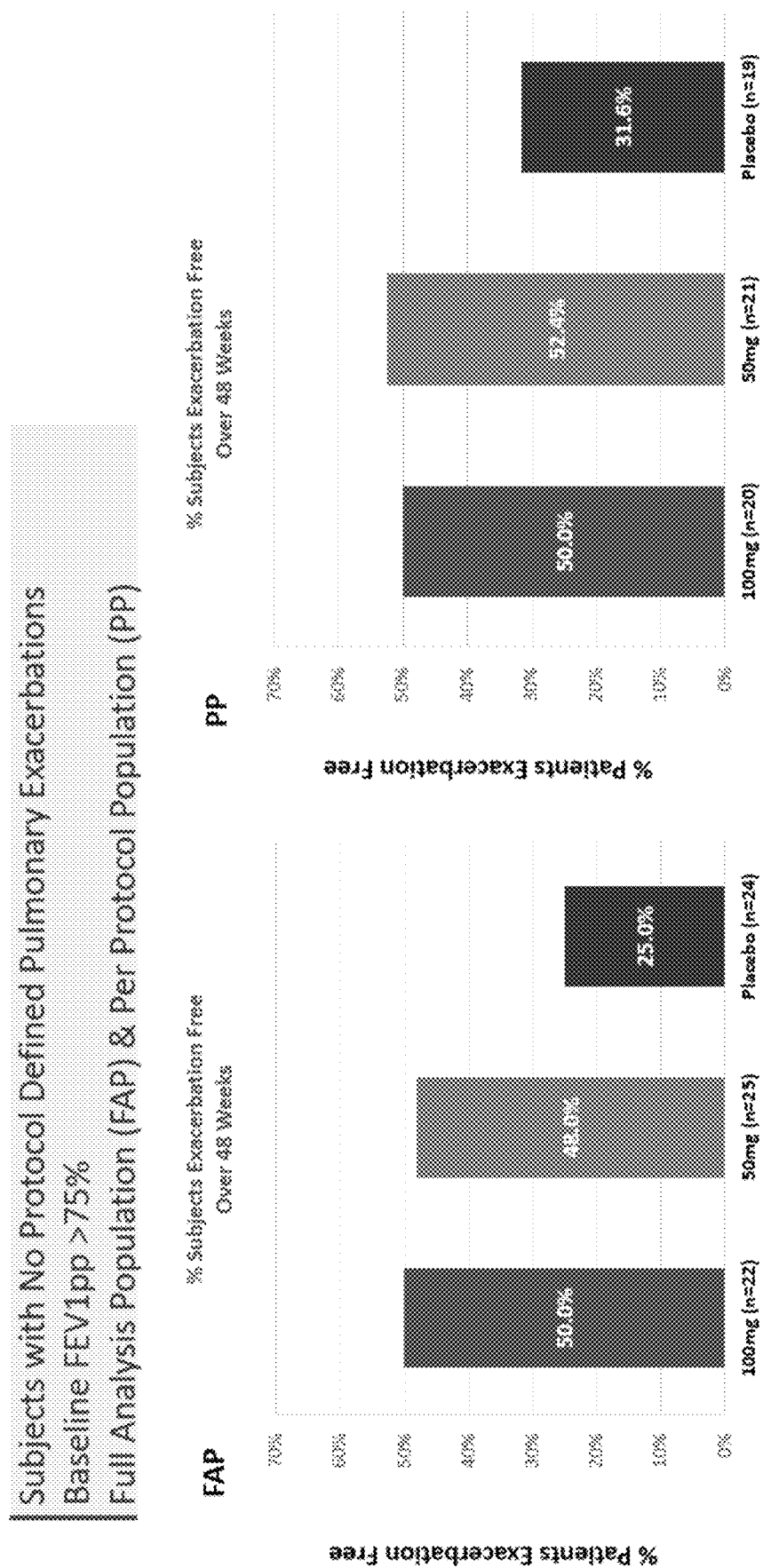
FIGS. 18A and 18B are bar graphs showing percentage of exacerbation-free patients treated with 100 mg acebilustat, patients treated with 50 mg acebilustat, and placebo for the 48 weeks of the treatment for patients having baseline FEV1pp>75% for the full analysis population (FAP) (FIG. 12A) and per-protocol (PP) (FIG. 12B).
Figure 20:
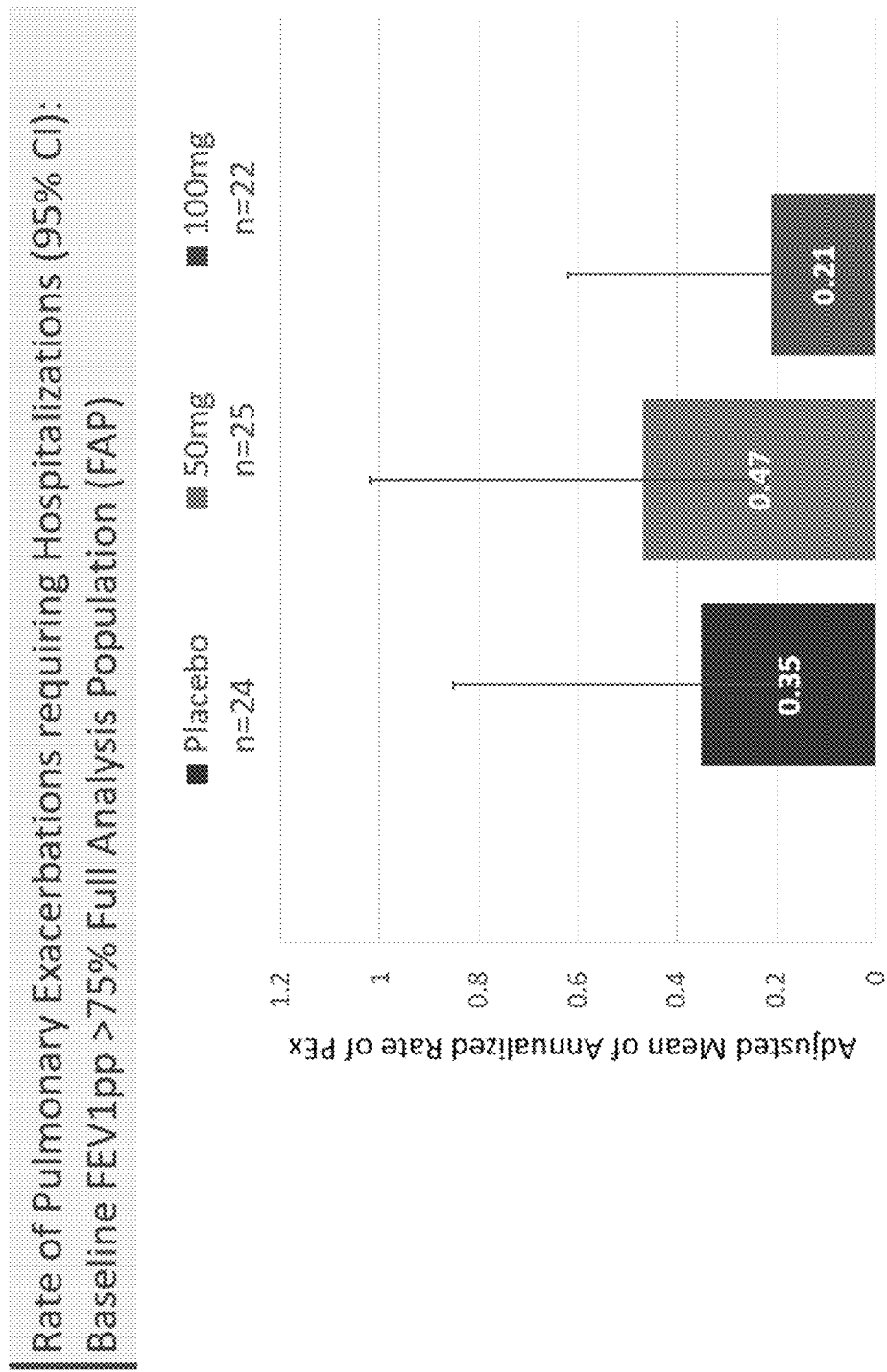
FIG. 20 is a bar graph showing the effect of acebilustat (50 and 100 mg) on adjusted mean of annualized rate of pulmonary exacerbations requiring hospitalization in patients having baseline FEV1pp>75% for the full analysis population (FAP).
Figure 21:
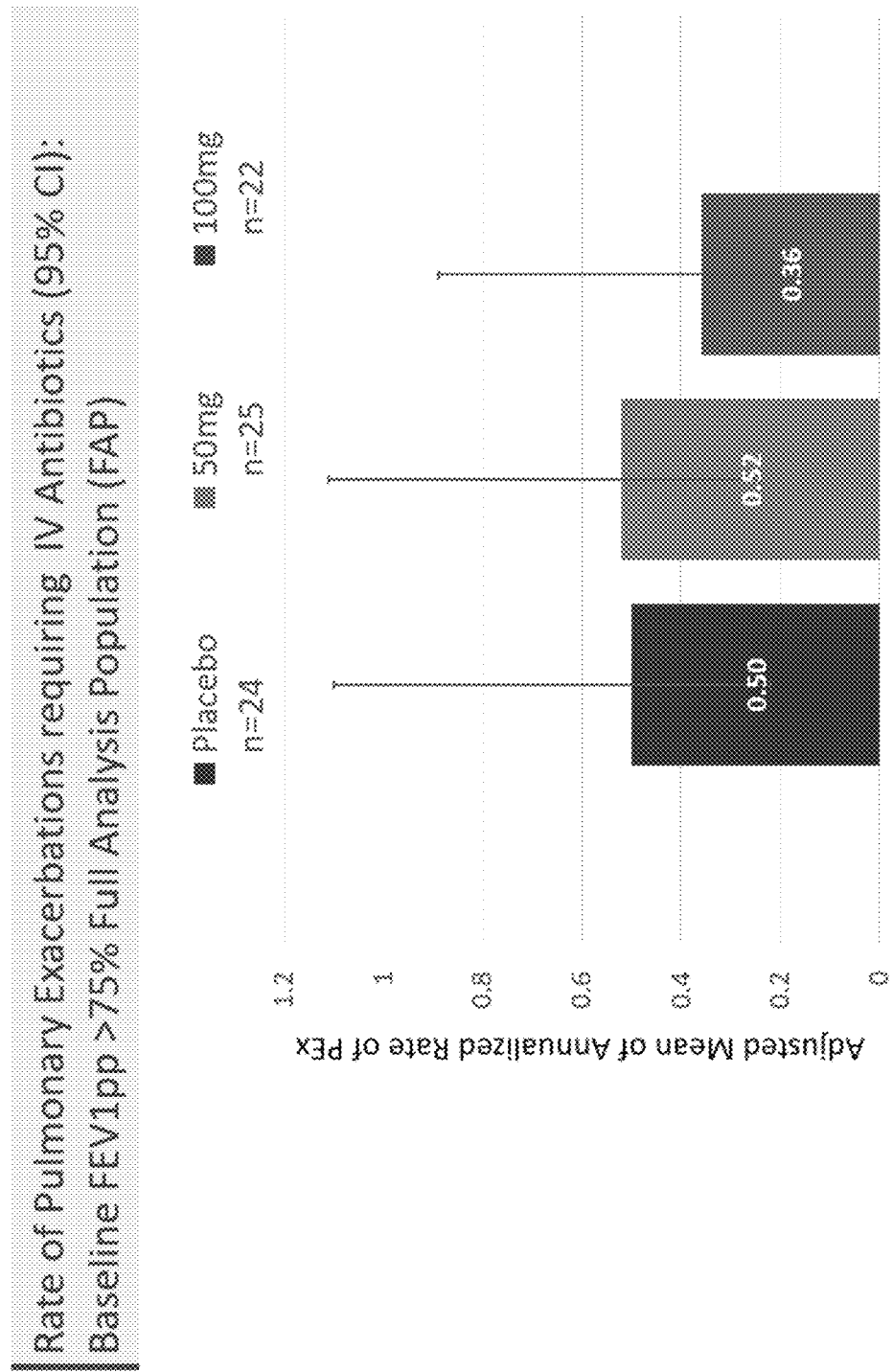
FIG. 21 is a bar graph showing the effect of acebilustat (50 and 100 mg) on adjusted mean of annualized rate of pulmonary exacerbations requiring intravenous (IV) antibiotics in patients having baseline FEV1pp>75% for the full analysis population (FAP).

FIGS. 18A and 18B shows that both the 100 mg and 50 mg dose of acebilustat had a higher percentage of exacerbation-free patients in the mild (FEV1pp>75%) subgroup. FIGS. 20 and 21 show that the 100 mg dose of acebilustat had a lower rate of pulmonary exacerbations requiring hospitalization and a lower the rate of pulmonary exacerbations requiring intravenous antibiotics as compared to placebo.

Figures 19A, 19B:
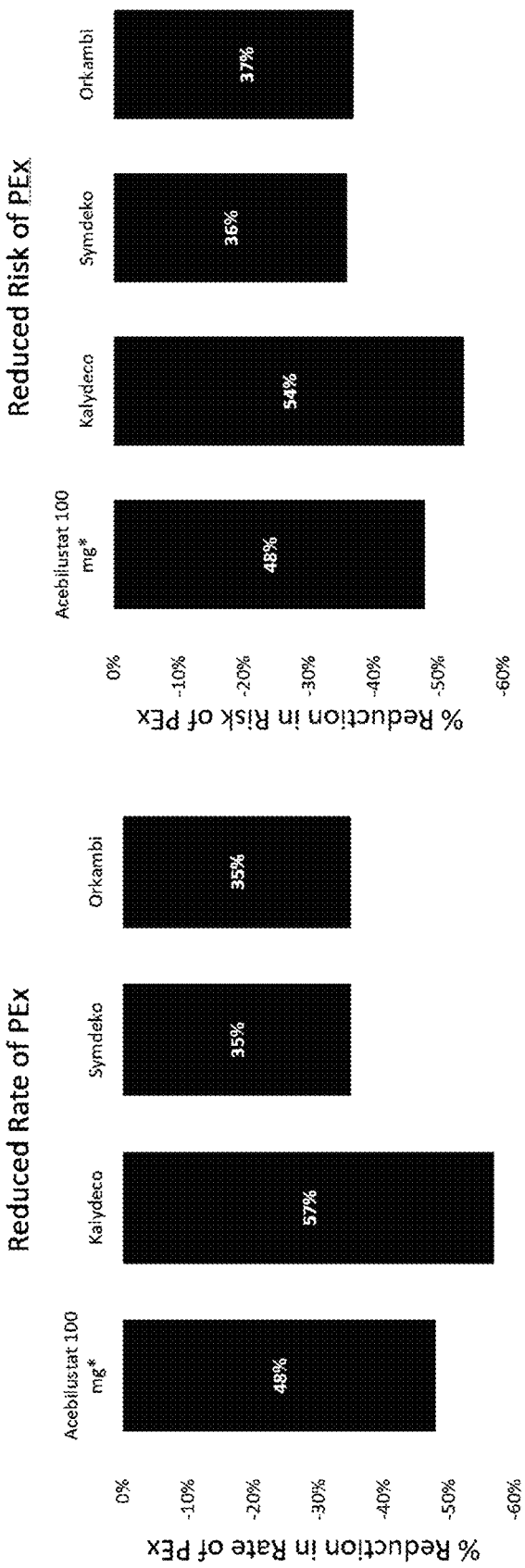
FIGS. 19A and 19B are bar graphs showing the estimated effects of acebilustat at 100 mg and CFTR modulator therapies (KALYDECO®, SYMDEKO®, and ORKAMBI®) on percent reduction in rate of pulmonary exacerbations (FIG. 19A) and percent reduction in risk of pulmonary exacerbations (FIG. 19B).

FIGS. 19A and 19B show the effect acebilustat (100 mg in the mild population) and CFTR modulator therapies (KALYDECO®, SYMDEKO®, and ORKAMBI®) on percent differences from placebo in rate of pulmonary exacerbations and risk of pulmonary exacerbations, respectively. These figures show that the magnitude of effect of acebilustat (100 mg dose) in the mild CF population in terms of benefit in both annual rate and risk of pulmonary exacerbations was similar or better than that observed for recently approved CFTR modulator therapies (at approved doses) in their respective genetically-targeted populations. Even though this is data from different studies, this confirms that the level of effect seen for acebilustat in terms of pulmonary exacerbations is considered therapeutically meaningful.

In summary, the major effect of acebilustat is a reduction in the rate of pulmonary exacerbations (PEx) and reduced risk of progression to pulmonary exacerbations. In the study, acebilustat demonstrated clinically meaningful improvements in pulmonary exacerbations, both reducing the frequency of pulmonary exacerbations (PEx) and increasing time to next exacerbation over 48 weeks of therapy. Patients in key prospectively-identified sub-groups, including those with mild CF lung disease at baseline and/or taking concomitant CFTR modulator therapy, derived the most benefit. The benefit, when used in combination with a CFTR modulator, is an important consideration given the likelihood of an increase in number of CF patients who are eligible to be treated with CFTR modulators over the coming years. This addresses the unmet need to reduce lung inflammation, that persists despite CFTR modulator therapy, adequately for the optimal treatment of patients with cystic fibrosis. Acebilustat-treated patients exhibited an 18% reduction in PEx and a 22% reduced risk in progressing to first PEx versus placebo. Additionally, compared with placebo, 32% more patients treated with acebilustat had no PEx during the study. The benefits of acebilustat on pulmonary exacerbations were apparent as early as four months after start of treatment and persisted throughout the 48 weeks of the study. Lung function, as measured by FEV1 percent predicted (FEV1pp), in acebilustat-treated patients was not different from placebo over 48 weeks of therapy. Previous research with CFTR modulators have shown that, on an individual patient basis, FEV1pp response does not always correlate with PEx response.

Patients with less severe impairment of lung function (FEV1pp>75) achieved the largest benefit from acebilustat therapy, achieving a 34% reduction in PEx rate, a 43% reduction in risk of experiencing their first exacerbation and a 96% increased likelihood of being exacerbation free after 48 weeks of treatment. Furthermore, patients concomitantly treated with CFTR modulator therapy exhibited a clinically meaningful 18% reduction in PEx, a 29% increased time to first exacerbation and a 47% higher likelihood of no exacerbations compared to patients treated with CFTR modulators and placebo. Acebilustat was well tolerated with no increased risk of infection, a key attribute for any anti-inflammatory development candidate to treat CF patients who have an increased risk of infection. The majority of adverse events were mild or moderate in severity. There was a low discontinuation rate from adverse events.

Patients treated with acebilustat exhibited a slight FEV1pp improvement but did not separate from placebo on the primary endpoint. Specifically, FEV1pp had wide variability and was not predictive of decreased pulmonary exacerbation (PEx responders). This study provides evidence that decrease in pulmonary exacerbations is a better outcome measurement from anti-inflammatory therapy than FEV1pp.

Discussion

The damaging impact of chronic inflammation is well recognized in CF. Although CFTR mutations have been implicated in some aspects of inflammation [Rubin 2007; Perez et al., 2007], CFTR modulators do not fully address chronic lung inflammation [Rowe et al., 2014], making treatments in this area a significant unmet need [Torphy et al., 2015].

The LTA4 inhibitor acebilustat is in development as an anti-inflammatory therapy in CF and has shown promising results in Phase I studies. In a study of once-daily acebilustat in adult patients with CF, the drug significantly reduced sputum neutrophil levels by up to 65% and sputum elastase levels by up to 58%. Numerical reductions in C-reactive protein were observed in the acebilustat treated groups [Elborn et al., 2017a]. Sputum LTB4 levels decreased significantly in acebilustat-vs placebo-treated patients [Elborn et al., 2017b]. These Phase I studies highlighted several important PK/PD aspects of acebilustat. Data confirmed that once-daily oral dosing is appropriate [Elborn et al., 2017b]. No significant differences occurred between healthy volunteers and patients with CF in the $C_{max}$ or $AUC_{0-24}$ of acebilustat. Given the high burden of CF therapies [Harman et al., 2017], a simple dosing regimen for any additional therapies is important. Furthermore, no differences occurred in the $AUC_{0-24}$ at steady state in fed vs fasting patients [Elborn et al., 2017b]. This is relevant given the potential for compromised absorption from the gut in patients with CF and their complex dietary needs [Li and Somerset 2014]. Additionally, acebilustat did not induce CYP3A4, a known metabolizer of the CFTR modulator ivacaftor and, importantly, these data show that the two drugs (acebilustat and ivacaftor) could be taken concomitantly [Elborn et al., 2017b]. The adverse event profile of acebilustat was closely monitored in the Phase I studies. Reassuringly, acebilustat was well tolerated in these trials. The majority of treatment-emergent adverse events (AEs) were mild or moderate in severity and no drug-related serious AEs occurred in these studies [Elborn et al., 2017a, b].

The promising data from the Phase I studies led to the progression of acebilustat into the Phase IIb trial described here. The trial has been robustly designed, taking into account guidance from the CFF, including recommendations from the 2014 CFF Anti-inflammatory Strategy Group (CFF-ASG) [Torphy et al., 2015]. The study endpoints examined both change from baseline in lung function and pulmonary exacerbations, both of which have real-life clinical impacts. Lung function decline is a powerful predictor of morbidity [Kerem et al., 1992], while pulmonary exacerbations are associated with a non-recoverable loss in lung function and decline in health status in many patients [Sanders et al., 2010].

Choosing a study duration appropriate to the drug being tested is important. While CFTR modulators can lead to a relatively rapid improvement in lung function [Rowe et al., 2014], longer-term trials are required to show benefits from anti-inflammatory therapies that aim to stem the decline in lung function and/or decreasing pulmonary exacerbation rate. The CFF-ASG recommended that trials Phase II should be at least 3-6 months [Torphy et al., 2015], but for more conclusive data on anti-inflammatory effects, a 12-month study may be preferred. The current study had a 48-week treatment period.

Enrolling the most appropriate patient phenotype is key to assessing clinical outcomes in a trial for a novel potential therapy. Patients for EMPIRE-CF were selected based on stringent inclusion criteria (age 18-30 years, $FEV_1pp \geq 50$, and at least one exacerbation in the past year).

This enriched the study population with patients who are most susceptible to pulmonary exacerbations and annual lung function decline. The enrolled patients experienced a mean of 2.1 exacerbations in the prior year. Modelling $FEV_1pp$ decline from a similar patient group in the CFPR (Cystic Fibrosis Foundation, 2015) suggests that patients eligible for this study may have an annual decline in $FEV_1pp$ of 3.5 (standard deviation [SD] 7.9), ranging from 2.7 (SD 7.6) for those with one exacerbation in the year prior, to 3.7 (SD 7.9) for those with 2, and 5.1 (SD 8.4) for those with ≥3 [Elborn et al., 2018]. Importantly, the total trial population size was calculated to ensure that the trial was sufficiently powered to show a difference in lung function decline from placebo. With trial population size and trial duration, there was also the potential that a benefit in pulmonary exacerbations may be detectable in this population.

Ensuring treatment arms were well balanced with respect to patient characteristics would help identify any specific patient groups that are more likely to benefit from acebilustat and who could be included in future clinical trials. Randomization was, therefore, stratified by baseline $FEV_1pp$, number of pulmonary exacerbations in the prior 12 months, and use of CFTR-modulating therapy. Stratification based on concomitant CFTR modulator use is important as neutrophil elastase is shown to downregulate CFTR [Le Gars, et al. 2013]; an anti-inflammatory agent, such as acebilustat, that reduces neutrophil elastase could have synergistic effects with CFTR modulators.

It was expected that the unique and rigorous design elements of the EMPIRE-CF trial would help identify the optimal patient population, dose, duration and endpoints for future trials, and widen our understanding of the efficacy of acebilustat in patients with CF. The present study provides evidence that pulmonary exacerbation is a better outcome measure for anti-inflammatory therapy such as acebilustat than change in $FEV_1pp$. No difference between acebilustat and placebo was observed for the primary endpoint, absolute change in $ppFEV_1$ from baseline at Week 48.—Given the mechanism of action of acebilustat as an anti-inflammatory agent, and prior experience with ibuprofen [Konstan et al. 1995], an acute increase from baseline in $ppFEV_1$ signifying a bronchodilatory or mucociliary clearance effect would not be expected. Additionally, to demonstrate a reduction in decline of lung function versus placebo would likely have required a longer trial as was the case with the 4-year high dose ibuprofen study [Konstan et al. 1995].

Importantly, analyses of the secondary endpoints showed that acebilustat treatment led to a numerical decrease in rate of pulmonary exacerbations, an increase in the time to first pulmonary exacerbation, and a higher proportion of patients with no pulmonary exacerbations. These differences from placebo were numerical but were internally consistent across several measures of exacerbations. These effects were particularly evident in patients who had milder disease (ppFEV$_1$>75% at baseline), consistent with previous findings that high dose ibuprofen treatment in children resulted in a lower rate of FEV1 decline and improved survival in children with evidence of advancing lung disease (ppFEV$_1$<100) but still in the milder population (ppFEV$_1$≥60) whereas there was no survival benefit observed in children with advanced lung disease (ppFEV$_1$<60) [Konstan et al. 2018]. In addition, the magnitude of the effect of acebilustat on pulmonary exacerbations was also more prominent in those using concomitant CFTR modulators, a group that may more closely resemble those with milder CF lung disease due to partial restoration of CFTR activity.

Although CFTR modulators have been shown to reduce the rate of lung function decline, they have not consistently shown an impact on markers of airway inflammation, and patients receiving CFTR modulator treatment still experience exacerbations and progressive loss of lung function [Sawicki et al. 2015; Konstan et al. 2017; Hisert et al. 2017; Rowe et al. 2014]. Our study findings suggest that the addition of acebilustat to CFTR modulator therapy may further reduce pulmonary exacerbations and potentially further reduce long-term loss of lung function. Trials of longer duration are needed to detect the effect of combination treatment on the trajectory of lung function decline.

Reducing pulmonary exacerbations is a critical goal of CF therapy, as exacerbations are associated with significant morbidity, decline in lung function, and early death [de Boer et al. (2011); Konstan et al. 2012; Stephenson et al. 2015]. The findings of the present study indicate that targeting neutrophil-mediated inflammation in CF with acebilustat could have clinical benefits by reducing pulmonary exacerbations, particularly in the context of concomitant CFTR modulator treatment, and in patients with mild lung disease. This approach warrants further investigation in these populations.

Direct targeting of LTB$_4$ inflammatory signaling was investigated in a clinical trial of amelubant (BIIL, 284), an antagonist of the BLT1 receptor, but this trial in patients with stable CF lung disease was terminated early due to an increase in serious pulmonary AEs [Konstan et al. 2014]. Amelubant, at the doses used in the study, may have had an overly potent effect on the BLT1 receptor, impairing antibacterial defenses, and permitting increased infection [Chmiel et al. 2007; Dorin et al. 2014]. Its mechanism as a receptor antagonist may also have resulted in increased LTB$_4$ presence in the airways as a deleterious consequence. As acebilustat acts to reduce LTB$_4$ synthesis by inhibiting the LTA$_4$H enzyme, it is likely to downregulate signaling through the BLT1 receptor rather than block signaling. This is reflected in the acceptable safety profile observed for acebilustat in this study where acebilustat was safe and well tolerated in patients with CF. Most AEs were either mild or moderate in intensity and considered by the investigator to be unrelated or unlikely to be related to study drug. There were few discontinuations due to AEs.

Neutrophil elastase is a key marker of inflammation associated with lung function decline in patients with CF [Mayer et al. (2007)]. In a phase 1 trial of acebilustat, sputum levels of neutrophil elastase, as well as sputum neutrophil DNA and serum high-sensitivity C-reactive protein, were reduced with acebilustat treatment compared with placebo [Elborn et al. (2017)]. We did not observe similar changes in this study. This finding may be due to limitations related to sputum collection, processing, and analyses from multiple clinical sites including the need to freeze samples to conduct centralized analysis, which has the propensity to release intracellular neutrophil elastase. High-sensitivity C-reactive protein, a marker of systemic inflammation, may have been impacted by intercurrent illnesses in this study where patients, though stable at randomization, had pulmonary exacerbations throughout the trial increasing variance and adversely influencing detection of stable changes between groups.

This trial highlights the challenges of designing a clinical trial for an anti-inflammatory agent at the phase 2 stage of drug development. The study was powered based on ppFEV$_1$, which required a more manageable sample size than powering such a study based on pulmonary exacerbations, even though this is a more meaningful measure of anti-inflammatory drug activity. Future clinical trials will require adequate statistical powering for pulmonary exacerbation endpoints, for which a numerical signal of benefit was seen in this trial. This poses an obvious challenge to assess anti-inflammatory agents early in clinical development, since biomarkers of sputum are not necessarily predictive of intermediate term benefit. By intention, we enrolled a population at risk for future pulmonary exacerbations which may have been a beneficial design feature that enabled detection of the positive trends in pulmonary exacerbations found in this study.

In summary, while there was no meaningful effect on ppFEV$_1$, positive and clinically relevant trends of the effect of acebilustat on rate of and time to first pulmonary exacerbation as well as the proportion of patients free of pulmonary exacerbations were observed, particularly in patients with mild disease and in those receiving concomitant CFTR modulator therapy. In the future, the majority of people with CF are projected to have mild lung disease (CFF Registry Report, 2017) and be on concomitant CFTR modulators. Given the importance of reducing pulmonary exacerbations in the treatment of patients with CF, further clinical investigation of acebilustat is warranted, focusing on these patient populations.

In conclusion, acebilustat is the first novel anti-inflammatory molecule to prospectively demonstrate benefits in both reducing the frequency of pulmonary exacerbations and prolonging time to first exacerbation, when added to a CF patient's existing treatment regimen in a clinical trial. Acebilustat treatment had a significant effect on reducing the rate of pulmonary exacerbation and this effect was most notable in patients of the mild lung disease population (having a FEV1pp of greater than 75 at baseline) and in patients on CFTR modulator therapy. Acebilustat-treated patients had a lower frequency of pulmonary exacerbations, particularly as recruited patients had exacerbations in the year prior to study entry and therefore at high risk of new exacerbations. It was also observed that a higher proportion of acebilustat-treated patients remained exacerbation free during the study compared to placebo. These data suggest that anti-inflammatory therapy effectiveness may be better assessed using clinical events such as pulmonary exacerbations. Pulmonary exacerbations, which are a clinical marker of unbridled lung inflammation, are significant events leading to acute decompensation and chronic decline of lung function and are strongly related to reduced survival. Given this, acebilustat has the potential to protect patients from the progressive and irreversible damage that is associated with CF.

TABLE 2

Inclusion and Exclusion criteria

Inclusion criteria 18 to 30 years of age inclusive at the time of screening
Documented, confirmed diagnosis of pulmonary CF (defined as follows): CF signs and symptoms AND either two CFTR mutations on genetic testing OR sweat chloride ≥60 mEq/L
At least one pulmonary exacerbation, based on the investigator's judgment, in the 12 months before screening
On a stable regimen of CF treatments with no change for at least 14 days before screening and between screening and baseline
If on ivacaftor or ivacaftor-lumacaftor combination, on a stable regimen for at least 8 weeks before baseline
$FEV_1pp \geq 50$ at screening
Able to perform spirometry according to European Respiratory Society/American Thoracic Society guidance Exclusion criteria In the opinion of the investigator, any significant clinical/laboratory/radiological/spirometric sign of unstable or unexpectedly deteriorating respiratory disease within 14 days before screening or between screening and baseline (these clinical/laboratory/radiological/spirometric signs include, but are not limited to, features suggestive of a pulmonary exacerbation as suggested by the modified Fuchs' criteria)
Colonization with organisms associated with a more rapid decline in respiratory function in CF patients (e.g. all *Burkholderia* species, *Mycobacterium abscessus*); patients with a history of a positive culture could be considered free of colonization if she/he has had six subsequent respiratory tract cultures negative for these bacteria within the past 24 months prior to screening, with one of these cultures obtained within 6 months prior to screening
Use of systemic corticosteroids, or systemic antimicrobial therapy (other than chronic antimicrobial use, e.g. azithromycin, flucloxacillin, itraconazole) within 14 days before screening or between screening and baseline
Regular use (>3 times per week) of a high-dose NSAID (e.g. >1.6 g ibuprofen/day) within 60 days before screening or between screening and baseline CF, cystic fibrosis; CFTR, cystic fibrosis transmembrane conductance regulator; $FEV_1pp$, forced expiratory volume in 1 second percent predicted; NSAID, non-steroidal anti-inflammatory drug; ULN, upper limit of normal.

TABLE 3

Primary and secondary endpoints

Primary endpoints

Absolute change from baseline to Week 48 in $FEV_1pp$
Safety and tolerability

Secondary endpoints

Number of pulmonary exacerbations
Time to first pulmonary exacerbation
Biomarker levels (sputum DNA and elastase, serum hs-CRP)

Exploratory endpoints

Sputum bacterial density (total and that of *P. aeruginosa*, *Burkholderia cepacia* complex, *Achromobacter xylosoxidans*, *Stenotrophomonas maltophilia*, and *Staphylococcus aureus* [including methicillin-resistant *S. aureus* and small colony variants of *S. aureus*])
Change from baseline in health-related quality of life as measured by the CFQ-R CFQ-R, Cystic Fibrosis Questionnaire—Revised; CFU, colony-forming unit; $FEF_{25-75}\%$, forced expiratory flow during the middle portion of the forced vital capacity; $FEV_1pp$, forced expiratory volume in 1 second percent predicted; FVCpp, forced vital capacity percent predicted; hs-CRP, serum high-sensitivity C-reactive protein.

REFERENCES

Afonso P V, Janka-Junttila M, Lee Y J, McCann C P, Oliver C M, Aamer K A, Losert W, Cicerone M T, Parent C A. LTB4 is a signal-relay molecule during neutrophil chemotaxis. Dev Cell 2012; 22:1079-91.

Alten R, Gromnica-Ihle E, Pohl C, Emmerich J, Steffgen J, Roscher R, Sigmund R, Schmolke B, Steinmann G. Inhibition of leukotriene B4-induced CD11B/CD18 (Mac-1) expression by BIIL 284, a new long acting LTB4 receptor antagonist, in patients with rheumatoid arthritis. Ann Rheum Dis. 2004; 63:170-6.

Balfour-Lynn I M, Welch K. Inhaled corticosteroids for cystic fibrosis. Cochrane Database of Systematic Reviews 2016: CD001915.

Birke F W, Meade C J, Anderskewitz R, Speck G A, Jennewein J-M. In vitro and in vivo pharmacological characterization of BIIL 284, a novel and potent leukotriene B4 receptor antagonist. WET 2001; 297:458-66.

Block J K, Vandemheen K L, Tullis E, Fergusson D, Doucette S, Haase D, Berthiaume Y, Brown N, Wilcox P, Bye P, Bell S, Noseworthy M, Pedder L, Freitag A, Paterson N, Aaron S D. Predictors of pulmonary exacerbations in patients with cystic fibrosis infected with multi-resistant bacteria. Thorax 2006; 61:969-74.

Cantin A M, Hartl D, Konstan M W, Chmiel J F. Inflammation in cystic fibrosis lung disease: Pathogenesis and therapy. J Cyst Fibros 2015; 14:419-30.

Cheng K, Ashby D, Smyth R L. Oral steroids for long-term use in cystic fibrosis. Cochrane Database Syst Rev 2015; CD000407.

Chmiel J F, Konstan M W, Accurso F J, Lymp J, Mayer-Hamblett N, VanDevanter D R, Rose L M, Ramsey B W, Assessment of Induced Sputum in Cystic Fibrosis Study Group. Use of ibuprofen to assess inflammatory biomarkers in induced sputum: Implications for clinical trials in cystic fibrosis. J Cyst Fibros 2015; 14:720-6.

Chmiel J F, Konstan M W, Elborn J S. Antibiotic and anti-inflammatory therapies for cystic fibrosis. Cold Spring Harb Perspect Med 2013; 3:a009779.

Cystic Fibrosis Patient Registry. 2014. Cystic Fibrosis Foundation. Available on request from https://www.cff.org/Research/Researcher-Resources/Tools-and-Resources/Patient-Registry-Data-Requests/. Last accessed 12 Mar. 2018.

Cystic Fibrosis Patient Registry. 2015. Cystic Fibrosis Foundation. Available on request from https://www.cff.org/Research/Resarcher-Resources/Tools-and-Resources/Patient-Registry-Data-Requests/. Last accessed 12 Mar. 2018.

Cystic Fibrosis Foundation Registry Report, 2017. Cystic Fibrosis Foundation. https://www.cff.org/Research/Researcher-Resources/Patient-Registry/2017-Patient-Registry-Annual-Data-Report.pdf Döring G, Bragonzi A, Paroni M, Aktürk F F, Cigana C, Schmidt A, Gilpin D, Heyder S, Born T, Smaczny C, Kohlhaufl M, Wagner T O, Loebinger M R, Bilton D, Tunney M M, Elborn J S, Pier G B, Konstan M W, Ulrich M. BIIL 284 reduces neutrophil numbers but increases P. aeruginosa bacteremia and inflammation in mouse lungs. J Cyst Fibros 2014; 13:156-63.

Downey D G, Bell S C, Elborn J S. Neutrophils in cystic fibrosis. Thorax 2009; 64:81-8.

Elborn J S, Ahuja S, Springman E, Mershon J, Grosswald R, Rowe S M. Demographics of patients in a phase 2 trial of acebilustat in patients with C F (EMPIRE C F). Submitted to the European Cystic Fibrosis Society congress, 2018.

Elborn J S, Horsley A, MacGregor G, Bilton D, Grosswald R, Ahuja S, Springman E B. Phase I studies of acebilustat: biomarker response and safety in patients with cystic fibrosis. Clin Transl Sci 2017a; 10:28-34.

Elborn J S, Bhatt L, Grosswald R, Ahuja S, Springman E B. Phase I studies of acebilustat: pharmacokinetics, pharmacodynamics, food effect, and CYP3A induction. Clin Transl Sci 2017b; 10:20-27.

Elborn J S, Perrett J, Forsman-Semb K, Marks-Konczalik J, Gunawardena K, Entwistle N. Efficacy, safety and effect on biomarkers of AZD9668 in cystic fibrosis. Eur Respir J 2012; 40: 969-76.

Fleming T R, Richardson B A. Some design issues in trials of microbicides for the prevention of HIV infection. J Infect Dis 2004; 190:666-74.

Fuchs H J, Borowitz D S, Christiansen D H, Morris E M, Nash M L, Ramsey B W, Rosenstein B J, Smith A L, Wohl M E; The Pulmozyme Study Group. Effect of aerosolized recombinant human DNase on exacerbations of respiratory symptoms and on pulmonary function in patients with cystic fibrosis. N Engl J Med 1994; 331:637-42.

Harman K, Dobra R, Davies J C. Disease-modifying drug therapy in cystic fibrosis. Paediatr Respir Rev 2017 [e-pub ahead of print].

Kerem E, Reisman J, Corey M, Canny G J, Levison H. Prediction of mortality in patients with cystic fibrosis. N Engl J Med. 1992; 326:1187-91.

Kernan W N, Viscoli C M, Makuch R W, Brass L M, Horwitz R I. Stratified randomization for clinical trials. J Clin Epidemiol 1999; 52:19-26.

Konstan M W, Byard P J, Hoppel C L, Davis P B. Effect of high-dose ibuprofen in patients with cystic fibrosis. N Engl J Med 1995; 332:848-54.

Konstan M W, Döring G, Heltshe S L, Lands L C, Hilliard K A, Koker P, Bhattacharya S, Staab A, Hamilton A on behalf of the Investigators and Coordinators of BI Trial 543.45. A randomized double blind, placebo controlled phase 2 trial of BIIL 284 BS (an LTB4 receptor antagonist) for the treatment of lung disease in children and adults with cystic fibrosis. J Cyst Fibros 2014; 13:148-55.

Konstan M W, Ratjen F. Effect of dornase alfa on inflammation and lung function: potential role in the early treatment of cystic fibrosis. J Cyst Fibros 2012; 11:78-83.

Konstan M W, VanDevanter D R, Sawicki G S, Pasta D J, Foreman A J, Neiman E A, et al. Association of High-Dose Ibuprofen Use, Lung Function Decline, and Long-Term Survival in Children with Cystic Fibrosis. Annals of the American Thoracic Society. 2018; 15:485-93. Konstan M W, Vargo K M, Davis P B. Ibuprofen attenuates the inflammatory response to Pseudomonas aeruginosa in a rat model of chronic pulmonary infection. Implications for antiinflammatory therapy in cystic fibrosis. Am Rev Respir Dis 1990; 141:186-92.

Konstan M W, Wagener J S, Vandevanter D R, Pasta D J, Yegin A, Rasouliyan L, Morgan W J. Risk factors for rate of decline in FEV1 in adults with cystic fibrosis. J Cyst Fibros. 2012; 11:405-11.

Lachin J M. Worst-rank score analysis with informatively missing observations in clinical trials. Control Clin Trials 1999; 20:408-22.

Lämmermann T, Afonso P V, Angermann B R, Wang J M, Kastenmuller W, Parent C A, Germain R N. Neutrophil swarms require LTB4 and integrins at sites of cell death in vivo. Nature 2013; 498:371-5.

Lands L C, Dauletbaev N. High-dose ibuprofen in cystic fibrosis. Pharmaceuticals (Basel) 2010; 3:2213-24.

Le Gars M, Descamps D, Roussel D, Saussereau E, Guillot L, Ruffin M, Tabary O, Hong S S, Boulanger P, Paulais M, Malleret L, Belaaouaj A, Edelman A, Huerre M, Chignard M, Sallenave J M. Neutrophil elastase degrades cystic fibrosis transmembrane conductance regulator via calpains and disables channel function in vitro and in vivo. Am J Respir Crit Care Med 2013; 187:170-9.

Li L, Somerset S. Digestive system dysfunction in cystic fibrosis: challenges for nutrition therapy. Dig Liver Dis 2014; 46:865-74.

Liou T G, Elkin E P, Pasta D J, Jacobs J R, Konstan M W, Morgan W J, Wagener J S. Year-to-year changes in lung function in individuals with cystic fibrosis. J Cyst Fibros. 2010; 9:250-6.

Marcos V, Zhou-Suckow Z, Yildirim A, Bohla A, Hector A, Vitkov L, Krautgartner W, Stoiber W, Griese M, Eickelberg O, Mall M, Hartl D; Free DNA in cystic fibrosis airway fluids correlates with airflow obstruction. Mediators of Inflammation 2015; 408935:1-11

Miller M R, Hankinson J, Brusasco V, Burgos F, Casaburi R, Coates A, Crapo R, Enright P, van der Grinten C P, Gustafsson P, Jensen R, Johnson D C, MacIntyre N, McKay R, Navajas D, Pedersen O F, Pellegrino R, Viegi G, Wanger J; ATS/ERS Task Force. Standardisation of spirometry. Eur Respir J 2005; 26:319-38.

Mogayzel P J Jr, Naureckas E T, Robinson K A, Mueller G, Hadjiliadis D, Hoag J B, Lubsch L, Hazle L, Sabadosa K, Marshall B; Pulmonary Clinical Practice Guidelines Committee. Cystic fibrosis pulmonary guidelines. Chronic medications for maintenance of lung health. Am J Respir Crit Care Med 2013; 187:680-9.

Moss R B, Mistry S J, Konstan M W, Pilewski J M, Kerem E, Tal-Singer R, Lazaar A L; CF2110399 Investigators. Safety and early treatment effects of the CXCR2 antagonist S B-656933 in patients with cystic fibrosis. J Cyst Fibros 2013; 12:241-8.

Oermann C M, Sockrider M M, Konstan M W. The use of anti-inflammatory medications in cystic fibrosis: trends and physician attitudes. Chest. 1999; 115:1053-8.

Perez A, Issler A C, Cotton C U, Kelley T J, Verkman A S, Davis P B. CFTR inhibition mimics the cystic fibrosis inflammatory profile. Am J Physiol Lung Cell Mol Physiol 2007; 292:L383-95.

Prescribers' Digital Reference. Ibuprofen: drug summary. Available from http://www.pdr.net/drug-summary/Ibuprofen-Tablets-ibuprofen-2618. Last accessed 26 Mar. 2018.

Quittner A L, Sweeny S, Watrous M, et al. Translation and linguistic validation of a disease specific quality of life measure for cystic fibrosis. J Pediatr Psychol. 2000; 25:403-14.

Ross K R, Chmiel J F, Konstan M W. The role of inhaled corticosteroids in the management of cystic fibrosis. Paediatr Drugs 2009; 11:101-13.

Rowe S M, Heltshe S L, Gonska T, Donaldson S H, Borowitz D, Gelfond D, Sagel S D, Khan U, Mayer-Hamblett N, Van Dalfsen J M, Joseloff E, Ramsey B W; GOAL Investigators of the Cystic Fibrosis Foundation Therapeutics Development Network. Clinical mechanism of the cystic fibrosis transmembrane conductance regulator potentiator ivacaftor in G551D-mediated cystic fibrosis. Am J Respir Crit Care Med 2014; 190:175-84.

Rubin B K. CFTR is a modulator of airway inflammation. Am J Physiol Lung Cell Mol Physiol 2007; 292:L381-2.

Sadik C D, Luster A D. Lipid-cytokine-chemokine cascades orchestrate leukocyte recruitment in inflammation. J Leukoc Biol 2012; 91:207-15.

Sanders D B, Bittner R C, Rosenfeld M, Hoffman L R, Redding G J, Goss C H. Failure to recover to baseline pulmonary function after cystic fibrosis pulmonary exacerbation. Am J Respir Crit Care Med 2010; 182:627-32.

Sly P D, Gangell C L, Chen L, Ware R S, Ranganathan S, Mott L S, Murray C P, Stick S M; AREST C F Investigators. Risk factors for bronchiectasis in children with cystic fibrosis. N Engl J Med 2013; 368:1963-70.

Southern K W, Barker P M, Solis-Moya A, Patel L. Macrolide antibiotics for cystic fibrosis. Cochrane Database Syst Rev 2012: CD002203.

Tirouvanziam R. Neutrophilic inflammation as a major determinant in the progression of cystic fibrosis. Drug News Perspect 2006; 19:609-14.

Tirouvanziam R, Khazaal I, Péault B. Primary inflammation in human cystic fibrosis small airways. Am J Physiol Lung Cell Mol Physiol 2002; 283:L445-51.

Torphy T J, Allen J, Cantin A M, Konstan M W, Accurso F J, Joseloff E, Ratj en F A, Chmiel J F; Antiinflammatory Therapy Working Group. Considerations for the conduct of clinical trials with antiinflammatory agents in cystic fibrosis. A Cystic Fibrosis Foundation Workshop Report. Ann Am Thorac Soc 2015; 12:1398-406.

VanDevanter D R, Morris N J, Konstan M W. IV-treated pulmonary exacerbations in the prior year: an important independent risk factor for future pulmonary exacerbations in cystic fibrosis. J Cyst Fibros 2016; 15:372-9.

Verhaeghe C, Delbecque K, de Leval L, Oury C, Bours V. Early inflammation in the airways of a cystic fibrosis foetus. J Cyst Fibros 2007; 6:304-8.

Waters V, Stanojevic S, Atenafu E G, Lu A, Yau Y, Tullis E, Ratjen F. Effect of pulmonary exacerbations on long-term lung function decline in cystic fibrosis. Eur Respir J. 2012; 40:61-6.

Woolhouse I S, Bayley D L, Stockley R A. Sputum chemotactic activity in chronic obstructive pulmonary disease: effect of α1-antitrypsin deficiency and the role of leukotriene B4 and interleukin 8. Thorax 2002; 57:709-14.

Sawicki G S, McKone E F, Pasta D J, Millar S J, Wagener J S, Johnson C A, et al. Sustained benefit from ivacaftor demonstrated by combining clinical trial and cystic fibrosis patient registry data. American journal of respiratory and critical care medicine. 2015; 192:836-42.

Konstan M W, McKone E F, Moss R B, Marigowda G, Tian S, Waltz D, et al. Assessment of safety and efficacy of long-term treatment with combination lumacaftor and ivacaftor therapy in patients with cystic fibrosis homozygous for the F508del-CFTR mutation (PROGRESS): a phase 3, extension study. Lancet Respir Med. 2017; 5:107-18.

Hisert K B, Heltshe S L, Pope C, Jorth P, Wu X, Edwards R M, et al. Restoring cystic fibrosis transmembrane conductance regulator function reduces airway bacteria and inflammation in people with cystic fibrosis and chronic lung infections. American journal of respiratory and critical care medicine. 2017 Jun. 15; 195(12):1617-28.

Rowe S M, Heltshe S L, Gonska T, Donaldson S H, Borowitz D, Gelfond D, et al. Clinical mechanism of the cystic fibrosis transmembrane conductance regulator potentiator ivacaftor in G551D-mediated cystic fibrosis. American journal of respiratory and critical care medicine. 2014; 190:175-84.

de Boer K, Vandemheen K L, Tullis E, Doucette S, Fergusson D, Freitag A, et al. Exacerbation frequency and clinical outcomes in adult patients with cystic fibrosis. Thorax. 2011; 66:680-5.

Konstan M W, Wagener J S, Vandevanter D R, Pasta D J, Yegin A, Rasouliyan L, et al. Risk factors for rate of decline in FEV1 in adults with cystic fibrosis. Journal of cystic fibrosis: official journal of the European Cystic Fibrosis Society. 2012; 11:405-11.

Stephenson A L, Tom M, Berthiaume Y, Singer L G, Aaron S D, Whitmore G A, et al. A contemporary survival analysis of individuals with cystic fibrosis: a cohort study. The European respiratory journal. 2015; 45:670-9.

Konstan M W, Doring G, Heltshe S L, Lands L C, Hilliard K A, Koker P, et al. A randomized double blind, placebo controlled phase 2 trial of BIIL 284 BS (an LTB4 receptor antagonist) for the treatment of lung disease in children and adults with cystic fibrosis. Journal of cystic fibrosis: official journal of the European Cystic Fibrosis Society. 2014; 13:148-55.

Lands L C, Milner R, Cantin A M, Manson D, Corey M. High-dose ibuprofen in cystic fibrosis: Canadian safety and effectiveness trial. The Journal of pediatrics. 2007; 151:249-54.

Lands L C, Stanojevic S. Oral non-steroidal anti-inflammatory drug therapy for lung disease in cystic fibrosis. The Cochrane database of systematic reviews. 2016; 4:Cd001505.

Chmiel J F, Konstan M W. Inflammation and anti-inflammatory therapies for cystic fibrosis. Clinics in chest medicine. 2007; 28:331-46.

Doring G, Bragonzi A, Paroni M, Akturk F F, Cigana C, Schmidt A, et al. BIIL 284 reduces neutrophil numbers but increases *P. aeruginosa* bacteremia and inflammation in mouse lungs.

Journal of cystic fibrosis: official journal of the European Cystic Fibrosis Society. 2014; 13:156-63.

Elborn J S, Horsley A, MacGregor G, Bilton D, Grosswald R, Ahuja S, et al. Phase I Studies of Acebilustat: Biomarker Response and Safety in Patients with Cystic Fibrosis. Clinical and translational science. 2017; 10:28-34.

Mayer-Hamblett N, Aitken M L, Accurso F J, Kronmal R A, Konstan M W, Burns J L, et al. Association between pulmonary function and sputum biomarkers in cystic fibrosis. American journal of respiratory and critical care medicine. 2007; 175:822-8.

While this invention has been particularly shown and described with references to preferred embodiments thereof, it will be understood by those skilled in the art that various changes in form and details may be made therein without departing from the scope of the invention encompassed by the appended claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference. The relevant teachings of all patents, published applications and references cited herein are incorporated by reference in their entirety.

What is claimed is:

1. A method of reducing pulmonary exacerbations in a cystic fibrosis patient, wherein the patient has a $FEV_1pp$ greater than or equal to about 75% at baseline, the method comprising orally administering to the patient acebilustat at a total daily dose of about 100 mg or less, wherein the patient experiences a decreased number of pulmonary exacerbations in the twelve month period after initiating the administration of acebilustat as compared to the number of pulmonary exacerbations in the twelve month period prior to initiating the administration of acebilustat; and/or
   wherein the patient does not experience a pulmonary exacerbation for at least forty-eight weeks after initiating the administration of acebilustat.
2. The method of claim 1, wherein acebilustat is administered at a total daily dose of about 50 mg.
3. The method of claim 1, wherein acebilustat is administered at a total daily dose of about 100 mg.
4. The method of claim 1, wherein the acebilustat is administered at a total daily dose from about 50 to about 100 mg.
5. The method of claim 1, wherein the patient is concomitantly treated with an additional therapeutic agent.
6. The method of claim 5, wherein the additional therapeutic agent is a mucolytic, a bronchodilator, an antibiotic, an anti-infective agent, a CFTR modulator, and an anti-inflammatory agent.
7. The method of claim 6, wherein the additional therapeutic agent is a CFTR modulator.
8. The method of claim 7, wherein the CFTR modulator is a CFTR potentiator and/or a CFTR corrector.
9. The method of claim 7, wherein the patient is undergoing concomitant treatment with at least two CFTR correctors, or at least one CFTR corrector and at least one CFTR potentiator.
10. The method of claim 9, wherein the CFTR potentiator is ivacaftor.
11. The method of claim 9, wherein the CFTR corrector is lumacaftor or tezacaftor.
12. The method of claim 11, wherein the CFTR corrector is lumacaftor.
13. The method of claim 9, wherein a combination of ivacaftor and lumacaftor is administered.
14. The method of claim 9, wherein a triple combination regimen is administered.
15. The method of claim 1, wherein the patient is not undergoing concomitant treatment with a CFTR potentiator and/or a CFTR corrector.
16. The method of claim 1, wherein the patient has a CFTR mutation other than a F508del mutation.
17. The method of claim 1, wherein the patient has at least one allele with a F508del mutation.
18. A method of reducing pulmonary exacerbations in a cystic fibrosis patient, comprising measuring $FEV_1pp$ in the patient at baseline, and orally administering acebilustat at a total daily dose of about 100 mg or less to the patient if the patient has an $FEV_1pp$ greater than or equal to about 75% at baseline
   wherein the patient experiences a decreased number of pulmonary exacerbations in the twelve month period after initiating the administration of acebilustat as compared to the number of pulmonary exacerbations in the twelve month period prior to initiating the administration of acebilustat, and/or
   wherein the patient does not experience a pulmonary exacerbation for at least forty-eight weeks after initiating the administration of acebilustat.
19. The method of claim 18, wherein the patient is concomitantly treated with a CFTR modulator.
20. The method of claim 19, wherein the CFTR modulator is a CFTR potentiator.
21. The method of claim 19, wherein the CFTR modulator is a CFTR corrector.
22. The method of claim 20, wherein the CFTR potentiator is ivacaftor.
23. The method of claim 21, wherein the CFTR corrector is lumacaftor or tezacaftor.
24. The method of claim 8, wherein the CFTR modulator is a CFTR potentiator.
25. The method of claim 8, wherein the CFTR modulator is a CFTR corrector.
26. The method of claim 24, wherein the CFTR potentiator is ivacaftor.
27. The method of claim 25, wherein the CFTR corrector is lumacaftor or tezacaftor.

* * * * *